US012650416B2

(12) United States Patent
Sankary et al.

(10) Patent No.: US 12,650,416 B2
(45) Date of Patent: Jun. 9, 2026

(54) DRIVE ROUTE SELECTION METHODOLOGY

(71) Applicant: Aclima Inc., San Francisco, CA (US)

(72) Inventors: Nathan Sankary, Los Altos Hills, CA (US); Walker Alexander, Rockland, ME (US); Michael Browning, Oakland, CA (US); Jessica Jenkins, San Francisco, CA (US); Tobe Corazzini, Auburn, CA (US); Meghan Elizabeth Thurlow, San Francisco, CA (US); Zachary Kent Smith, New Lebanon, OH (US); Davida Herzl, San Francisco, CA (US)

(73) Assignee: Aclima Inc., San Leandro, CA (US)

( * ) Notice: Subject to any disclaimer, the term of this patent is extended or adjusted under 35 U.S.C. 154(b) by 263 days.

(21) Appl. No.: 18/242,740

(22) Filed: Sep. 6, 2023

(65) Prior Publication Data

US 2024/0077465 A1       Mar. 7, 2024

Related U.S. Application Data

(60) Provisional application No. 63/404,510, filed on Sep. 7, 2022.

(51) Int. Cl.
*G01N 33/00* (2006.01)
*G01C 21/36* (2006.01)

(52) U.S. Cl.
CPC ..... *G01N 33/0075* (2013.01); *G01C 21/3626* (2013.01); *G01N 33/0027* (2013.01); *G01N 33/0067* (2013.01); *G01N 33/0068* (2024.05)

(58) Field of Classification Search
CPC ........... G01N 33/0075; G01N 33/0027; G01N 33/0067; G01N 33/0068; G01N 33/0062; G01C 21/3626; G01C 21/3461
See application file for complete search history.

(56) References Cited

U.S. PATENT DOCUMENTS

2013/0285820 A1 * 10/2013 Assuncao ............... G01W 1/10
                                                                          702/3
2014/0316736 A1 * 10/2014 Strohbach ............... H04L 67/12
                                                                          702/127

(Continued)

FOREIGN PATENT DOCUMENTS

CN          112345698 A  *  2/2021  ......... G01N 33/0067

OTHER PUBLICATIONS

English Translation of CN-112345698-A (Year: 2025).*

*Primary Examiner* — Erin M Piateski
*Assistant Examiner* — Eisen Yim
(74) *Attorney, Agent, or Firm* — Van Pelt, Yi & James LLP

(57)                    ABSTRACT
A system, device, and method for sensing air quality with a sensor platform is disclosed. The method includes (i) directing a set of mobile sensors to a coarse region wherein the coarse region has coarse size based on variance of prior air quality measurements taken at locations within a vicinity of the coarse region, and (ii) directing the set of mobile sensors to a fine region wherein the fine region has a fine size based on variance of prior air quality measurements taken at locations within a vicinity of the fine region. The variance of air quality measurements associated with the fine region is greater than a variance of air quality measurements associated with the coarse region.

27 Claims, 33 Drawing Sheets

(56)                     References Cited

U.S. PATENT DOCUMENTS

| 2015/0327242 | A1* | 11/2015 | Wu | H04W 72/542 |
| | | | | 370/336 |
| 2016/0316334 | A1* | 10/2016 | Lection | H04W 4/023 |
| 2018/0057461 | A1* | 3/2018 | Buchan | A01N 43/40 |
| 2019/0178649 | A1* | 6/2019 | Lucus | G08G 3/00 |
| 2020/0378940 | A1* | 12/2020 | Pariseau | G01N 33/0075 |
| 2021/0140769 | A1* | 5/2021 | Langland | G01N 33/0062 |
| 2021/0255157 | A1* | 8/2021 | Rashid | G01N 21/39 |
| 2021/0396546 | A1* | 12/2021 | Nagao | G01N 33/0075 |
| 2022/0205966 | A1* | 6/2022 | Althoff | G01N 21/94 |
| 2023/0007082 | A1* | 1/2023 | Kelly | H04L 67/12 |
| 2023/0243678 | A1* | 8/2023 | Shire | G01D 21/00 |
| | | | | 702/188 |

* cited by examiner

200

Mobile Sensor Platform(s) Traverse Route(s) Collecting Position and Sensor Data — 202

Mobile Sensor Platforms Provide Position and Sensor Data — 204

Repeat Collecting and Sending Data on Additional Pass(es) Using Mobile Sensor Platform(s) — 206

450

500

660 —

800

$$\frac{\sum_{i} 1 + \sum_{i} 1}{1} \Bigg/ \sum_{i} x_i \approx 1$$

$$x_i = L(x_i / \mu_n, \sigma_n)$$

900

$$\frac{\sum_{i}\overline{x}_{i}+\sum_{i}x'_{i}}{I} \bigg/ \sum_{i}x_{i} > 1$$

$$x, x', \overline{x} = L(x_{i}/\mu_{n}, \sigma_{n})$$

950

1000

1400

1600

1700

Start

Obtain prior air quality measurements — 1805

Determine a spatial data variance of the prior air quality measurements across the geographic region — 1810

Determine a temporal data variance of the prior air quality measurements across the geographic region — 1815

Provide the spatial data variance and the temporal data variance — 1820

Done? — 1825

No

Yes

End

<u>1800</u>

2100

2200

DRIVE ROUTE SELECTION METHODOLOGY

CROSS REFERENCE TO OTHER APPLICATIONS

This application claims priority to U.S. Provisional Patent Application No. 63/404,510 entitled DRIVE ROUTE SELECTION METHODOLOGY filed Sep. 7, 2022 which is incorporated herein by reference for all purposes.

BACKGROUND OF THE INVENTION

Monitoring of environmental conditions includes measuring the levels of various components of the surroundings, allowing detection of potentially harmful air pollution, radiation, greenhouse gases, or other contaminants in the environment. Depending on the application, environmental monitoring systems can be used in outdoor or indoor settings. Monitoring of environmental conditions typically includes gathering environmental data. Environmental data includes detection and measurement of pollutants or contaminants such as nitrogen dioxide ($NO_2$), carbon monoxide (CO), nitrogen oxide (NO), ozone ($O_3$), sulfur dioxide ($SO_2$), carbon dioxide ($CO_2$), methane ($CH_4$), volatile organic compounds (VOC), air toxics, temperature, sound radiation, and particulate matter. In order to assess the effects of such pollutants, it is desirable to associate environmental data sensing these pollutants at particular times with geographic locations (homes, businesses, towns, etc.). Such an association would allow individuals and communities to evaluate the quality of their surroundings. Thus, data collected that is representative of the region is desired to be collected. Further, the data collected is desired to meet desired error tolerances, and be collected and processed efficiently. Thus, a mechanism for improving collection and processing of environmental data is desired.

BRIEF DESCRIPTION OF THE DRAWINGS

Various embodiments of the invention are disclosed in the following detailed description and the accompanying drawings.

DETAILED DESCRIPTION

Figure 1:
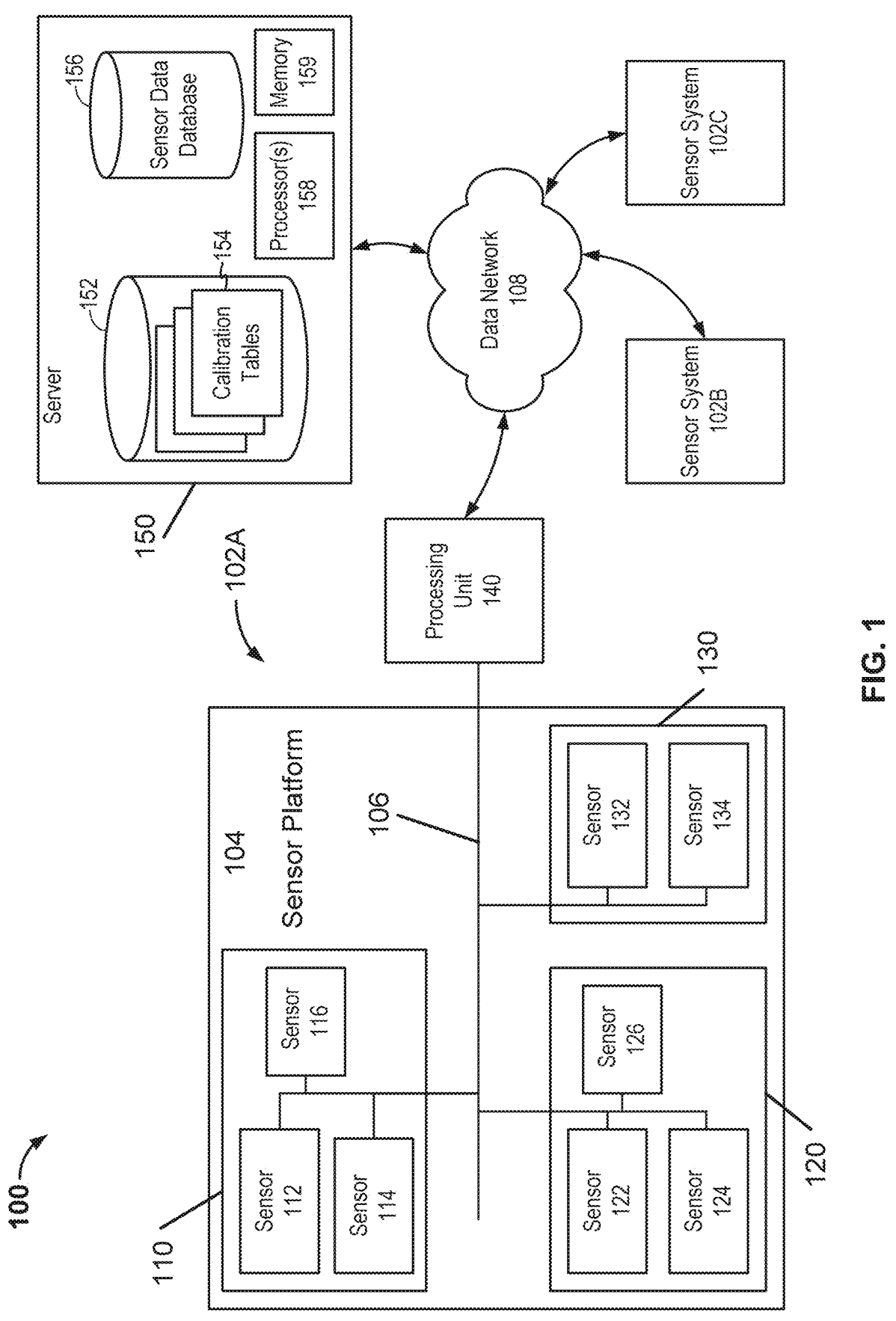
FIG. 1 illustrates an embodiment of a system for capturing environmental data using mobile sensor platforms and associating the environmental data with map features.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Various embodiments provide a method, system, or device for sensing air quality with a sensor platform. The method comprises (i) directing a set of mobile sensors to a coarse region wherein the coarse region has coarse size based on variance of prior air quality measurements taken at locations within the vicinity of region, and (ii) directing the set of mobile sensors to a fine region wherein the fine region has a fine size based on variance of prior air quality measurements taken at locations within the vicinity of the fine region. The variance of air quality measurements associated with the fine region is greater than a variance of air quality measurements associated with the coarse region.

Various embodiments provide a method, system, or device for sensing air quality with a sensor platform. The method comprises (i) directing an air quality measurement system to a predicted high information region wherein the predicted high information region is determined based on high variance of prior air quality measurements taken at different times, and (ii) directing the air quality measurement system to a predicted low information region wherein the predicted low information region is determined based on low variance of prior air quality measurements taken at different times. The air quality measurement system is preferentially directed to the high information region.

Mobile sensors might be used to collect environmental data. The mobile sensors may be comprised in an air quality measurement system (e.g., a sensor platform) that is deployed to various locations to collect the environmental data (e.g., air quality measurements). The air quality measurement system may be a vehicle having the mobile sensors thereon. A mobile sensor may be used to capture environmental data at a variety of locations. However, a mobile sensor is limited to capturing data for a particular time at its current location. Data at the same location for a different time may not be captured by the sensor. As a result, a mobile sensor might not capture temporal variations at a particular geographic location. Similarly, data in other locations for the particular time may not be captured by the sensor. Even if multiple mobile sensors are utilized, there may be temporal and/or geographic gaps in the data. For example, mobile sensors mounted on two different vehicles may move through a city capturing data substantially continuously for a year. However, there may still be significant amounts of time at any given location for which there is no data and/or locations that have little or no data captured for the entire year. Employing an extremely large number of mobile sensors capturing data twenty-four hours per day and seven days per week may fill in gaps in the data captured, but suffers from the same drawbacks as using a large number of stationary sensor platforms. Use of such a large number of mobile sensors may be expensive and may result in extremely large amounts of data (e.g. for mobile sensors capturing data every second) that are challenging to process in the desired amount of time. Consequently, a mechanism for capturing environmental data using mobile platforms that is efficient, that may capture temporal and localized geographic variations, and that may be used in assessing the environmental quality is desired.

Collection of air quality measurement data includes intelligently guiding air quality measurement systems (e.g., vehicles with mounted sensor platforms) to locations where data is to be collected (e.g., where data is needed for the model or analysis of air quality over a particular geographic region). The process of intelligently guiding the air quality measurement systems includes partitioning a contract region (e.g., the geographic region) into discrete objects (e.g., hexagonal areas) and systematically assigning a subset of these discrete objects to sessions (e.g., to vehicles for collecting during a session). According to various embodiments, the system/process collects a high-quality data set to populate a map over the geographic region over a series of sessions (e.g., over a time period over which air quality is to be monitored/analyzed over the geographic region).

A method for routing, through a geographic region over a time interval, a sensor platform mounted on a vehicle is described. The method includes receiving a precision level for at least one constituent of an environment measured by a sensor of the sensor platform. The precision level may correspond to a mean concentration of the constituent(s) over the time interval. In some embodiments, the precision level is based on a tolerance in a relative error rate and a false positive error rate. A reference dataset (e.g., historical air quality measurements) corresponding to the geographic region and the time interval is selected. From the reference dataset and the precision level, at least one minimum number of distinct samples for a plurality of geographic segments of the geographic region is determined. The method also includes randomly selecting target regions, locations within the target region, and/or a time of day to visit the location/target region in connection with planning an air quality measurement session(s). The target region location within a particular target region, and/or a time of day at which the location/target region is to be visited may be selected based at least in part on priorities assigned to target regions, locations, and/or times of day. For example, the random selection may include weighting the target regions, locations, and/or times of day based at least in part on the assigned priorities.

The number of passes for the geographic region is some function of the number of passes determined for each geographic segment in the geographic region. Each pass of the number of passes is part of a route for the vehicle. In some embodiments, the geographic segments include a plurality of road segments, each of the plurality of road segments having a length not exceeding one hundred meters. In some embodiments, the geographic segments include cells. Each of the cells may have a characteristic length not exceeding two hundred meters. Other road segment lengths, including larger road segments or larger cells, may be used in some embodiments. In some embodiments, the geographic segments include a plurality of hexagons (e.g., hexagonal regions). Each of the hexagons may be sized (e.g., split into a set of smaller hexagons or grouped with other equally-sized hexagons to form a larger merged hexagon) based at least in part on the data quality over each hexagon. An example of data quality measure for determining the size of the hexagons includes a data variance of the air quality measurements over the area defined by the hexagon(s) (e.g., historical air quality measurements, such as over a predefined time period). The data variance may comprise a spatial data variance of the air quality measurements.

In some embodiments, the system implements a data-driven approach to determining plans for sampling during a session.

The system uses a statistical measure (e.g., a data quality measure, such as spatial data variance) in connection with determining the specific regions that can be sampled. For example, the system divides a particular geographic region into a plurality of regions from which the system selects a set of target regions to be sampled during the session. The system may determine the specific regions (e.g., whether regions are to be merged or split) based at least in part on a determination of boundaries that define areas which can be reasonable represented by a single sample at a target location within the boundary. The system thus uses statistical analysis to define coarse or fine regions over which air quality measurements are to be collected.

In response to determining the set of regions within a geographic region, the system identifies a specific set of target regions that are to be included in the plan for a session to cause an air quality measurement system (e.g., a vehicle comprising the mobile sensor platform) to sample. The system identifies the set of target regions based at least in part on a random selection in which each region has an associated weighting corresponding to a prioritization.

The system determines a single location (e.g., a measurement location or a target region) in each of the target regions at which the target region is to be sampled (e.g., a location for which a sample is reasonably representative of the entire target region). The target location can be randomly selected. The target location may correspond to a particular road segment within the target region. Each location may be prioritized and assigned a weighting. The target location is then randomly selected according to the various weightings associated with the various locations within the target region. In some embodiments, the target locations are prioritized based at least in part on one or more of (i) pass count, (ii) likelihood that an anomaly or leak is expected to be observed, (iii) a variance of prior air quality measurements at the location, (iv) a time that has passed since a last sampling at the location, (v) the presence of a hazard, (vi) a construction zone, etc.

After determining the target locations to include the plan for a session, the system determines a plan or path to ensure that the air quality measurement system (e.g., the vehicle) is expected to visit each target location within the session. The determining the plan/path includes determining a set of road segments to connect a session starting location, the set of target locations, and a session ending location. The system may determine the set of road segments based on a balancing of the pass counts and travel time associated with each road segment. For example, the road segments may be prioritized and assigned weightings based at least in part on the associated pass counts and travel time. In addition, the system may prioritize road segments based on one or more of (a) the detection of a leak from the prior air quality measurement systems, (b) an expected likelihood that a leak will be observed at the road segment, (c) a current travel speed or congestion level, (e) the presence of a hazard at the road segment, and (f) the presence of a construction zone at the segment, etc.

In response to determining a plan for sampling air quality during a session, the system provides the plan to an air quality measurement system (e.g., a vehicle with the mobile sensor platform) that is to be deployed during the session. The system may dynamically update the plan based on the status of the air quality measurement system throughout the session (e.g., whether the system expects that the vehicle is still able to sample all target locations during the session), a deviation of the air quality measurement system from the planned route (e.g., if the vehicle took a wrong turn), etc.

In some embodiments, the system enforces temporal variability in the sampling of the target regions. The system randomly determines, for each target region, a time window within which the target region is to be sampled. The system then selects and assigns the target regions according to the time window constraints for each target region. If a particular hexagon and its neighboring hexagon can be driven at any time of day (e.g., the planning of the route does not have a time constraint for the hexagon(s)), then the system determines the plan to include subsequent driving of the particular hexagon and its neighboring hexagon (e.g., to efficiently direct the air quality measurement system during the session). However, if the particular hexagon has a time-window constraint indicating that it is to be driven between 8-11 am, and its neighboring hexagon has a time constraint indicating it is to be driven between 2-5 pm, then the system would not plan the session (e.g., the route for the session) to include successively driving the hexagon and its neighboring hexagon. Instead, the system plans the session to optimize efficiency of the planed subject to the various time constraints for the target regions.

Hyper-local environmental data, for example related to air quality and greenhouse gas data, can be collected using vehicles with air pollutants sensors installed. Embodiments of techniques usable in gathering hyper-local data are described in U.S. patent application Ser. No. 16/682,871, filed on Nov. 13, 2019, entitled HYPER-LOCAL MAPPING OF ENVIRONMENTAL CONDITIONS and assigned to the assignee of the present application, U.S. patent application Ser. No. 16/409,624, filed on May 10, 2019, entitled INTEGRATION AND ACTIVE FLOW CONTROL FOR ENVIRONMENTAL SENSORS and assigned to the assignee of the present application; U.S. patent application Ser. No. 16/773,873, filed on Jan. 27, 2020, entitled SENSOR DATA AND PLATFORMS FOR VEHICLE ENVIRONMENTAL QUALITY MANAGEMENT, assigned to the assignee of the present application and which claims priority to U.S. Patent Application Ser. No. 62/798,395 entitled SENSOR DATA AND PLATFORMS FOR VEHICLE ENVIRONMENTAL QUALITY MANAGEMENT and assigned to the assignee of the present application, which are all incorporated herein in their entirety for all purposes.

FIG. 1 depicts an embodiment of a system 100 for collecting and processing environmental data. System 100 includes multiple mobile sensor platforms 102A, 102B, 102C and server 150. In some embodiments, system 100 may also include one or more stationary sensor platforms 103, of which one is shown. Stationary sensor platform 103 may be used to collect environmental data at a fixed location. The environmental data collected by stationary sensor platform 103 may supplement the data collected by mobile sensor platforms 102A, 102B and 102C. Thus, stationary sensor platform 103 may have sensors that are the same as or analogous to the sensors for mobile sensor platforms 102A, 102B and 102C. In other embodiments, stationary sensor platform 103 may be omitted. Although a single server 150 is shown, multiple servers may be used. The multiple servers may be in different locations. Although three mobile sensor platforms 102A, 102B and 102C are shown, another number are typically present. Mobile sensor platforms 102A, 102B and 102C and stationary sensor platform(s) 103 may communicate with server 150 via a data network 108. The communication may take place wirelessly.

Mobile sensor platforms 102A, 102B and 102C may be mounted in a vehicle, such as an automobile or a drone. In some embodiments, mobile sensor platforms 102A, 102B and 102C are desired to stay in proximity to the ground to be better able to sense conditions analogous to what a human would experience. Mobile sensor platform 102A includes a bus 106, sensors 110, 120 and 130. Although three sensors are shown, another number may be present on mobile sensor platform 102A. In addition, a different configuration of components may be used with sensors 110, 120 and 130. Each sensor 110, 120 and 130 is used to sense environmental quality and may be of primary interest to a user of system 100. For example, sensors 110, 120 and 130 may be gas sensors, volatile organic compound (VOC) sensors, particulate matter sensors, radiation sensors, noise sensors, light sensors, temperature sensors, noise sensors or other analogous sensors that capture variations in the environment. For example, sensors 110, 120 and 130 may be used to sense one or more of $NO_2$, CO, NO, $O_3$, $SO_2$, $CO_2$, VOCs, $CH_4$, particulate matter, noise, light, temperature, radiation, and other compounds. In some embodiments, sensor 110, 120 and/or 130 may be a multi-modality sensor. A multi-modality gas sensor senses multiple gases or compounds. For example, if sensor 110 is a multi-modality $NO_2/O_3$ sensor, sensor 110 might sense both $NO_2$ and $O_3$ together. Sensor 110 may comprise a plurality of sensors, such as sensors 112, 114, and 116. Sensor 120 may comprise a plurality of sensors, such as sensors 122, 124, and 126. Sensor 130 may comprise a plurality of sensors, such as sensors 132 and 134.

Although not shown in FIG. 1, other sensors co-located with sensors 110, 120 and 130 may be used to sense characteristics of the surrounding environment including, in some instances, other gases and/or matter. Such additional sensors are exposed to the same environment as sensors 110, 120 and 130. In some embodiments, such additional sensors are in close proximity to sensors 110, 120 and 130, for example within ten millimeters or less. In some embodiments, the additional sensors may be further from sensors 110, 120 and 130 if the additional sensors sample the same packet of air inside of a closed system, such as a system of closed tubes. In some embodiments, temperature and/or pressure are sensed by these additional sensors. For example, an additional sensor co-located with sensor 110 may be a temperature, pressure, and relative humidity (T/P/RH) sensor. These additional co-located sensors may be used to calibrate sensors 110, 120 and/or 130. Although not shown, sensor platform 102A may also include a manifold for drawing in air and transporting air to sensors 110, 120 and 130 for testing.

Sensors 110, 120 and 130 provide sensor data over bus 106, or via another mechanism. In some embodiments, data from sensors 110, 120 and 130 incorporates time. This time may be provided by a master clock (not shown) and may take the form of a timestamp. Master clock may reside on sensor platform 102A, may be part of processing unit 140, or may be provided from server 150. As a result, sensors 110, 120 and 130 may provide timestamped sensor data to server 150. In other embodiments, the time associated with the sensor data may be provided in another manner. Because sensors 110, 120 and 130 generally capture data at a particular frequency, sensor data is discussed as being associated with a particular time interval (e.g., the period associated with the frequency), though the sensor data may be timestamped with a particular value. For example, sensors 110, 120 and/or 130 may capture sensor data every second, every two seconds, every ten seconds, or every thirty seconds. The time interval may be one second, two seconds, ten seconds, or thirty seconds. The time interval may be the same for all sensors 110, 120 and 130 or may differ for different sensors 110, 120 and 130. In some embodiments, the time interval for a sensor data point is centered on the timestamp. For example, if the time interval is one second and a timestamp is t1, then the time interval may be from t1−0.5 seconds to t1+0.5 seconds. However, other mechanisms for defining the time interval may be used.

Sensor platform 102A also includes a position unit 145 that provides position data. In some embodiments, position unit 145 is a global positioning satellite (GPS) unit. Consequently, system 100 is described in the context of a position unit 145. The position data may be time-stamped in a manner analogous to sensor data. Because position data is to be associated with sensor data, the position data may also be considered associated with time intervals, as described above. However, in some embodiments, position data (e.g., GPS data) may be captured more or less frequently than sensor data. For example, position unit 145 may capture position data every second, while sensor 130 may capture data every thirty seconds. Thus, multiple data points for the position data may be associated with a single thirty second time interval. The position data may be processed as described below.

Optional processing unit 140 may perform some processing and functions for data from sensor platform 104, may simply pass data from sensor platform 104 to server 150 or may be omitted.

Mobile sensors platforms 102B and 102C are analogous to mobile sensor platform 102A. In some embodiments, mobile sensor platforms 102B and 102C have the same components as mobile sensor platform 102A. However, in other embodiments, the components may differ. However, mobile sensor platforms 102A, 102B and 102C function in an analogous manner.

Server 150 includes sensor data database 156, calibration tables 154 (e.g., stored in database 152), processor(s) 158, memory 159. Processor(s) 158 may include multiple cores. Processor(s) 154 may include one or more central processing units (CPUs), one or more graphical processing units (GPUs) and/or one or more other processing units. Memory 159 can include a first primary storage, typically a random-access memory (RAM), and a second primary storage area, typically a non-volatile storage such as solid-state drive (SSD) or hard disk drive (HDD). Memory 159 stores programming instructions and data for processes operating on processor(s) 158. Primary storage typically includes basic operating instructions, program code, data and objects used by processor(s) 158 to perform their functions. Primary storage devices (e.g., memory 159) may include any suitable computer-readable storage media, described below, depending on whether, for example, data access needs to be bi-directional or uni-directional.

Sensor data database 152 includes data received from mobile sensor platforms 102A, 102B and/or 102C. After capture by mobile sensor platform 102A, 102B and/or 102C, sensor data stored in sensor data database 152 may be operated on by various analytics, as described below. Position data database 158 stores position data received from mobile sensor platforms 102A, 102B and/or 102C. In some embodiments, sensor data database 152 stores position data as well as sensor data. In such embodiments, position data database 158 may be omitted. Server 150 may include other databases and/or store and utilize other data. For example, server 150 may include calibration data (not shown) used in calibrating sensors 110, 120 and 130.

System 100 may be used to capture, analyze, and provide information regarding hyper-local environmental data. Mobile sensor platforms 102A, 102B and 102C may be used to traverse routes and provide sensor and position data to server 150. Server 150 may process the sensor data and position data. Server 150 may also assign the sensor data to map features corresponding to the locations of mobile sensor platforms 102A, 102B and 102C within the same time interval as the sensor data was captured. As discussed above, these map features may be hyper-local (e.g., one hundred meter or less road segments or thirty meter or less road segments). Thus, mobile sensor platforms 102A, 102B and 102C may provide sensor data that can capture variations on this hyper-local distance scale. Server 150 may provide the environmental data, a score, confidence score and/or other assessment of the environmental data to a user. Thus, using system 100 hyper-local environmental data may be obtained using a relatively sparse network of mobile sensor platforms 102A, 102B and 102C, associated with hyper-local map features and processed for improved understanding of users.

Figures 2, 3A:
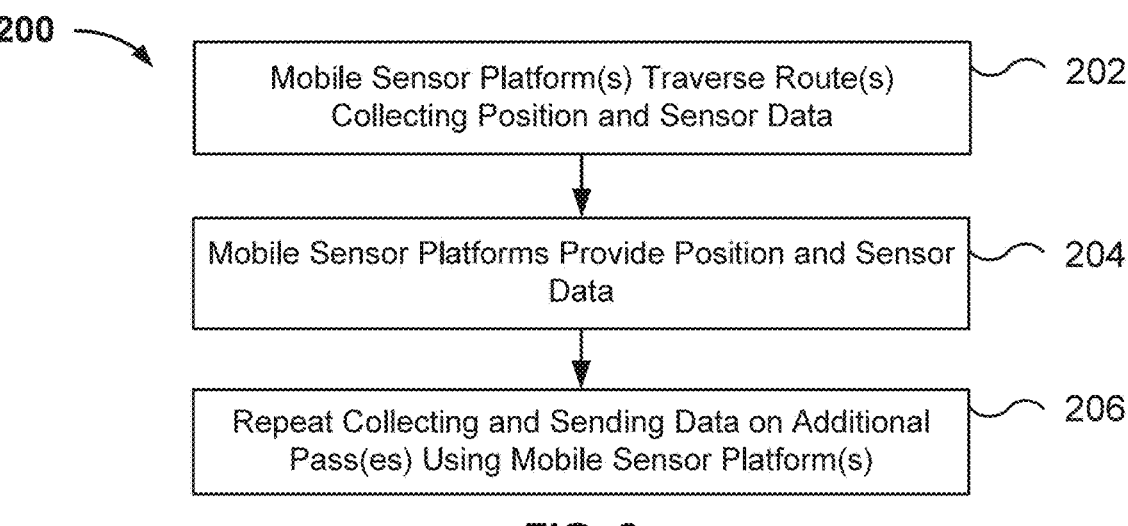
FIG. 2 illustrates an embodiment of a method for capturing environmental data using mobile sensor platforms.
FIG. 3A-3C illustrate a particular region and the embodiment of routes that may be traversed using a method for capturing environmental data using mobile sensor platforms.

FIG. 2 depicts an exemplary embodiment of method 200 for capturing environmental data using mobile sensor platforms, such as mobile sensor platforms 102A, 102B and/or 102C. Method 200 is described in the context of system 100, but may be performed using other systems. For clarity, only some portions of method 200 are shown. Although shown in a sequence, in some embodiments, processes may occur in parallel and/or in a different order.

Mobile sensor platforms traverse routes in a geographic region, at 202. While traversing the routes, the mobile sensor platforms collect not only sensor data, but also position data. For example, a mobile sensor platform may sense one or more of $NO_2$, CO, NO, $O_3$, $SO_2$, $CO_2$, $CH_4$, VOCs, particulate matter, other compounds, radiation, noise, light, and other environmental data at various times during traversal of the route. Other environmental characteristics, including but not limited to temperature, pressure, and/or humidity may also be sensed at 202. In addition, the time corresponding to the environmental data is also captured. The time may be in the form of a timestamp for the sensor data (sensor timestamp), which may correspond to a particular time interval. Different sensors on the mobile sensor platform may capture the environmental data at different times and/or at different frequencies. Also, at 202 the mobile sensor platforms capture position data, for example via a GPS unit. The position data may include location (as indicated by a GPS unit), velocity and/or other information related to the geographic location of the mobile sensor platform. In some embodiments, position data from other sources, such as acceleration, may be captured from by the vehicle or another source.

The position data may include a timestamp (position timestamp) or other indicator of the time at which the position data is captured.

The mobile sensor platforms provide the position and sensor data to a server, at 204. In some embodiments, mobile sensor platforms provide this data substantially in real time, as the mobile sensor platforms traverse their routes at 202. Thus, the position and sensor data may be transmitted wirelessly to the server. In some embodiments, some or all of the position and/or sensor data is stored at the mobile sensor platform and provided to the server at a later time. For example, the data may be transferred to the server when the mobile sensor platform returns to its base. In some embodiments, the mobile sensor platform may process the sensor data and/or position data prior to sending the sensor and/or position data to the server. In other embodiments, the mobile sensor platform provides little or no processing. The sensor data and position data may be sent at the same time or may be sent separately.

At 206, the route traversal and data collecting of 202 and data sending of 204 are repeated. Thus, the mobile sensor platforms may traverse the same or different routes at 206. In either case, multiple passes of the same geographic locations, and thus multiple passes of the same corresponding map features, are made at 206. In some embodiments, the repetition at 206 may be periodic (e.g., approximately every week, month, or other time period). In some embodiments, the repetition at 206 may be performed based on other timing. In some cases, the same mobile sensor platform is sent on the same route and/or collects data for the same map features. In some embodiments, different mobile sensor platforms collect data may be used for the same routes and/or map features. Also at 206, steps 202 and 204 may be performed multiple times. Thus, at 206, data for a particular region may be aggregated over time.

Figure 3B:
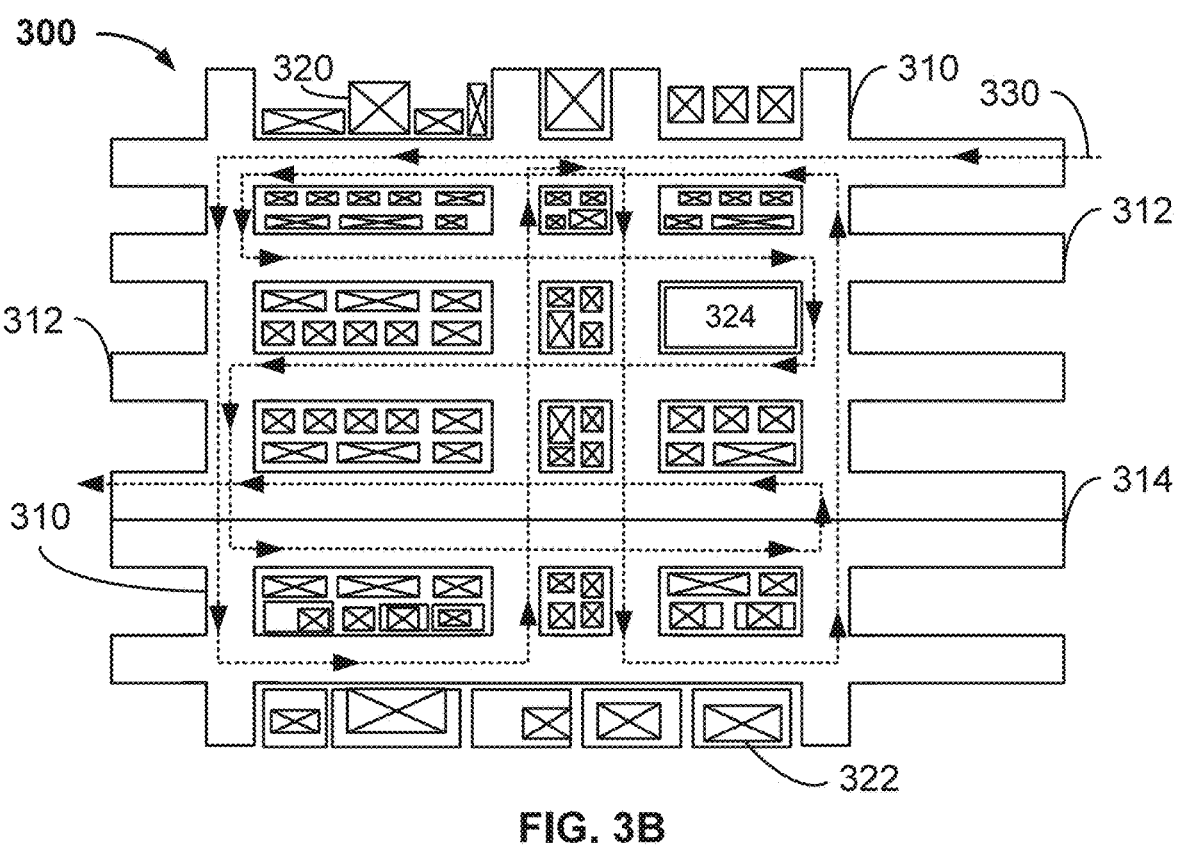
Figure 3C:
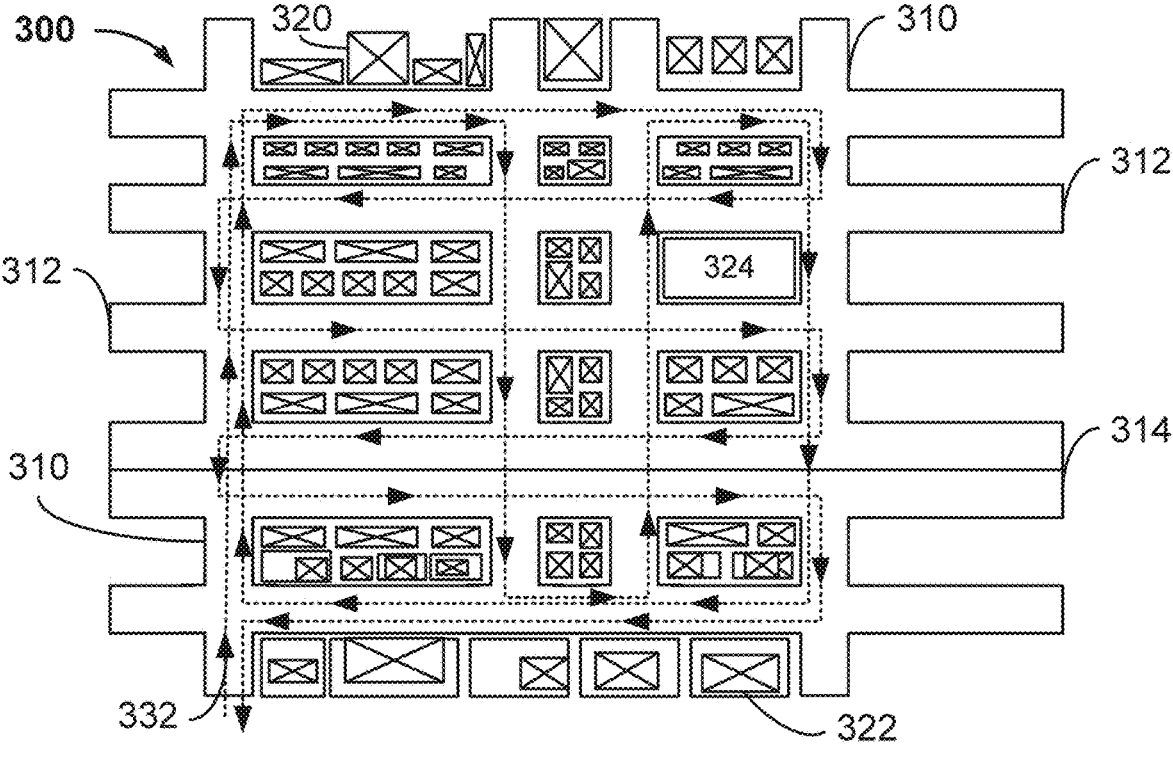

For example, FIGS. 3A-3C illustrate a particular geographic region and the routes that may be traversed using method 200. A map 300 corresponding to the geographic region is shown in FIG. 3A. Map 300 may be an open-source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot, or analogous item. As can be seen in FIG. 3A, the density and size of structures 320 and 322 vary across map 300. Similarly, the density and size of streets 312, 314 and 320 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by position unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses a different route. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation, and analysis. Sensor data and position data are sensed sufficiently frequently using method 200 that variations environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

For example, FIGS. 3A-3C illustrate a particular geographic region and the routes that may be traversed using method 200. A map 300 corresponding to the geographic region is shown in FIG. 3A. Map 300 may be an open-source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot, or analogous item. As can be seen in FIG. 3A, the density and size of structures 320 and 322 vary across map 300. Similarly, the density and size of streets 312, 314 and 320 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by position unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses a different route. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation, and analysis. Sensor data and position data are sensed sufficiently frequently using method 200 that variations environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

Figure 4A:
FIGS. 4A and 4B illustrate examples of data collection paths.
Figure 4A:
Figure 4B:
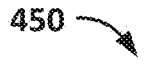
Figure 5A:
FIGS. 5A and 5B illustrate examples of data collection paths.
Figure 5B:
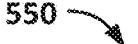
Figure 5B:
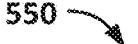

FIGS. 4A, 4B, 5A, and 5B illustrate examples of data collection paths. In the examples shown, FIGS. 4A and 5A show a map of driving routes or a sampling of a geographic region based on driving road segments within selected polygons/census tracts in the geographic region. In contrast, FIGS. 4B and 5B show a map of driving routes or a sampling of a geographic region based on driving a subset of randomly selected road segments within the geographic region.

Some related art systems for collecting environmental data over a geographic region include (a) obtaining a set of polygons corresponding to pre-defined census tracts over the geographic region, and (b) selecting a polygon(s) to be driven on a particular given day according to a number of times the polygon has been driven during a predefined time period (e.g., the most underdriven polygons are selected and assigned to a vehicle). However, such related art systems are found to introduce too much spatio-temporal correlation in the environmental data (e.g., the air quality measurements) to provide high quality and informative baseline maps. The polygons for such related art systems are generally defined by third party services and a definition of the polygons is generally a function of population. For example, the polygons are arbitrary shapes that may be based on definitions provided by one or more of counties, government boundaries, roads, city blocks, etc. During a session, the vehicle is directed to drive each road within the assigned polygon(s).

In the example shown, in FIG. 4A, map 400 illustrates the sampling of environmental data during a session based on selection of polygons from a set of predefined polygons. As illustrated, polygons 405, 410, 415, and 420 are sampled during the session. The data collection was focused specifically in polygons 405, 410, 415, and 420 thereby providing little data diversity across the entire geographic region. The emphatically displayed lines within the polygons are indicative of the roads along which the environmental data was sampled. As shown, the data collection according to selection of polygons from a set of predefined polygons results in the collection along each road within the selected polygons but a dearth of data collection in the remaining areas of the geographic region.

In the example shown in FIG. 5A, map 500 illustrates a sampling of environmental data using the same selection process as the sampling illustrated in map 400. Map 500 provides a representation of the sampling/coverage over a simulated 19 days of driving (e.g., 19 different sessions or set of sessions for a plurality of vehicles). Map 500 shows that sampling within the region is very focused on a small set of polygons/areas that each have a very dense environmental data collection. However, map 500 shows many areas within the geographic region with no environmental data collection thereby resulting in a poor representation of environmental data over the entire geographic region.

Some related art systems for collecting environmental data over a geographic region include (a) obtaining a set of polygons corresponding to pre-defined census tracts over the geographic region, (b) determining road segments within each of the polygons from an OpenStreetMap (OSM) definition, (c) determining a path to be driven to sample each polygon (e.g., shrink each polygon to a single elongated row, such as an OSM way, to be driven), and/or (d) selecting an OSM ways to be driven on a particular given day according to a number of times the OSM way has been driven during a predefined time period (e.g., the most underdriven roads are selected and assigned to a vehicle). Each session includes a subset of the assigned roads in the region(s), such that each session is given a fraction of the area of the area to drive, and no driver entered another driver's daily assigned region(s). The system for collecting environmental data using the OSM method improves the spatio-temporal correlation deficiency of related art systems that select polygons in the OSM definition to be driven.

Instead of directing drivers to a small number of larger polygons (e.g., census tracts), the system directs drivers to a large number of small road segments (e.g., the OSM ways). The assignment of specific road segments to be driven rather than larger polygon areas allows an equivalent distance of total planned road length (or planned travel time) to be more spatially dispersed over the contract region. Thus, the system provides better spatial diversity over a predetermined period of time, such as a session. For example, rather than assigning a polygon to a vehicle that attempts to drive all (e.g., 100%) roads within a particular polygon/census tract, the system assigns road segments to vehicles to enable the environmental data to be collected over a smaller percentage of roads across a much larger area. The system collects more spatially dispersed environmental data thereby resulting in better coverage over the entire geographic region being monitored.

Collecting environmental data based on the assignment of OSM ways includes assigning each OSM way a pass count based on the count of passes for which environmental data has been collected (e.g., over a predefined period of time, such as a month, year, or contract length, etc.) on the road segment(s) for the OSM ways. In some embodiments, the system randomly selects a road segment(s) for which environmental data is to be collected. As an example, the selection of the road segment(s) is selected randomly with a probabilistic weight that is proportional to the pass count for the corresponding road segment/OSM way. The weighting of the road segments is assigned so that the OSM way having a lowest corresponding pass count (e.g., a lowest number of data points in the historical environmental data) is the most likely to be selected.

In response to randomly selecting the road segments for which the environmental data is to be collected during a set of sessions (e.g., by a set of vehicles over a particular day), the system groups the road segments into a number of groups equal to the number of sessions in the set of sessions (e.g., so that each session has a corresponding group of sessions). The system performs the grouping of the road segments based on a clustering method. As an example, the clustering method is a K-means clustering.

For each group of road segments, the system orders the road segments in an efficient manner to optimize the travel time for environmental data collection. In some embodiments, the ordering of the road segments for a particular session is based at least in part on one or more of (a) a posted speed limit for the road segment(s), (b) an average speed limit for the road segment(s) (e.g., at the time of day the vehicle is expected to travel the road segment), (c) a current speed limit for the road segment(s), and/or (d) an indication that the road segment includes a construction zone, a hazard, an accident, etc.

Collection of environmental data by selecting polygons (e.g., census tracts) and directing vehicles to drive all or most of the road segments within the selected polygons during a corresponding session can result in spatial artifacts caused because a subset of areas of the geographic region corresponding to the polygons in which evaluation data is collected may be oversampled, and a subset of areas of the geographic region may be under sampled. To improve the spatial diversity of evaluation data sampling in the geographic region, the system may select and assign certain road segments for a session to ensure that a smaller percentage of road segments are driven in any one polygon/census tract, but a larger percentage of polygons/census tracts are sampled (e.g., through driving a subset of road segments within more polygons). However, the selection, grouping, and ordering of the road segments for collection of evaluation data during a set of sessions can still be inefficient. Although the process improves the spatial variance in sampled locations across the geographic region (e.g., reduces/eliminates the spatial artifacts within the map of the geographic region populated with environmental data), both processes used to sample the geographic regions corresponding to maps 400 and 500, and the geographic regions corresponding to maps 450 and 550 may result in temporal artifacts. For example, both processes may oversample certain road segments at certain times of day and under sample other road segments at certain times of day.

In the example shown, in FIG. 4B, map 450 illustrates the sampling of environmental data during a session based on selection of specific road segments. As illustrated, the sampling along the set of road segments performed during the session provides a good spatial diversity of air quality measurements. In the example shown in FIG. 5B, map 550 provides a representation of a simulated sampling over the geographic region during 19 driving days. Map 550 illustrates a very high spatial diversity among air quality measurements relative to map 500.

Some related art systems constrain the selection road segments or target regions to ensure that each road segment/target region is sampled at least a threshold number of times, such as twenty times (e.g., to ensure the pass count of the vehicle along the road segment is equal to at least twenty). However, the use of the threshold number of times to constrain the sampling of different road segments/target regions in the geographic region may be inefficient. For example, in some locations, twenty passes over a road segment may not be sufficient to provide a good representation of the road segment location. In other locations, twenty passes over a road segment may be more than is required to provide a good representation of the road segment location.

In some embodiments, for each road segment or target region within a geographic region, the system determines a frequency according to which the road segment/target region is to be sampled. The system may determine the frequency based on a determination of an extent to which recent environmental data samples (e.g., samples that were collected within a predefined time period) match historical environmental data samples. The system thus intelligently determines an extent to which each location in the geographic region is to be sampled to provide a good representation of the geographic region. The system uses the determined frequencies in connection with selecting locations to be sampled during a particular session (e.g., to sample the various locations in the geographic region in a manner that provides a good representation of the geographic region over a collection of sessions).

In some embodiments, the system determines the granularity (e.g., how finely or coarsely) with which certain locations/target regions within the geographic region (e.g., the contracted area) are to be sampled based at least in part on the variance of prior air quality measurements taken at locations within the vicinity of region. If the system determines that an expected difference between measurements in a set of adjacent roads or a set of road segments within a predefined proximity is less than a predefined threshold, the system determines to more coarsely sample the corresponding location (e.g., the data from the sampled road segment may be used as a good representation of adjacent roads or road segments within the predefined proximity). Conversely, if the system determines that an expected difference between measurements in a set of adjacent roads or a set of road segments within a predefined proximity is greater than a predefined threshold, the system determines to more finely sample the corresponding location (e.g., because the sampled data for one road is not a sufficiently good representation of an adjacent road or road segment within the predefined proximity, the system may collect more samples for that location, such as by sampling adjacent roads).

Figure 6A:
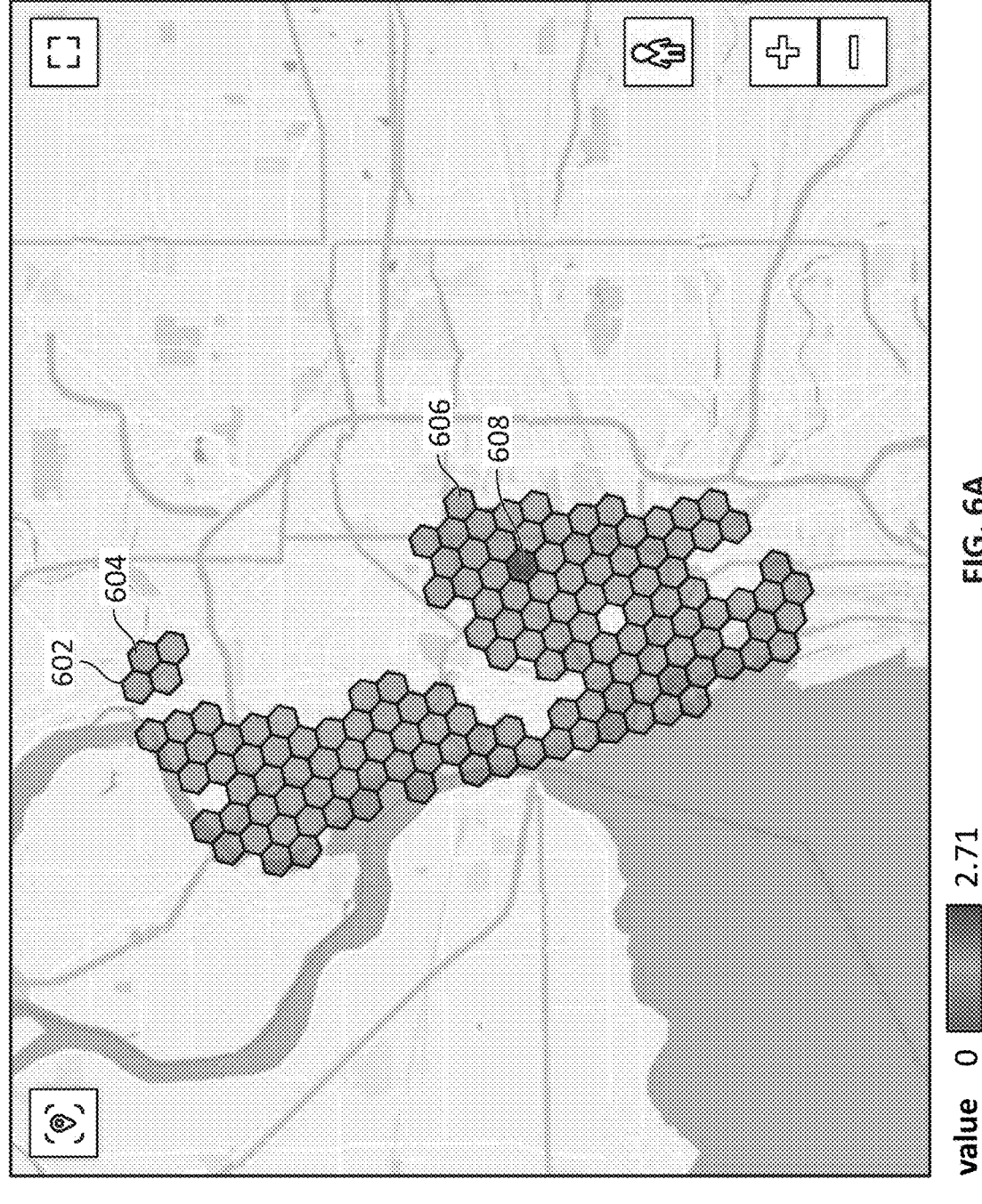
FIG. 6A illustrates an example of partitioning of a geographic region into a plurality of hexagons according to various embodiments.
Figure 6B:
FIG. 6B illustrates an example of further partitioning of a larger hexagon in a geographic region according to various embodiments.
Figure 6C:
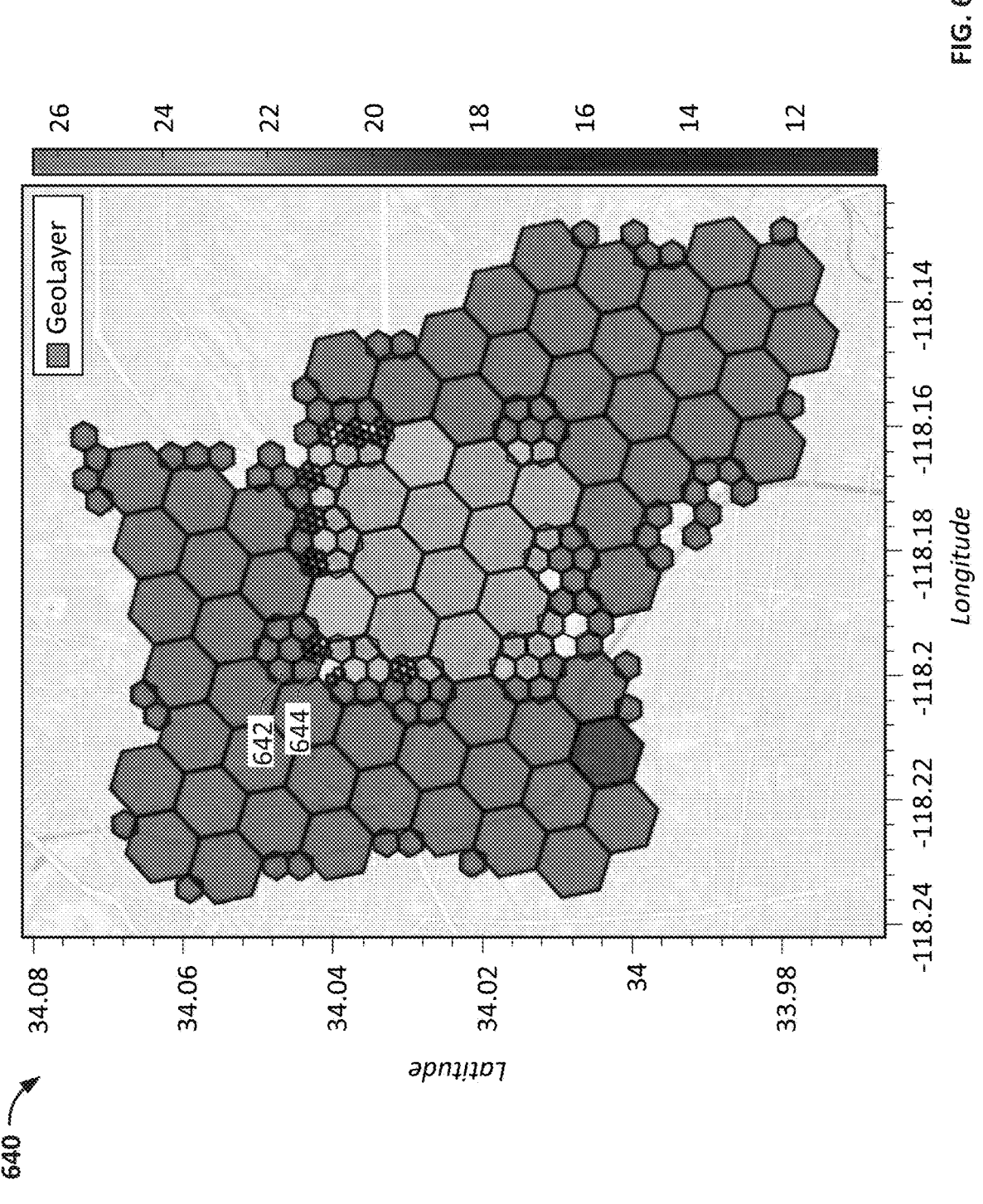
FIG. 6C illustrates an example of a map of hexagonal regions within a larger geographic region with an overlay of measured air quality according to various embodiments.
Figure 6D:
FIG. 6D illustrates an example of determining hexagonal areas based at least in part on the grouping of smaller hexagons or partitioning of larger hexagons according to a variance in air quality measurements according to various embodiments.

FIG. 6A illustrates an example of partitioning of a geographic region into a plurality of hexagons according to various embodiments. FIG. 6B illustrates an example of further partitioning of a larger hexagon in a geographic region according to various embodiments. FIG. 6C illustrates an example of a map of hexagonal regions within a larger geographic region with an overlay of measured air quality according to various embodiments. FIG. 6D illustrates an example of determining hexagonal areas based at least in part on the grouping of smaller hexagons or partitioning of larger hexagons according to a variance in air quality measurements according to various embodiments.

The system determines plans for collecting air quality measurements during a set of sessions in a manner that balances efficiency (e.g., driving time/distance efficiency) and global data quality.

In some embodiments, the system uses a variable resolution hexagon grid to facilitate air-quality characterizations that guide collection decision making. The system determines respective sizes of the hexagons in the variable resolution hexagon grid based at least in part on a data quality measure, such as a spatial data variance of prior air quality measurements in the hexagons/geographic area. For areas within a geographic area having a data variance (e.g., of prior air quality measurements in a historical dataset or over a predetermined amount of time) that is within a data variance threshold, the system determines to use a larger hexagon(s) for the area because a measurement from a location within the hexagon is a sufficiently accurate representation for the entire area comprised in the hexagon. For areas within a geographic area having a data variance that is greater than a data variance threshold, the system determines to use a smaller hexagon(s) for the area to fit the hexagons to ensure that an air quality measurement at a particular location within the hexagon is a sufficiently accurate representation of the air quality for the area comprised in the hexagon.

Related art systems select road segments to be travelled during a session. However, road segments are typically around one hundred meters in length. If the geographic region (e.g., the contracted area) is sufficiently large, the number of road segments to analyze and select in an optimal manner (e.g., optimal for data diversity) is too large for an optimization problem to be computationally solved (e.g., within a predetermined or reasonable amount of time). Various embodiments provide a data-driven method for dividing the geographic region into smaller regions (e.g., a plurality of hexagons of different sizes) such that the regions are appropriately sized to ensure a data resolution sufficient to provide a good representation of the region. In many cases, the system may not need to collect data at a one-hundred-meter resolution. For example, air quality may be the same over a one kilometer-long street. As another example, in a neighborhood, air quality on one street may be the same as its neighboring streets. For areas in which the required resolution is not very fine, attempting to sample (e.g., drive) every single street in a region results in an inefficient sampling (e.g., many streets within the region have to be driven multiple times to ensure that each street is driven once).

In the example shown in FIG. 6A, map 600 provides a representation of a geographic region partitioned/split into a plurality of hexagons, such as hexagons 602, 604, 606, and 608. In some embodiments, map 600 comprises one or more indications of an air quality measurement characteristic. An example of the indication(s) is the hexagons may be differently shaded or colored based on a data quality measure, such as one or more of a pass count (e.g., the number of times the hexagon was sampled over a predetermined period of time), a methane concentration level, a temporal data variability, and/or a spatial data variability, a priority for selecting the hexagon as a target region (e.g., a measure of a need to sample the hexagon to provide a good representation across the geographic region), etc. For example, hexagons 606 and 608 may have different shadings/coloring. Hexagon 606 may be shaded green and hexagon 608 may be shaded red.

In some embodiments, the partitioning or sizing of the regions (e.g., the hexagons) is based at least in part on spatial data variability, and the selection of the target regions is based at least in part on the temporal data variability. Generally, the system has a preference to partition the geographic region into larger hexagons because air quality sampling is more efficient (e.g., a smaller number of regions need to be visited for sampling), which may be subject to the flattening process of determining an aggregate partitioning layer for a plurality of partitioning layers respectively corresponding to a plurality of pollutants or other characteristics being measured. The system determines how frequently a particular region (e.g., hexagon) is to be sampled based on a temporal data variability.

The system divides the geographic region into a plurality of hexagons. In connection with determining the target regions (e.g., a subset of the plurality of hexagons) to be visited during a session, the system aggregates the data (e.g., the prior air quality measurements) within each region and uses the data within a region to perform a statistical analysis (e.g., to obtain statistical information for the air quality data within the region). The system uses the statistical analysis to partition/size the regions into the plurality of hexagons and to assign priorities for selection of target regions to be assigned to a session.

In the example shown in FIG. 6B, map 620 illustrates the splitting of certain hexagons into a plurality of hexagons (e.g., seven equally-sized smaller hexagons). Each day the system may determine a sizing of the hexagons within the geographic region. For example, the system may first partition the geographic region into a set of equally sized hexagons, and then for each hexagon within the set of equally sized hexagons determines whether to further partition the particular hexagon into seven equally-sized smaller hexagons, or whether to group the particular hexagon with other hexagons to obtain a larger hexagon. For each hexagon in the geographic region, such as hexagons, 622, 624, 626, and 630, the system determines whether to split the hexagons into a plurality of hexagons. The system may determine whether to split the hexagons into a set of smaller hexagons based at least in part on an extent to which the environmental data across the hexagon is similar (e.g., a spatial data variance for the hexagon). In the event that the system determines that the extent of the similarity of the environmental data (e.g., an environmental data similarity) across the hexagon is less than a predefined similarity threshold, the system determines to partition the hexagons into a set of smaller hexagons. In the example shown, hexagon 630 is partitioned into a set of smaller hexagons, such as 632, 634, 635, and 636. In some embodiments, the system further determines whether to partition the hexagons into still smaller hexagons. The system may continue to determine whether to partition or group hexagons and the smaller hexagons formed by partitioning the hexagons, until the defined hexagons each have an environmental data similarity that satisfies a predefined criteria (e.g., has at least a minimum level of similarity). For example, as illustrated, smaller hexagon 635 partitioned from hexagon 630 is still further partitioned into a set of smaller hexagons.

In the example shown in FIG. 6C, the system determines whether to group a set of equally-sized hexagons into a larger hexagon. Map 640 comprises a geographic region that is split in to various size hexagons. The system determines the data quality for the hexagons, such as a spatial data variance, and determines the sizing (e.g., whether to further partition or group the hexagons). As illustrated, the system determines whether to group the smaller hexagons within the boundary defined by larger hexagon 642. Although most hexagons within larger hexagon 642 may have a similar data quality measure, the smaller hexagons within medium-sized hexagon 644 may have sufficient variability to cause the system to deem the grouping of the hexagons into larger hexagon 642 suboptimal. The system uses smaller hexagons to better match the straight lines between two different air quality regions (e.g., air quality regions having different levels of data quality measures or environmental data characteristics). This matching of straight lines between the two different air quality regions forces more driving along the boundary of the two regions because the vehicle generally "zigs and zags" more when sampling smaller hexagons.

The sizing of the regions (e.g., hexagons) to divide the geographic region into regions of similar air quality properties (e.g., regions having a small spatial data variance in prior air quality measurements) takes advantage of the priorities of hexagons that seven equally-sized hexagons can be grouped to form a larger hexagon, or a larger hexagon can be split into seven equally-sized hexagons. Accordingly, the system determines the sizing of the regions by grouping or splitting hexagons, such as based on a statistical analysis of data collected within the areas defined by the hexagons. The sizing of the regions includes obtaining a historical air quality data set, aggregating data, and performing a statistical analysis on the data to identify a spatial data variance, a temporal data variance, an extent to which recent air quality measurements match historical air quality measurements, etc. In some embodiments, the system sizes the region to group areas that have closely matching air quality measurements. For example, the system sizes the region to ensure that an air quality measurement taken at a particular location within the region is a sufficiently good representation of the entire area comprised in the region. If the difference between air quality measurements between different areas is less than a predefined threshold, the system attempts to collect the areas into a single region (e.g., subject to the constraint that a region is a hexagonal shape and can be formed by grouping seven equally-sized smaller hexagons or partitioning a larger hexagon into seven equally-sized smaller hexagons).

In the example shown in FIG. 6D, map 660 illustrates a geographic region partitioned into hexagons of various sizes. The hexagons may be shaded or color-coded based on data quality measures, such as a pass count or a priority associated with sampling the corresponding hexagon. As an example, the hexagons may be colored by priority. As another example, the hexagons may be colored by time of day to visit (e.g., a time-window constraint associated with the hexagon). The system may generate various layers of color-coding of the hexagons within the geographic region.

The system uses the statistical information in connection with determining the target regions for a particular session. For example, the system assigns priorities to the regions based at least in part on the statistical information. In some embodiments, the system selects the target regions based at least in part on a temporal data variability of prior air quality measurements within the various target regions. The system may determine an extent to which recent sampling for a particular hexagon matches (e.g., is within a predefined similarity threshold) historical air quality measurements for the area defined by the hexagon and based on the extent to which the recent sampling and historical air quality measurements match, the system determines whether additional sampling should be performed in order to provide a good representation of the current air quality measurements across the hexagon, or more broadly the geographic region.

The priority may be assigned based at least in part on a determination of hexagons that are adequately represented in the prior air quality measurements, or a determination of hexagons that are not adequately represented in the prior air quality measurements. For example, the statistical information includes an indication of an extent to which a recent air quality measurement for a particular hexagon matches historical air quality measurements. If there is a big/significant change between a recent air quality measurement for a hexagon and the historical air quality measurements for the hexagon, the statistical information may be indicative that there is a phenomena taking place (e.g., a gas leak) that is causing the recent air quality measurements to not match the historical air quality measurements. Accordingly, the system determines that there is a need to further sample the hexagon to monitor the phenomena and assigns a relatively higher priority to the hexagon. If there is not a significant change between the recent air quality measurement for a hexagon and the historical air quality measurements for the hexagon (e.g., the recent sampling data closely matches the historical sampling data), the system may deem the hexagon to be sufficiently represented in the historical air quality measurement data set relative to other hexagons and thus assign a relatively lower priority to the hexagon (e.g., indicating that there is not a great need for the hexagon to be sampled).

The system randomly selects the target regions from the plurality of hexagons based on a weighting of the respective hexagons according to their assigned priorities (e.g., higher priority hexagons are weighted more heavily than lower priority hexagons). Accordingly, the random selection is biased to select those hexagons having a higher priority.

In some embodiments, the system randomly selects a set of target regions to be sampled over a set of sessions (e.g., to a set of vehicles to drive for a particular day). The set of target regions may be randomly selected in a manner that the selection algorithm is biased to selecting regions (e.g., hexagons) for which the data collection is more highly needed/desired. For example, the selection algorithm includes weighting the regions according to an assigned priority indicative of the need for more data within the region. To assign subsets of the target regions to a particular session, the system may perform a clustering (e.g., using K-means clustering) to group geographically close target regions. For each session (e.g., each day of driving for a vehicle with mounted mobile sensors for air quality measurement collection), the system selects a set of target regions to be sampled during the session subject to session constraints such as total drive time, total distance, etc. The target regions for a particular session may be selected based at least in part on the clustering of regions. Additionally or alternatively, the system may also select target regions based on the feasibility of driving time such as in order to select the most total sum priority across hexagons that are feasibly drivable during a session (e.g., a drive session or a driver's shift).

In response to selecting the target regions to be assigned to a session, the system determines locations at which the air quality is to be sampled within each of the target regions. For example, the system selects a single location within each of the assigned target regions. The locations may be randomly selected based on an equal weighting of road segments or particular locations within the region, or alternatively, based on an assignment of weightings to road segments/locations. The weightings for road segments or locations may be assigned based on one or more of (i) the pass count (e.g., the number of samplings within over a predefined time period) for the location or within a predefined distance threshold of the location, (ii) a data quality measure for the road segment or location, such as the spatial diversity of historical air quality measurements in the hexagon, (iii) a methane leak probability for the road segment or location, (iv) a BTEX (benzene, toluene, ethylbenzene and xylene) source probability for the road segment or location, etc.

After the system determines the target regions to be assigned to a particular session and the specific locations (e.g., target locations) to be sampled within each of the assigned target regions, the system determines (e.g., generates) a plan (e.g., a drive plan) for deployment of an air quality measurement system during the session. Generating the plan includes determining a time window in which each of the target regions are to be sampled. Certain target regions may have associated time-window constraints that are determined based on a temporal data variance (e.g., to impose a time diversity of air quality measurement samples). The system generates the plan according to such time-window constraints. Additionally, generating the plan includes determining a route based on a balancing of both (i) the pass counts for the various locations sampled during the session, and (ii) impact to travel time by directing the air quality measurement along a particular route. As an example, the system attempts to generate the plan to ensure that the air quality measurement system is able to complete as many waypoints as possible (e.g., sample a largest number of locations) while ensuring suitable pass coverage. As noted above, suitable pass coverage may be determined on a region-by-region basis or even more granularly as a road segment-by-road segment basis.

The system orders the target regions to create an efficient plan to avoid causing the air quality measurement system to travel far (e.g., greater than a predetermined distance or time threshold) out of the way (e.g., from a current or subsequent target region). If the system determines that a target region that is far out of the way is to be sampled during the session, the system selects road segments according to a determination of priorities for collecting air quality measurements that ensure a good representation of the geographic region (e.g., ensuring spatio and temporal diversity). In some implementations, if the system identifies a target region that is far out of the way or that introduces an inefficiency greater than a predetermined threshold (e.g., causes the travel time to increase by a predetermined time threshold), the system weighs the costs and benefits of sampling the target region. For example, if the need to sample the target region is not very high (e.g., the target region has a relative low priority) such as because it is pretty well characterized by the prior air quality measurements, then the system de-prioritizes the target region.

The locations for the ordered target are geographically spaced apart. Thus, in order to collect air quality measurements at the locations, the air quality management system (e.g., the vehicle) travels a path from one location to the next until the session is complete. As a result, the travelling between locations enables the air quality management system to additionally collect air quality measurements at locations (e.g., road segments) along the travel path. The path may be comprised of a plurality of road segments. In some embodiments, the system intelligently selects the road segments to be traveled during the session to enable collection of air quality measurement samples along road segments that best improve the data representation across the geographic region. For example, the system identifies road segments corresponding to locations for which air quality measurements were last collected more than a predefined time period and prioritizes selection (e.g., associates weightings used in a random selection process) of such road segments over other road segments that have good data representation. Further examples of road segments that the system may identify and prioritize (e.g., associate a larger weighting) include: (a) road segments for which recent air quality measurements do not closely match the historical air quality measurements, (b) road segments for which prior air quality measurement collections have been clustered around one or more times of day such that there are certain other times of day that have few or no samples to provide sufficient temporal diversity of data points at the location/area, (c) road segments corresponding to locations at which a methane leak is recently detected (e.g., within a predetermined amount of time), (d) road segments corresponding to locations at which a BTEX signal is recently detected, (e) road segments corresponding to locations at which a TVOC (total volatile organic compounds) signal is recently detected, etc.

Related art systems in which the route to/between locations is driver-determined generally have artifacts that arise because individuals tend to drive the same roads to get from one area to another. The individual drivers may be biased to select the fastest route or a familiar route. As a result, such related art systems generally do not provide a good data diversity.

Other related art systems may implement a turn-by-turn route planning process. Related art route planning processes are optimized for travel time or distance. Thus, the related art route planning processes are biased towards directing the vehicle to travel highways or roads with high posted speed limits, or little traffic. For example, the related art route planning process establishes and solves a shortest path problem based on the nodes to be visited. As a result, such related art systems generally do not provide a good data diversity.

In contrast, according to various embodiments, the system selects the path based at least in part on a consideration of locations/road segments at which collection of air quality measurements would improve the model/representation across the geographic region. For example, the system establishes a graph traversal problem in which the nodes correspond to the selected locations in the target regions associated to the path. The system determines the edges (e.g., road segments) connecting the nodes. The system associates weights to the various edges within the graph (e.g., the geographic region) and may determine the solution to the graph problem (e.g., select the road segments) based at least in part on the weights. The weights can be used to bias the selection of road segments to achieve desired goals (e.g., good data diversity, collection at areas identified to be important or in need of further sampling, etc.). The system may constrain the graph traversal problem with a maximum travel time (e.g., to ensure that all locations are visited during the session) and/or a maximum travel distance.

In some embodiments, in connection with determining the path (e.g., the road segments) to travel during the session, the system may weight various locations/road segments based on pass count and/or expected travel time. The process for determining the path is configured to attempt to achieve good coverage across the road segments. In some embodiments, the process for determining the path is biased to weigh the pass counts for the road segments more heavily than the travel time. The system may randomly select the path based at least in part on the weightings for pass count and/or travel time. In response to selecting the path, the system updates a plan (e.g., a driving plan) that is provided to an air quality measurement system (e.g., a vehicle). The plan provides turn-by-turn guidance to the driver to direct the air quality measurement system across the selected path and to each of the target locations.

In some embodiments, the system updates (e.g., dynamically updates) the path/plan substantially in real-time in response to determining that the vehicle has strayed from the turn-by-turn guidance (e.g., if the driver turned at a different street or in a different direction). As an example, the system updates the path/plan to direct the vehicle along road segments that take the vehicle back towards the initial path/plan. As another example, the system re-computes a solution to the graph traversal problem (e.g., for the remaining target locations) and updates the plan with the new path for the remaining portion of the session.

Additionally, the system may select target regions to be assigned to a particular session based on a temporal data variance of the prior air quality measurements for the target regions. The system can select the target regions to optimize for temporal diversity of sampling (e.g., to prevent a bias towards sampling a particular target region at the same time of day every day).

Figure 7:
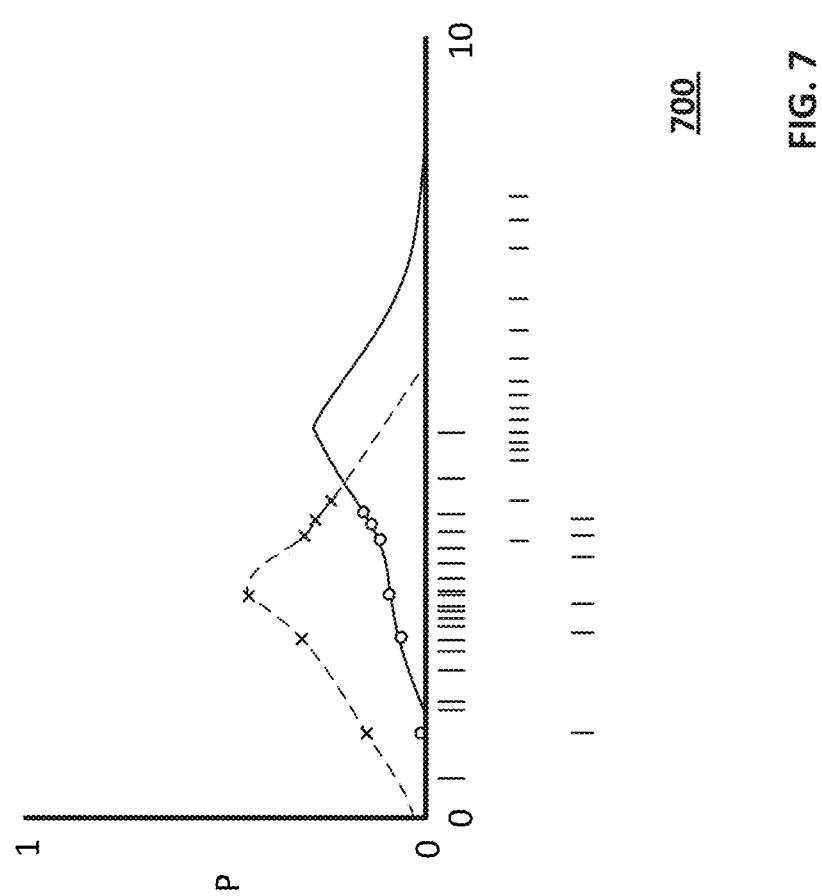
FIG. 7 illustrates a probability distribution for air quality measurements in different target regions according to various embodiments.

FIG. 7 illustrates a probability distribution for air quality measurements in different target regions according to various embodiments. Graph 700 illustrates a characterization of various hexagons. The hexagon characterization may be calculated using a likelihood function, which assumes a normal distribution of measurements. The likelihood function may be represented as in Equation (1), where P is the likelihood, pdf the probability density function of the sample of measurements, $\mu$ represents the mean of the sample of measurements, and $\sigma$ represents the standard deviation of the sample of measurements.

$$P(x_i) = pdf_{\mu,\sigma}(x_i) \tag{1}$$

Figure 8:
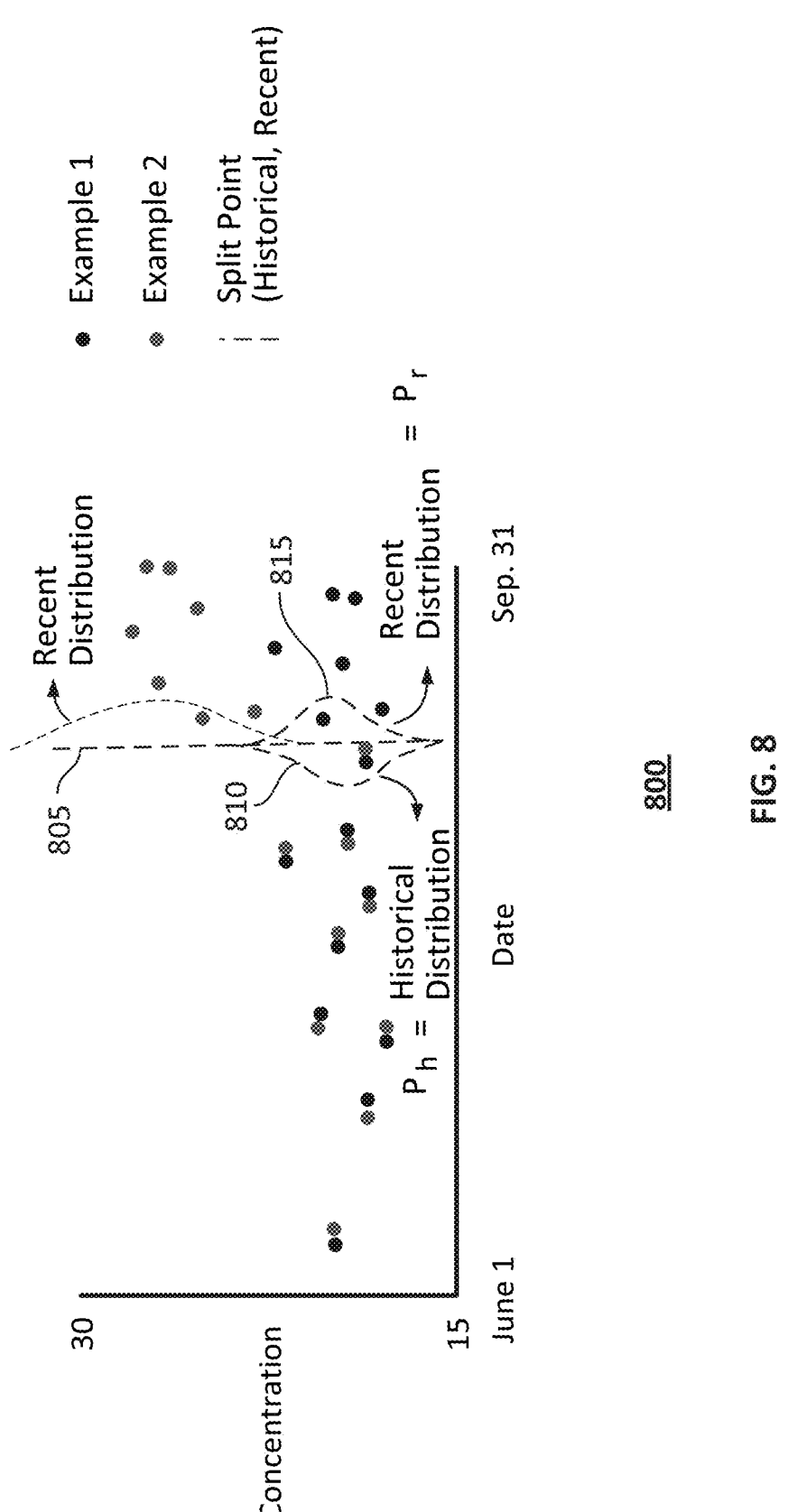
FIG. 8 illustrates a probability distribution for air quality measurements in a particular target region over time according to various embodiments.

FIG. 8 illustrates a probability distribution for air quality measurements in a particular target region over time according to various embodiments. The system uses graph 800 in connection with prioritizing regions (e.g., hexagons) on a particular day/session. Graph 800 illustrates a probability distribution with a split point 805 between historical and recent air quality measurements. The split point may be determined based on deeming samples collected more than a predetermined time threshold as being historical. The predetermined time threshold may be configurable. The system determines a historical sampling distribution 810 for the first example data and a recent sampling distribution 815 for the first example of data. Historical sampling distribution 810 is a distribution of the air quality measurements (e.g., concentration of a particular target contaminant) for samples collected before split point 805 (e.g., samples provided on the left of split point 805). Similarly, recent sampling distribution 815 is a distribution of air quality measurements for samples collected after split point 805 (e.g., samples provided on the right of split point 805).

In some embodiments, the system prioritizes a target region based at least in part on the historical sampling distribution and the recent sampling distribution. In some embodiments, the system determines a prioritization for a particular target region based on a ratio of (i) the probability of a first predefined percentage of most recent data, given a calculated mean and standard deviation of a second predefined percentage of historical data; over (ii) the probability of the first predefined percentage of most recent data given the computed mean and standard deviation of the first predefined percentage of most recent data. As an example, the first predefined percentage of most recent data is ten percent, and the second predefined percentage of historical data is ninety percent.

Figure 9A:
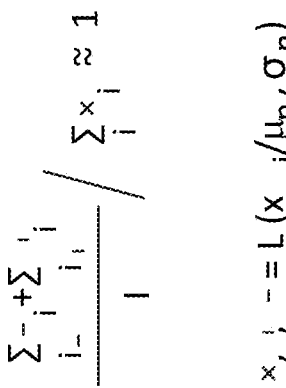
FIGS. 9A and 9B illustrate example probability distributions for air quality measurements in different overlapping target regions according to various embodiments.
Figure 9A:
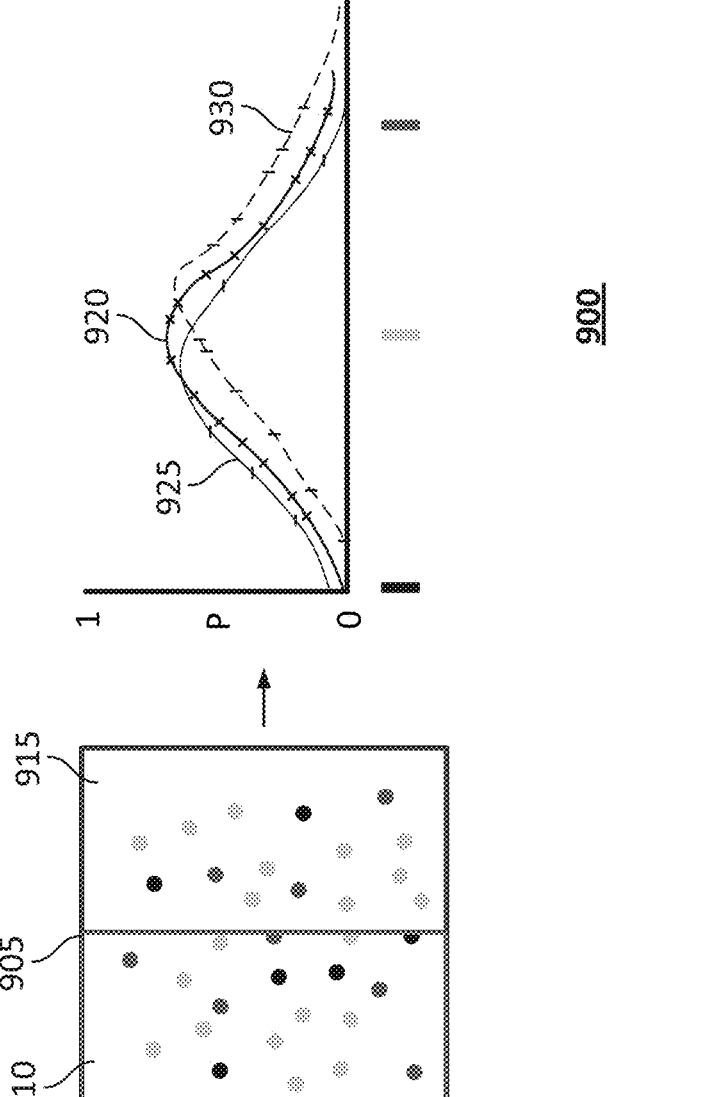
Figure 9B:
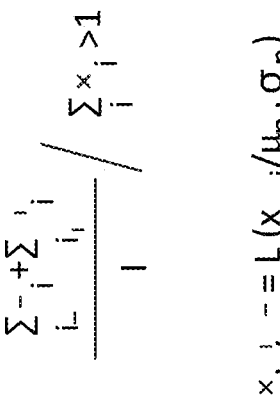
Figure 9B:
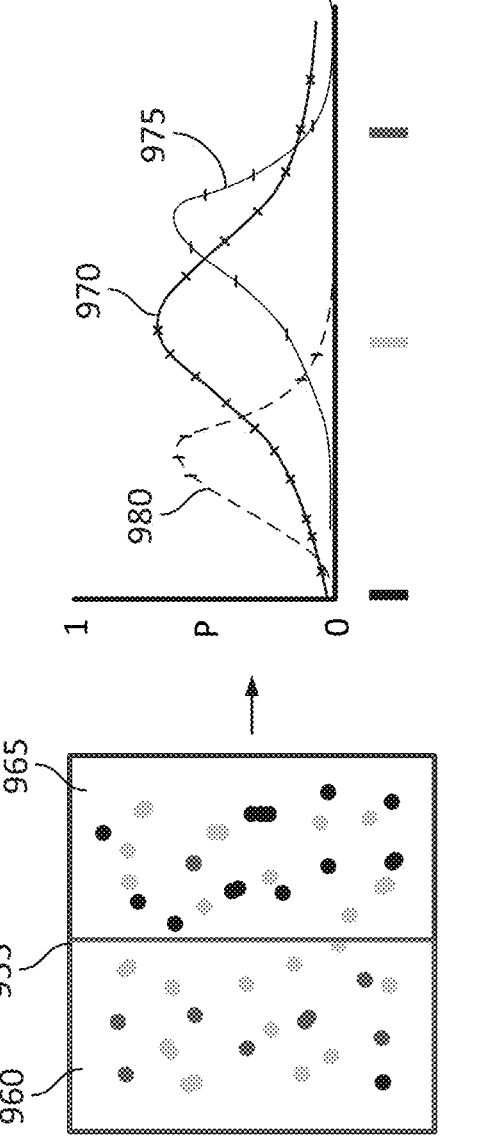

FIGS. 9A and 9B illustrate example probability distributions for air quality measurements in different overlapping target regions according to various embodiments.

In the example shown, graph 900 illustrates probability distributions for overlapping regions of varying granularity. For example, the illustrated probability distributions 920, 925, and 930 respectively correspond to regions 905, 910, and 915. The system uses the probability distributions in connection with determining a sizing for the regions (e.g., the hexagons). If the probability distributions are within a predetermined similarity threshold, the system determines to group the regions. For example, the system determines whether to combine regions 910 and 915 into a single larger region 905 based on the extent to which each of their respective probability distributions (e.g., probability distributions 925 and 930) differ from (or is similar to) the probability distribution for the single larger region 905 (e.g., probability distribution 920).

In some embodiments, the system determines to merge a set of smaller regions (e.g., finer regions) based on the ratio between the likelihood of the observed data given subclassification in the smaller regions is not substantially different than the likelihood of the observed data assuming that all the observed data comes from one larger hexagon. In some embodiments, if the ratio is between 0.85 and 1.15, the system determines to merge the set of smaller regions to a larger/coarse region. Various other thresholds can be implemented to determine whether to merge the set of smaller regions to a larger/coarse region.

Similarly, in the example shown, graph 950 illustrates probability distributions for overlapping regions of varying granularity (e.g., based on a different data set). For example, the illustrated probability distributions 970, 975, and 980 respectively correspond to regions 955, 960, and 965. The system uses the probability distributions in connection with determining a sizing for the regions (e.g., the hexagons). If the probability distributions do not closely match (e.g., are not within a predetermined similarity threshold), the system determines not to group the regions. For example, the system determines whether to combine region 960 and 965 into a single larger region 955 based on the extent to which each of their respective probability distributions (e.g., probability distributions 975 and 980) differ from (or is similar to) the probability distribution for the single larger region 955 (e.g., probability distribution 970).

In some embodiments, the system determines to split/partition a larger/coarser region into a set of smaller regions (e.g., finer regions) if the ratio between the likelihood of the observed data given sub-classification in the smaller regions is substantially different than the likelihood of the observed data assuming that all the observed data comes from one larger hexagon. In some embodiments, if the ratio is less than about 0.65 or greater than about 1.35, the system determines to partition the larger/coarse region into a set of smaller regions.

Graphs 900 and 950 depict contrasting similarities between probability distributions. Probability distribution 920 for the single larger region closely matches both probability distributions 925, 930. Accordingly, the system determines to group regions 910, 915 into a single larger region 905. In contrast, probability distribution 970 for the single larger region is substantially different from both probability distributions 975, 980. Accordingly, the system determines not to group regions 960, 965 into single larger region 955.

Although the foregoing examples are described in connection with the determining of whether to group the regions (e.g., regions 910 and 915, and regions 960 and 965), a similar analysis can be performed in connection with determining whether to split a region into a plurality of smaller regions, such as whether to split region 905 into regions 910, 915, or whether to split region 955 into regions 960, 965.

Figure 10A:
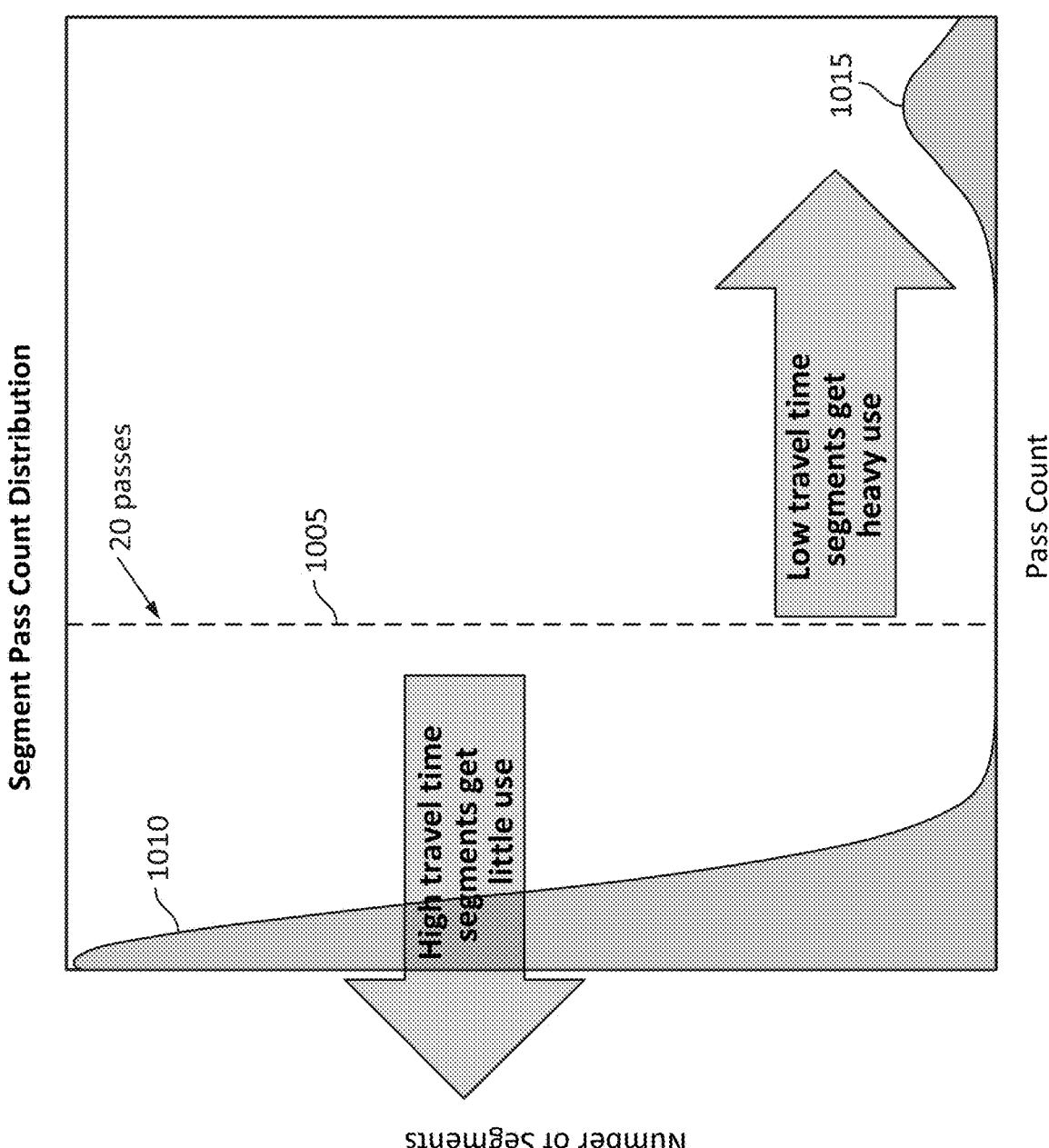
FIGS. 10A and 10B illustrate distributions of segment pass count distributions according to various embodiments.
Figure 10B:
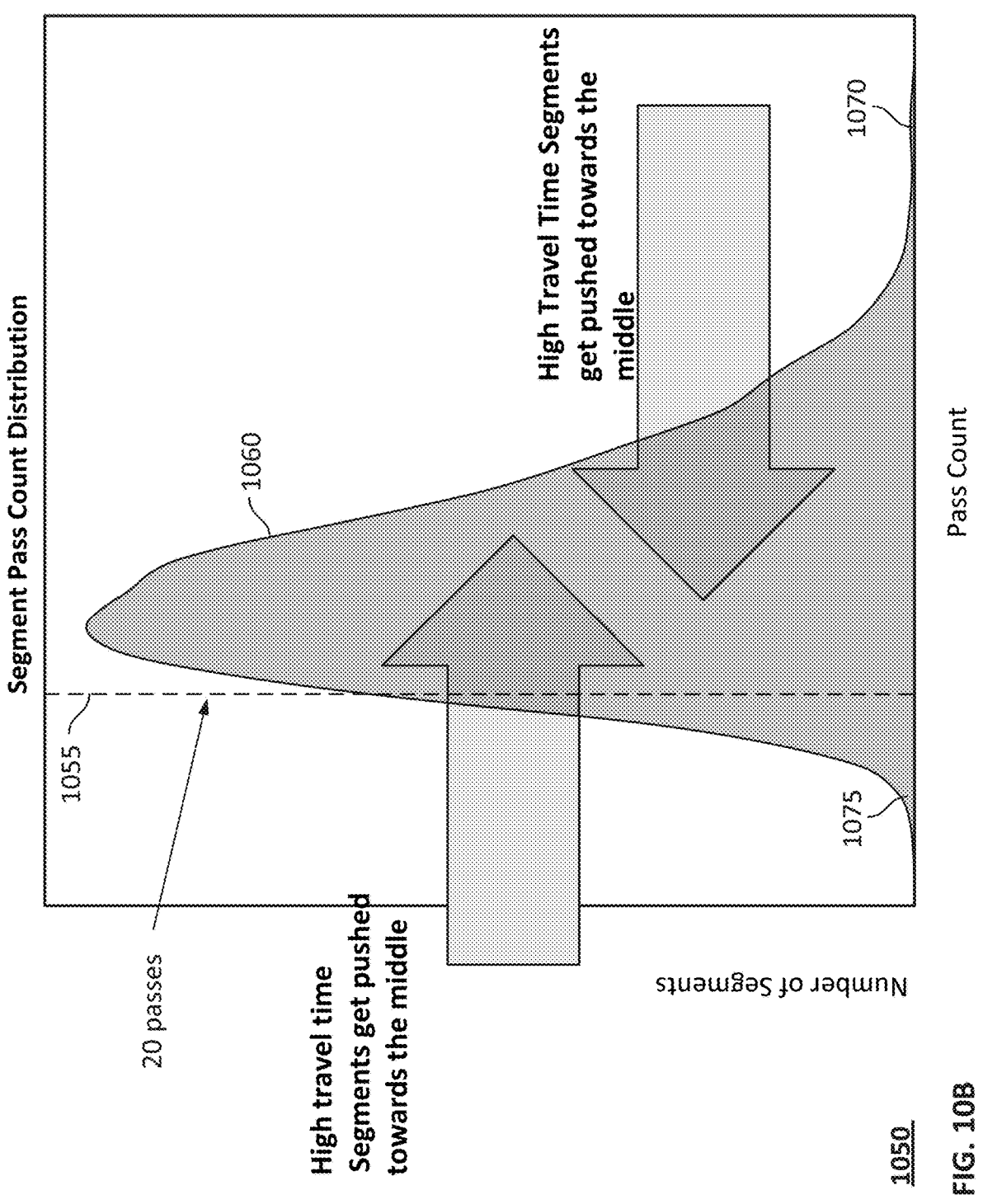

FIGS. 10A and 10B illustrate distributions of segment pass count distributions according to various embodiments.

In the example shown, graph 1000 illustrates a segment pass count distribution. Related art systems generally used the constraint that the system was to attempt to obtain twenty passes for each road segment in the geographic region. Accordingly, for illustrative purposes, graph 1000 includes an indicator 1005 of a pass count equal to twenty passes. As illustrated, the segment pass count distribution has peaks 1010, 1015. Peak 1010 shows that a significant number of the road segments have a relatively small number of pass counts (e.g., significantly less than twenty passes). The road segments under peak 1010 may correspond to road segments that have a relatively high travel time (e.g., have road segments that have low posted speed limits, heavy congestion, etc.). Peak 1015 shows that a relatively significant number of road segments have high pass counts. The road segments under peak 1015 may be those road segments that individuals or related art routing processes are biased. For example, the road segments under peak 1015 may correspond to low travel time segments (e.g., road segments having high posted speed limits, low congestion, etc.). The segment pass count distribution illustrated in graph 1000 is suboptimal because it is illustrative that a relatively large subset of segments is sampled significantly more than another relatively large subset of segments.

In the example shown, graph 1050 illustrates a segment pass count distribution. The segment pass count distribution shows a higher concentration of segments having a similar pass count than the segment pass count distribution of graph 1000. Additionally, the number of pass counts are primary centered near indicator 1055 (e.g., indicating twenty pass counts). Tails 1070 and 1075 show that a relatively insignificant amount of segments have really low number of pass counts or a relatively high number of pass counts.

According to various embodiments, the system biases selection of target locations or road segments towards a segment pass count distribution similar to the segment pass count distribution shown in 1050. For example, high travel time segments are biased to be selected more than they otherwise would from an individual or related art routing process. Similarly, low travel time segments are biased to be selected less than they otherwise would from an individual or related art routing process (e.g., which are optimized for travel time, etc.). The system biases the road segments to bring the center of the segment pass count distribution closer to a pass count near twenty passes. Weighting by pass count ensures good segment pass coverage with the drawback of high waypoint drop rates. In some embodiments, the system also provides a weighting by travel time to ensure a low waypoint drop rate at the expense of segment coverage. Thus, the system balances the desire for a predetermined threshold number of pass counts and a desire to minimize travel time (e.g., to allow more waypoints/target locations to be sampled during a session). The system implements a combined weighting scheme that exposes tunable parameters to allow a user or other system control the extent to which pass count and travel time are prioritized.

In some embodiments, the system determines target regions, target locations within the target regions, or edges (e.g., road segments to travel to/between target locations) based at least in part on methane data. The system processes the collected air quality measurements to obtain methane data, which may identify the extent to which methane is present. For example, the system uses the methane data to identify/detect methane leaks. The detection of a methane leak includes generating a map of average methane concentrations across the geographic region and identifying locations corresponding to a strong signal that methane is present in the area. Average methane concentrations are not expected to be very high (e.g., the system does not expect to observe methane signals everywhere). As a result, the actual observation of a methane presence (e.g., a methane signal stronger than a predetermined methane threshold) is a lot more informative.

In some embodiments, the system determines the plan for directing the air quality measurement system to target locations during a session based at least in part on whether the system detects a methane leak (or expected methane leak). In response to identifying a methane leak, the system determines to re-visit the location of the methane leak signal. For example, the system schedules a re-visit as fast as possible or within a predetermined amount of time. In some implementations, the system constrains the route planning problem to a requirement that a location of a detected methane leak is travelled during the session. In some implementations, the system uses the methane data to assign/adjust weightings of various regions (e.g., hexagons), target locations within the selected target regions, or road segments between target locations. The weightings based on methane data are used to bias the random selection of the region, target location, and/or road segment towards prioritizing or more frequently selecting a target location or road segment located at a detected methane leak.

In some embodiments, the system implements a sampling process that selects using statistical rigor target locations or road segments to be visited during a session. As an example, the system implements a Thompson sampling technique. The system implements such a sampling process/technique because methane is known to not be observed at a known methane leak during each sampling (e.g., each visit by the air quality measurement system). For example, weather, wind, system load, etc. may impact detection of methane leak signals during sampling.

The system may more heavily weight/prioritize detected methane leaks corresponding to stronger methane leak signals (e.g., higher detected methane concentrations) to cause locations with largest leaks to be sampled more preferentially.

In some embodiments, the system monitors a plurality of pollutants or characteristics over a geographic region. For example, the system samples and monitors the air quality over a particular region for a set of pollutants. Each pollutant may diffuse differently or occur at different locations within the geographic region. Accordingly, the air quality maps for different pollutants are not likely to appear the same. Because of the difference in the air quality maps for the various pollutants being measured/monitored, the system may determine an aggregated air quality map that is used to identify target regions to be sampled to avoid a bias in selecting target regions (e.g., a biasing towards any one particular pollutant(s) when determining a tiling of the geographic region). The system may implement a preference to monitor certain pollutants over other pollutants during the targeting process in which target regions or target locations are selected for sampling during a particular session(s).

In some embodiments, the system determines a partitioning of a geographic region for a session based at least in part on a set of partitionings for a corresponding set of pollutants or other characteristic to be measured.

In some embodiments, the system generates a partitioning layer of the geographic region for each pollutant to be measured/characterized. The partitioning layer may be generated in accordance with the partitioning method described in connection with FIGS. 6A-6D or process 1900 of FIG. 19, or process 2000 of FIG. 20. The system generates a partitioning layer (e.g., a variable resolution hexagon grid) of the geographic region for a particular pollutant (or other characteristic) based at least in part on a data quality measure. For example, the system generates the partitioning layer based at least in part on determining a spatial data variance of prior measurements for the particular pollutant. A partitioning layer may correspond to a map layer for a map of the geographic region (e.g., the contracted region or region over which air quality is to be measured/monitored).

In response to generating a partitioning layer for each pollutant/characteristics to be monitored, the system flattens the set of partitioning layers into a single aggregated partitioning layer. For example, the system determines an aggregated partitioning for a single partitioning layer (e.g., a map layer) that is to be implemented for the targeting regions (e.g., selection of target regions) to be sampled during a session. The aggregated partitioning layer comprises a variable-sized partitioned grid (e.g., variable resolution tiling) of the geographic region. For example, the aggregated partitioning layer comprises a variable-resolution hexagon grid. The aggregated partitioning layer is determined based at least in part on the set of partitioning layers generated for each of the pollutants (or other characteristics) to be monitored.

The use of the aggregated partitioning layer enables the system to consider a set of pollutants (e.g., each pollutant to be monitored) when identifying target regions that are to be sampled during a session (e.g., to reduce/minimize the bias towards monitoring a particular pollutant). The process for generating the aggregated partitioning layer includes, for each particular location over the geographic region (or a randomly selected set of locations), determining a resolution (e.g., tiling size) of the partitioning/tiling for the set of partitioning layers, and determining the resolution of the partitioning (e.g., the tiling or hexagon size) for the aggregated partitioning layer based on the resolution across the set of partitioning layers. In some embodiments, the system determines the resolution for a particular location on the aggregated partitioning layer based on selecting the smallest resolution for that location across the set of partitioning layers (e.g., the partitioning layers generated for each pollutant).

Figures 11A, 11B, 11C:
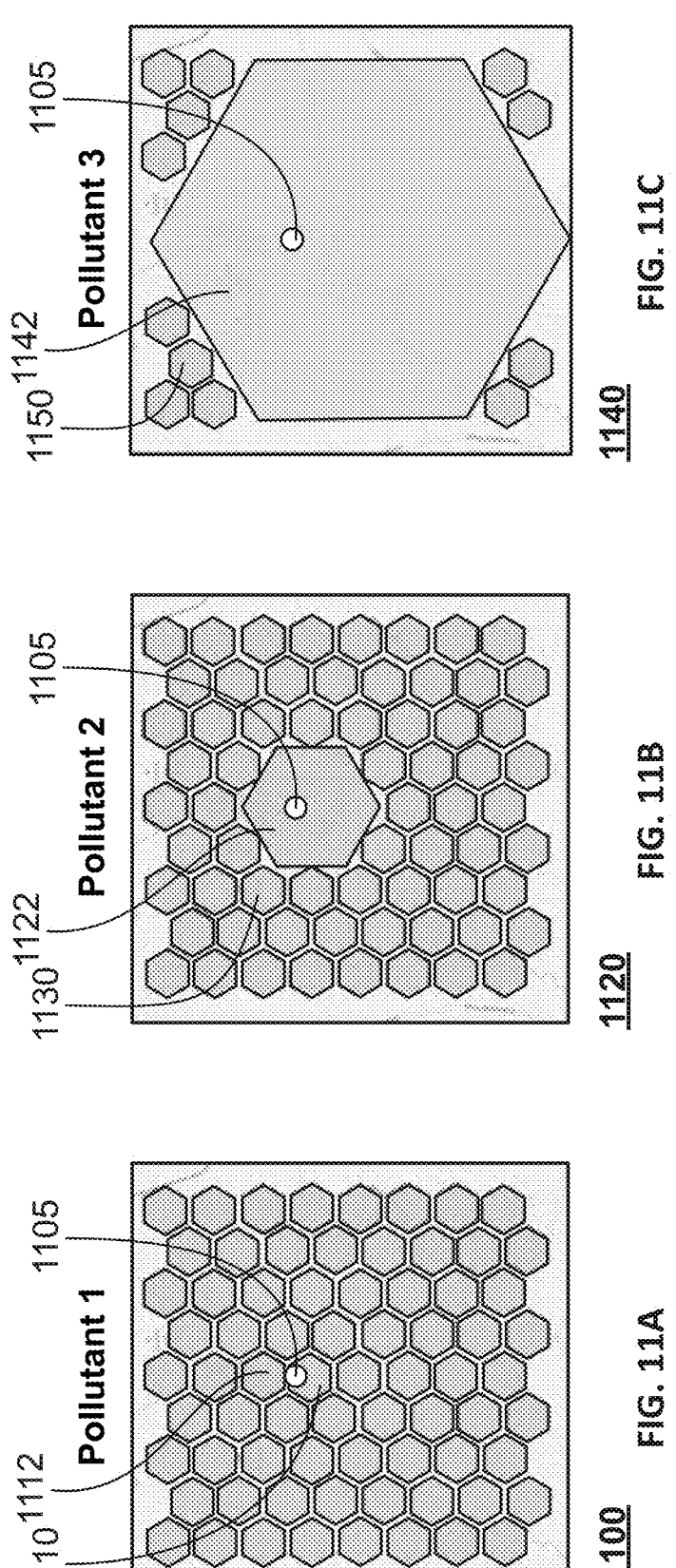
FIGS. 11A, 11B, and 11C illustrate partitions of a geographic region for different pollutants according to various embodiments.

FIGS. 11A, 11B, and 11C illustrate partitions of a geographic region for different pollutants according to various embodiments. In the examples shown, partitioning layers 1100, 1120, and 1140 are respectively generated for different pollutants. A partitioning layer is generated based on a data quality measure (e.g., a spatial data variance) for a corresponding pollution. The resolution of the partitioning (e.g., the tiling or size of the hexagon) at a particular location 1105 across the plurality of partitioning layers 1100, 1120, and 1140 can be used to generate the aggregate partitioning layer, such as aggregate partitioning layer 1160 of FIG. 11D.

Partitioning layer 1100 is generated for a first pollutant (e.g., Pollutant 1). As illustrated in FIG. 11A, the partitioning at location 1105 is relatively granular. For example, location 1105 is located within small-sized hexagon 1110. Similarly, neighboring hexagons, such as hexagon 1112, are relatively small. The partitioning at location 1105 may be relatively granular because the data quality measure of the first pollutant (e.g., a spatial data variance of prior measurements of the first pollutant levels) is highly differentiated (e.g., a spatial data variance greater than a first predetermined variability threshold). For example, the first pollutant levels in proximity to location 1105 has a relatively high spatial data variance.

Partitioning layer 1120 is generated for a second pollutant (e.g., Pollutant 2). As illustrated in FIG. 11B, the partitioning at location 1105 is moderately granular. For example, location 1105 is located within medium-sized hexagon 1122. Neighboring hexagons, such as small-sized hexagon 1130, are relatively small. The partitioning at location 1105 may be moderately granular because the data quality measure of the second pollutant (e.g., a spatial data variance of prior measurements of the second pollutant levels) is only moderately differentiated. For example, the second pollutant levels in proximity to location 1105 has a moderated spatial data variance (e.g., a spatial data variance less than a first predetermined variability threshold and more than a second predetermined variability threshold). However, the regions around medium-sized hexagon 1122 have second pollutant levels that are highly differentiated and thus are partitioned into smaller hexagons, such as small-sized hexagon 1130.

Partitioning layer 1140 is generated for a third pollutant (e.g., Pollutant 3). As illustrated in FIG. 11C, the partitioning at location 1105 has a relatively coarse granularity. For example, location 1105 is located within large-sized hexagon 1142. Neighboring hexagons, such as small-sized hexagon 1150, are relatively small. The partitioning at location 1105 may be coarsely granular because the data quality measure of the third pollutant (e.g., a spatial data variance of prior measurements of the third pollutant levels) is relatively lowly differentiated. For example, the third pollutant levels in proximity to location 1105 has a low spatial data variance (e.g., a spatial data variance less than a second predetermined variability threshold). However, the regions around medium-sized hexagon 1142 have third pollutant levels that are highly differentiated and thus are partitioned into smaller hexagons, such as small-sized hexagon 1150.

Figure 11D:
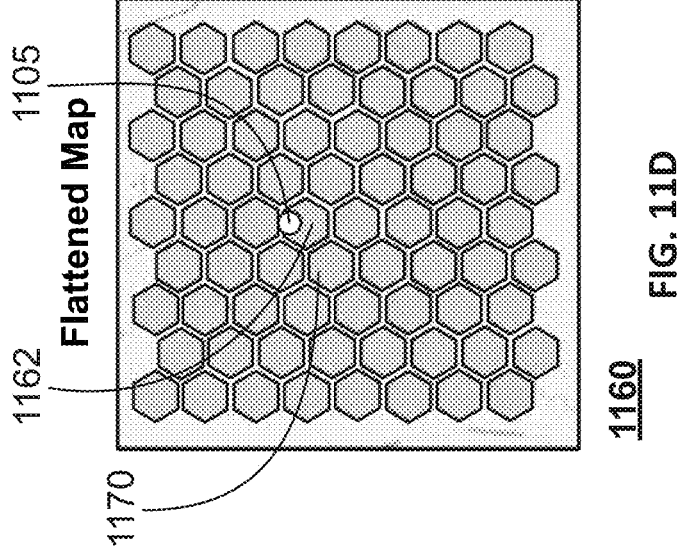
FIG. 11D illustrates a flattening of the partitions of the geographic region to a single partitioning layer according to various embodiments.

FIG. 11D illustrates a flattening of the partitions of the geographic region to a single partitioning layer according to various embodiments. In the example shown, aggregated partitioning layer 1160 is determined (e.g., generated) based at least in part on partitioning layers 1110, 1120, and 1140. As illustrated, the partitioning at location 1105 has a relatively fine granularity. For example, location 1105 is located within small-sized hexagon 1162. The neighboring hexagons, such as small-sized hexagon 1170, are relatively fine/small. The partitioning at location 1105 is determined based on a partitioning at location 1105 in each of partitioning layers 1110, 1120, and 1140. For example, at a selected location, the system deems the granularity of the partitioning at the selected location to be based on (e.g., equal to) the partitioning layer having a finest granularity at the selected location. The partitioning layers respectively generated for the first pollutant, the second pollutant, and the third pollutant (e.g., partitioning layers 1110, 1120, and 1140) are analyzed at particular location 1105, and the finest granularity at the particular location across the set of partitioning layers is used in aggregated partitioning layer. For example, the partitioning used in aggregated partitioning layer is equal to the finest granularity at the location among the set of plurality of partitionings, which in this case is the partitioning in partitioning layer 1100 for the first pollutant. The system uses the size of small-sized hexagon 1110 for the partitioning of the aggregated partitioning layer at the particular location 1105.

Figure 12:
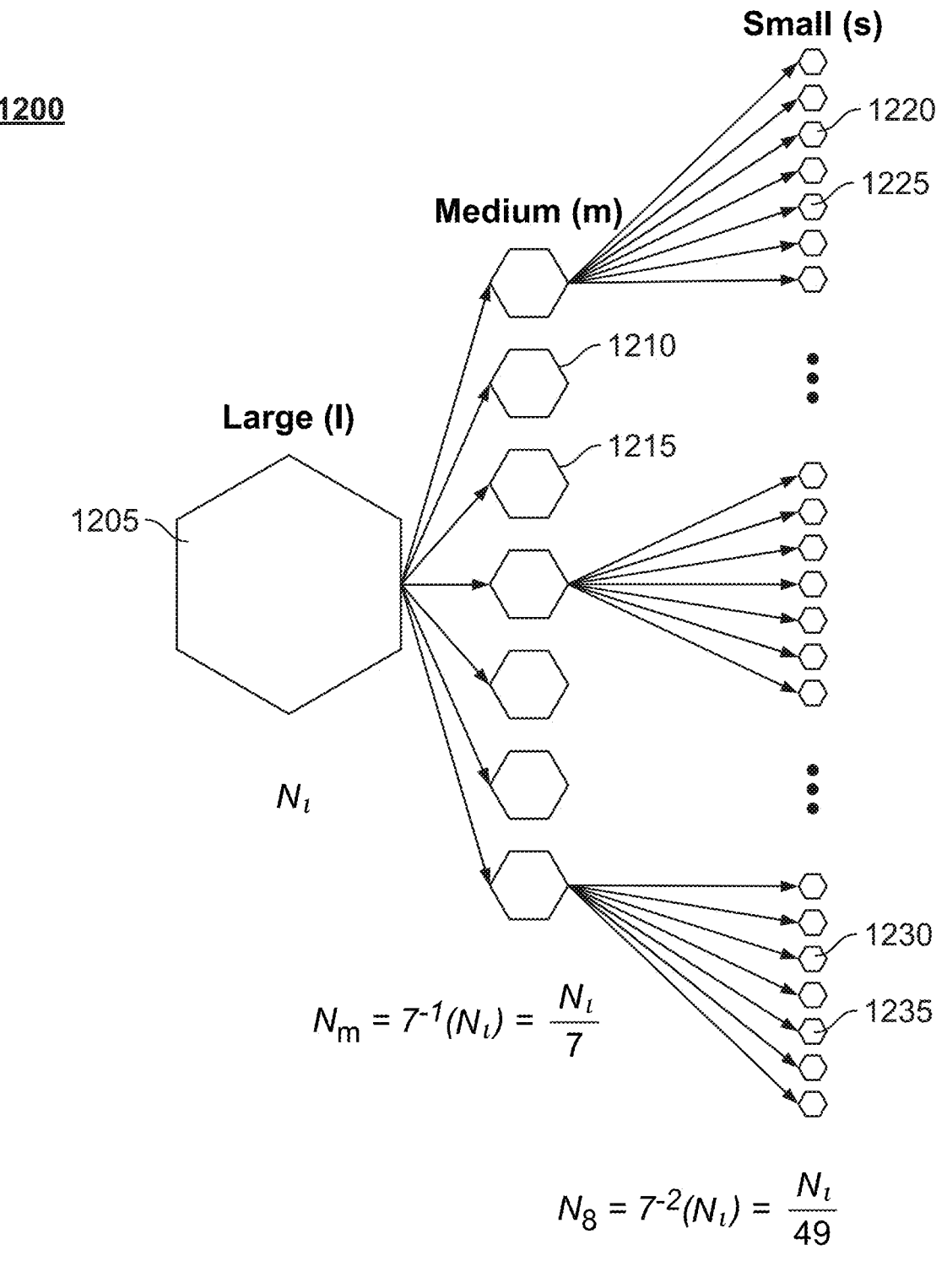
FIG. 12 illustrates a sizing of a partition according to various embodiments.

FIG. 12 illustrates a sizing of a partition according to various embodiments. In the example shown, region partitioning 1200 includes determining a spatial data variance across a geographic region and iteratively determining a size for the partitioned regions (e.g., hexagons) based on the spatial data variance, such as based on determining whether to further partition the hexagon at a particular location or whether to group the hexagon with neighboring hexagons.

As illustrated, the system can partition large-sized hexagon 1205 into a set of seven medium-sized hexagons (e.g., seven equally-sized hexagons), including medium-sized hexagons 1210, 1215, and 1220. The size or boundaries of each of the set of seven medium-sized hexagons may be determined based on the equation $N_m = N_l/7$, where $N_m$ corresponds to the computed need for sampling (e.g., from a cost or scoring function, etc.) associated with a medium-sized hexagon and $N_l$ corresponds to a need for sampling across the large hexagon. Accordingly the need for sampling over the large-sized hexagon is equally divided over the medium-sized hexagons into which the large hexagon is partitioned (or partitionable). The system iteratively determines whether to further partition the second medium-sized hexagons into small-sized hexagons. For example, the system determines whether to partition medium-sized hexagon 1210 into a set of seven small-sized hexagons, including small-sized hexagons 1225, 1230. The system may determine whether to partition medium-sized hexagon 1210 into a set of seven small-sized hexagons based at least in part on a spatial data variance (e.g., a spatial variance for an air quality level of a particular pollutant) of medium-sized hexagon 1210. As another example, the system determines whether to partition medium-sized hexagon 1220 into a set of seven small-sized hexagons, including small-sized hexagons 1235, 1240.

Although the foregoing description includes the determination of whether to further partition a hexagon, the system may conversely determine whether to group a set of seven hexagons. For example, the system may determine whether to group the set of seven small-sized hexagons, including small-sized hexagons 1225, 1230, into a medium-sized hexagon 1210.

The deployment of a set of mobile sensors (e.g., a set of vehicles with mobile sensor platforms mounted thereon) within a geographic region (e.g., a deployment area) during a particular session may include various subsets of the mobile sensors having different beginning and ending points (e.g., within the geographic region). For example, the geographic region may include a plurality of hubs. Each of the plurality of hubs may have a subset of the mobile sensors assigned thereto. A first subset of mobile sensors assigned to a first hub may begin their respective sessions at the first hub (e.g., the vehicles depart the first hub in the morning) and return to the first hub at the end of the session. As an example, the first subset of mobile sensors may be stored and/or maintained at the first-hub when the mobile sensors are not deployed. As another example, the first subset of mobile sensors may commute to the first hub for deployment at the beginning of a corresponding session.

In some embodiments, the system assigns drive plans to the various mobile sensors based on the location of the hubs, the capabilities of the hubs, etc. The system may assign to each hub at least one service area. The service area may define a boundary within which the subset of mobile sensors assigned to the hub are to monitor (e.g., within which the vehicles are deployed to collect samples during a session). The service area assigned to a particular hub may be determined based at least in part on a capability of the hub.

The service area may be further determined based at least in part on a capability of one or more neighboring hubs. For example, the system divides the geographic region (e.g., the contract area) into a set of service areas based at least in part on (i) the boundaries of the geographic region, (ii) the locations of hubs that service the geographic region, and (iii) the respective capabilities of the hubs servicing the geographic region.

In some embodiments, the capabilities of a particular hub is determined based at least in part on one or more of (i) a number of mobile sensor platforms (e.g., number of vehicles, a number of vehicles deployable based on a number of drivers, a number of FTEs, etc.) assigned to the hub, (ii) the types of mobile sensor platforms assigned to the hub, (iii) a number of each type of mobile sensor platform assigned to the hub, (iv) a road network surrounding (e.g., in proximity to) the hub, (v) a speed of roads surrounding the hub (e.g., a posted speed limit, a current road speed, an average historical speed, etc.), (vi) drivers associated with the hub or mobile sensor platforms assigned to the hub, (vii) a location of the hub, etc. Various other characteristics of the hub may be used in connection with determining the capabilities of the hub.

The capabilities of a hub are used to determine a particular service area to be assigned to the hub, such as determining the boundaries of the service area. For example, the system can use the number of mobile sensors and the road network to determine a range/area over which the mobile sensors can be expected to travel during a particular session (e.g., different sessions deployed for a particular day may be different lengths, such as based on driver/operator availability). The boundaries of the service area may be based on a travel distance from the hub across the road network or as the crow flies.

In some embodiments, the geographic region over which sampling is to be performed (e.g., the contracted area for air quality monitoring) is divided into N service area, where N is a positive integer. The system may comprise M hubs, where M is a positive integer. In some implementations, each service area is assigned to a single hub. In some implementations, a particular service area is assigned to a plurality of hubs. In some implementations, a plurality of service areas are assigned to a particular hub.

In some embodiments, partitioned areas (e.g., variable-sized hexagons) are assigned to a service area or a particular hub based on a random selection. The service area or hub to which a particular hexagon is assigned is randomly selected process in which the hexagon has a set of weightings for the set of service areas or the set of hubs servicing the geographic region, or a set of probabilities for the set of service areas or the set of hubs. The weightings may be determined based at least in part on the extent to which a hub is expected to be able to service the particular hub. Accordingly, the weightings for hubs neighboring a hexagon (e.g., hubs within a threshold proximity or a threshold expected travel time) are more heavily weighted than hubs that are distanced from the hexagon. A hexagon is thus biased/more likely to be assigned to a closer hub than a further hub (e.g., closer/further in distance or travel time, etc.). As an example, a target A that is directly adjacent hub H is assigned to hub H every time, but an extremely distanced target B may only assigned to hub H 10% of the time.

In some embodiments, the N service areas in which the geographic region is partitioned are determined by randomly assigning particular hexagons to the M hubs servicing the geographic region. The service area for a hub is defined based on the boundaries of the hexagons that have been randomly assigned to the hub.

In some embodiments, the system determines the service areas and/or randomly assigns the hexagons to hubs at the beginning of each session or set of sessions (e.g., at the beginning of each day).

The partitioning of the geographic region into N service areas and assigned to a corresponding set of M hubs breaks the deployment problem for assigning drive plans across the geographic region from a vehicle routing problem with M hubs to a set of M vehicle routing problems where each vehicle routing problem has a single hub. The system can parallelize the solving the vehicle routing problems. For example, the system uses a set of virtual machines or servers to solve a plurality of the vehicle routing problems (e.g., the assignment of drive plans from a plurality of hubs) in parallel.

Figure 13:
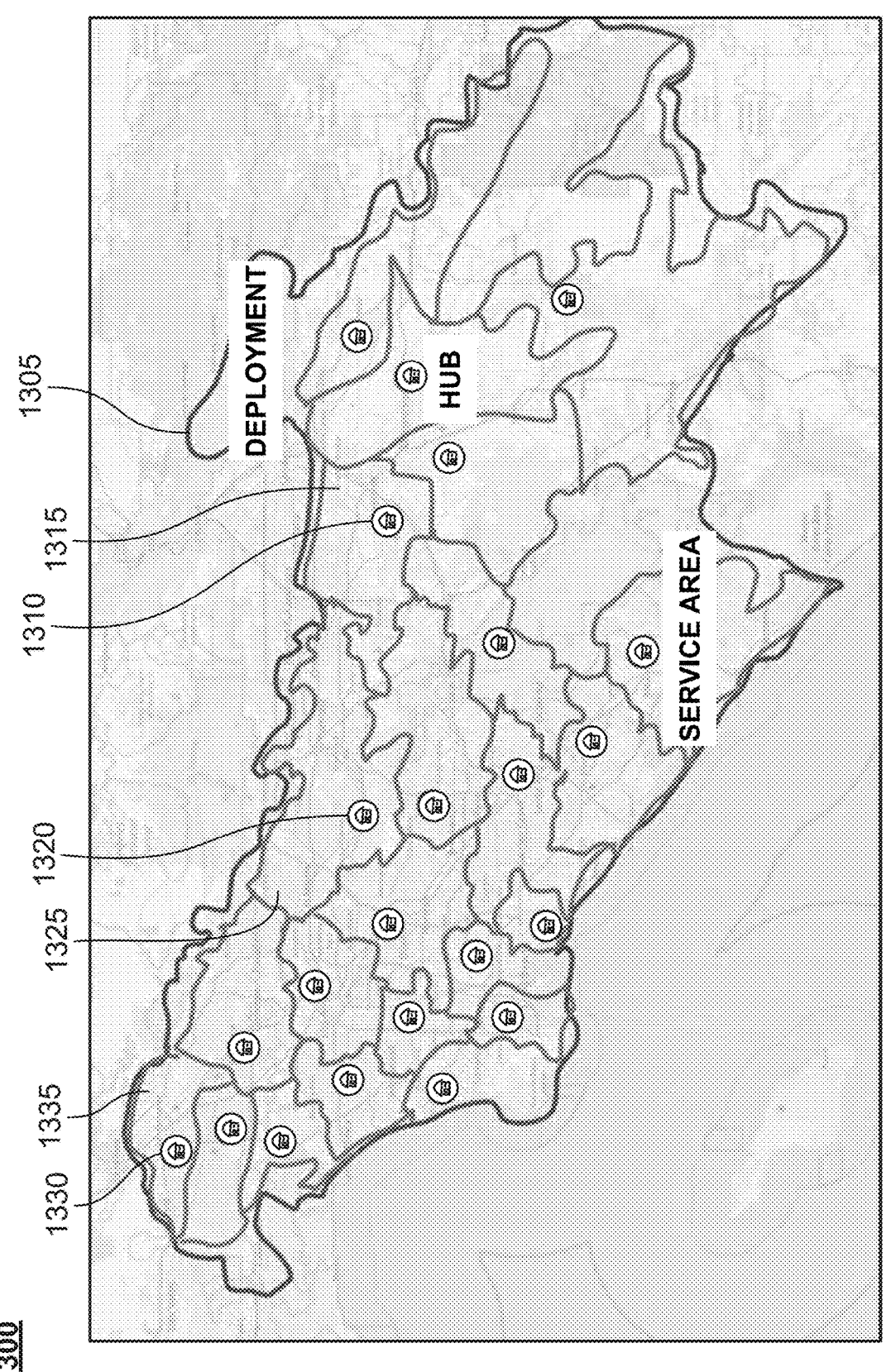
FIG. 13 illustrates a segmentation of a deployment into a set of service areas that are respectively assigned to a hub according to various embodiments.

FIG. 13 illustrates a segmentation of a deployment into a set of service areas that are respectively assigned to a hub according to various embodiments. In the example shown, deployment 1305 is segmented into a plurality of service areas, such as service areas 1315, 1325, and 1335. Deployment 1305 may correspond to the geographic region associated with a set of sessions (e.g., sessions comprised in a drive day). The system may determine different deployments at predetermined time periods or in response to a particular event occurring. As an example, a deployment for a first day can be different for a deployment for a second day. The deployments may be different based on the boundaries of the various service areas within the deployments. In some embodiments, for each deployment, the system stochastically (or probabilistically) assigns hexagons (or other shaped tiles) in the geographic region to the hubs servicing the geographic region, and the assignment of the hexagons defines the service areas.

As illustrated, for deployment 1305, service area 1315 is assigned to hub 1310 (e.g., hub 1310 services service area 1315 during the session), service area 1325 is assigned to hub 1320, and service area 1335 is assigned to hub 1330.

Figure 14:
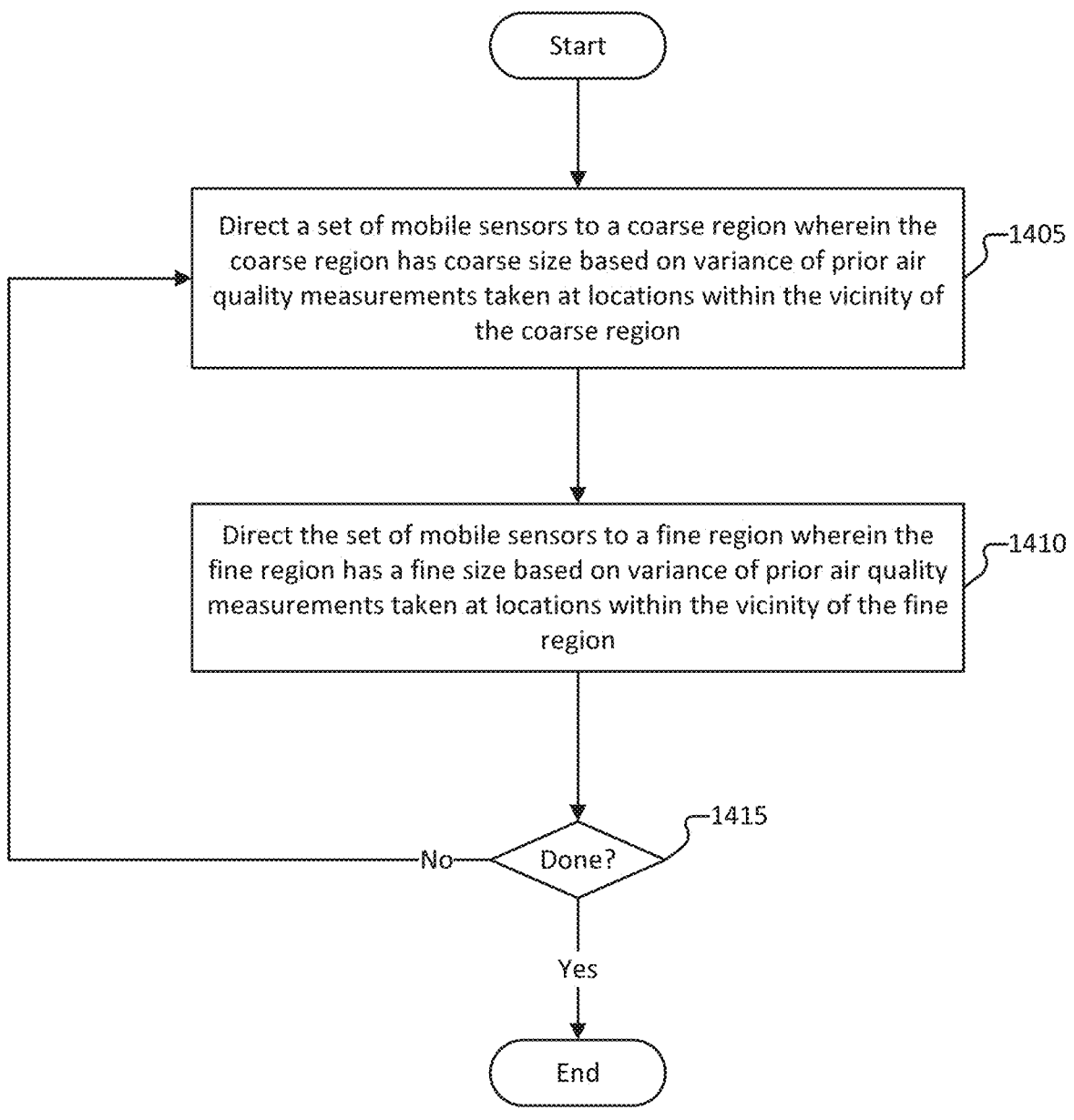
FIG. 14 illustrates a method for directing mobile sensors to perform air quality measurements according to various embodiments.

FIG. 14 illustrates a method for directing mobile sensors to perform air quality measurements according to various embodiments. In some embodiments, process 1400 is implemented at least in part by system 100 of FIG. 1.

In some embodiments, the system determines a sizing of regions based at least in part on a spatial data variance. As described in connection with FIG. 9A, the system groups smaller regions (e.g., hexagons) into a larger region (e.g., a coarse region such as a larger hexagon) if the probability distributions for the smaller regions closely match the probability distribution for the larger region. Similarly, the system partitions a larger region into a set of smaller regions (e.g., a set of equally sized smaller hexagons) if the probability distributions for each (or most) of the smaller regions (e.g., a set of finer regions) do not closely match the probability distribution for the larger region.

At 1405, the system directs a set of mobile sensors to a course region. The coarse region has a coarse size based at least in part on a variance of prior air quality measurements taken at locations within the vicinity of the coarse region. At 1410, the system directs the set of mobile sensors to a fine region. The fine region has a fine size based on a variance of prior air quality measurements taken at locations within the vicinity of the fine region. At 1415, a determination is made as to whether process 1400 is complete. In some embodiments, process 1400 is determined to be complete in response to a determination that no further air quality measurements are to be collected, an air quality measurement session is completed, each vehicle has been assigned a plan for performing air quality measurements for a particular session (e.g., day), an administrator indicates that process 1400 is to be paused or stopped, etc. In response to a determination that process 1400 is complete, process 1400 ends. In response to a determination that process 1400 is not complete, process 1400 returns to 1405.

Figure 15:
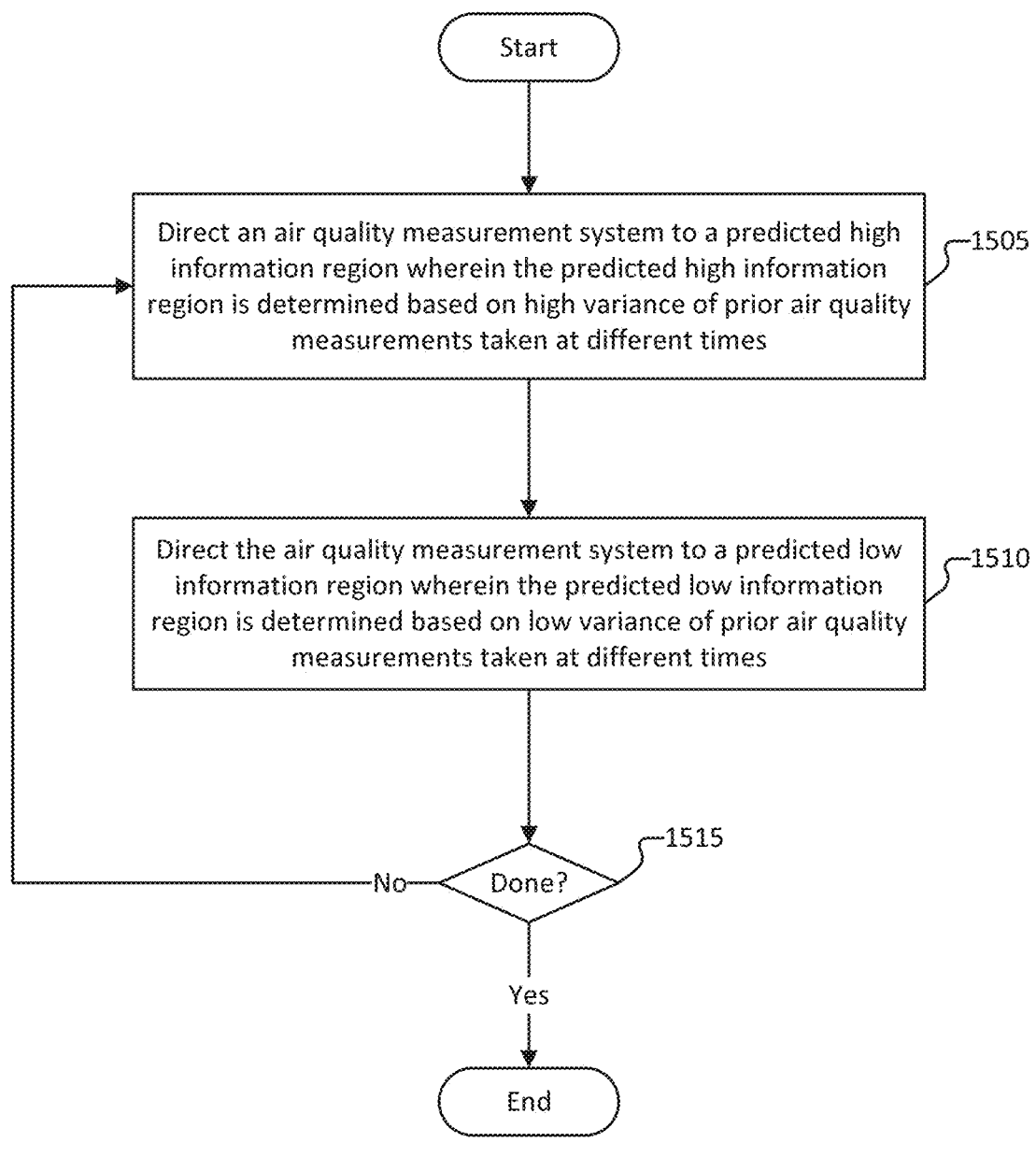
FIG. 15 illustrates a method for directing mobile sensors to perform air quality measurements according to various embodiments.

FIG. 15 illustrates a method for directing mobile sensors to perform air quality measurements according to various embodiments. In some embodiments, process 1500 is implemented at least in part by system 100 of FIG. 1.

In some embodiments, the system determines a prioritization of regions based at least in part on a temporal data variance. As described in connection with FIG. 8B, the system determines a prioritization for a region based at least in part on sampling distribution for a set of historic samples and/or a sampling distribution for a set of recent samples.

At 1505, the system directs the air quality measurement system to a predicted high information region. The predicted high information region is determined based on a high variance of prior air quality measurements taken at different times.

At 1510, the system directs the air quality measurement system to a predicted low information region. The predicted low information region is determined based on a low variance of prior air quality measurements taken at different times.

At 1515, a determination is made as to whether process 1500 is complete. In some embodiments, process 1500 is determined to be complete in response to a determination that no further air quality measurements are to be collected, an air quality measurement session is completed, each vehicle has been assigned a plan for performing air quality measurements for a particular session (e.g., day), an administrator indicates that process 1500 is to be paused or stopped, etc. In response to a determination that process 1500 is complete, process 1500 ends. In response to a determination that process 1500 is not complete, process 1500 returns to 1505.

Figure 16:
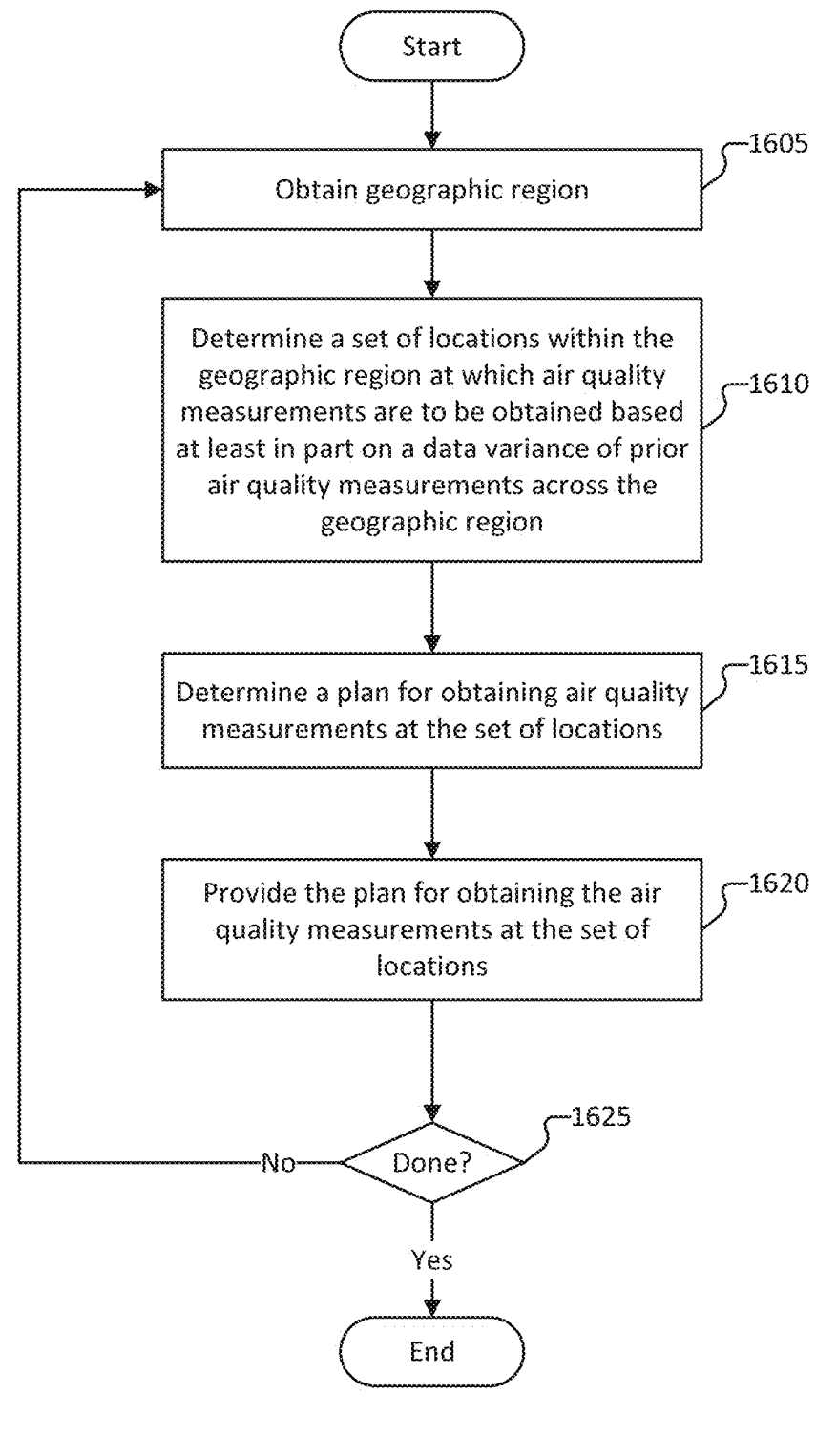
FIG. 16 illustrates a method for determining a plan for performing air quality measurements according to various embodiments.

FIG. 16 illustrates a method for determining a plan for performing air quality measurements according to various embodiments. In some embodiments, process 1600 is implemented at least in part by system 100 of FIG. 1.

In some embodiments, the system randomly selects a set of target regions to be sampled during a session. The set of target regions are randomly selected based at least in part on prioritization weightings assigned to each region. In response to determining the set of target regions to be sampled, the system determines a plan for sampling the set of target regions, including a path to or between target regions. In connection with determining the specific road segments to travel to or between target regions, the system randomly selects the road segments based at least in part on prioritized weightings associated with the road segments. The road segments may be prioritized based on a data quality measure, such as a number of pass counts, and/or a travel time. Additionally, the road segments may be prioritized based at least in part on the detection of a phenomenon, such as a methane leak, from prior air quality measurements.

At 1605, the system obtains a geographic region. The geographic region may be a contracted region over which the system is configured to monitor air quality. At 1610, the system determines a set of locations within the geographic region at which air quality measurements are to be obtained based at least in part on a data variance of prior air quality measurements across the geographic region. At 1615, the system determines a plan for obtaining air quality measurements at the set of locations. The plan may include an ordering of the target region (e.g., to ensure temporal diversity in sampling different regions), a selection of road segments to or between target regions, etc. At 1620, the system provides the plan for obtaining the air quality measurements at the set of locations. At 1620, a determination is made as to whether process 1600 is complete. In some embodiments, process 1600 is determined to be complete in response to a determination that no further air quality measurements are to be collected, no further geographic regions are to be evaluated, all air quality measurement systems/platforms have been assigned a plan, an air quality measurement session is completed, each vehicle has been assigned a plan for performing air quality measurements for a particular session (e.g., day), an administrator indicates that process 1600 is to be paused or stopped, etc. In response to a determination that process 1600 is complete, process 1600 ends. In response to a determination that process 1600 is not complete, process 1600 returns to 1605.

Figure 17:
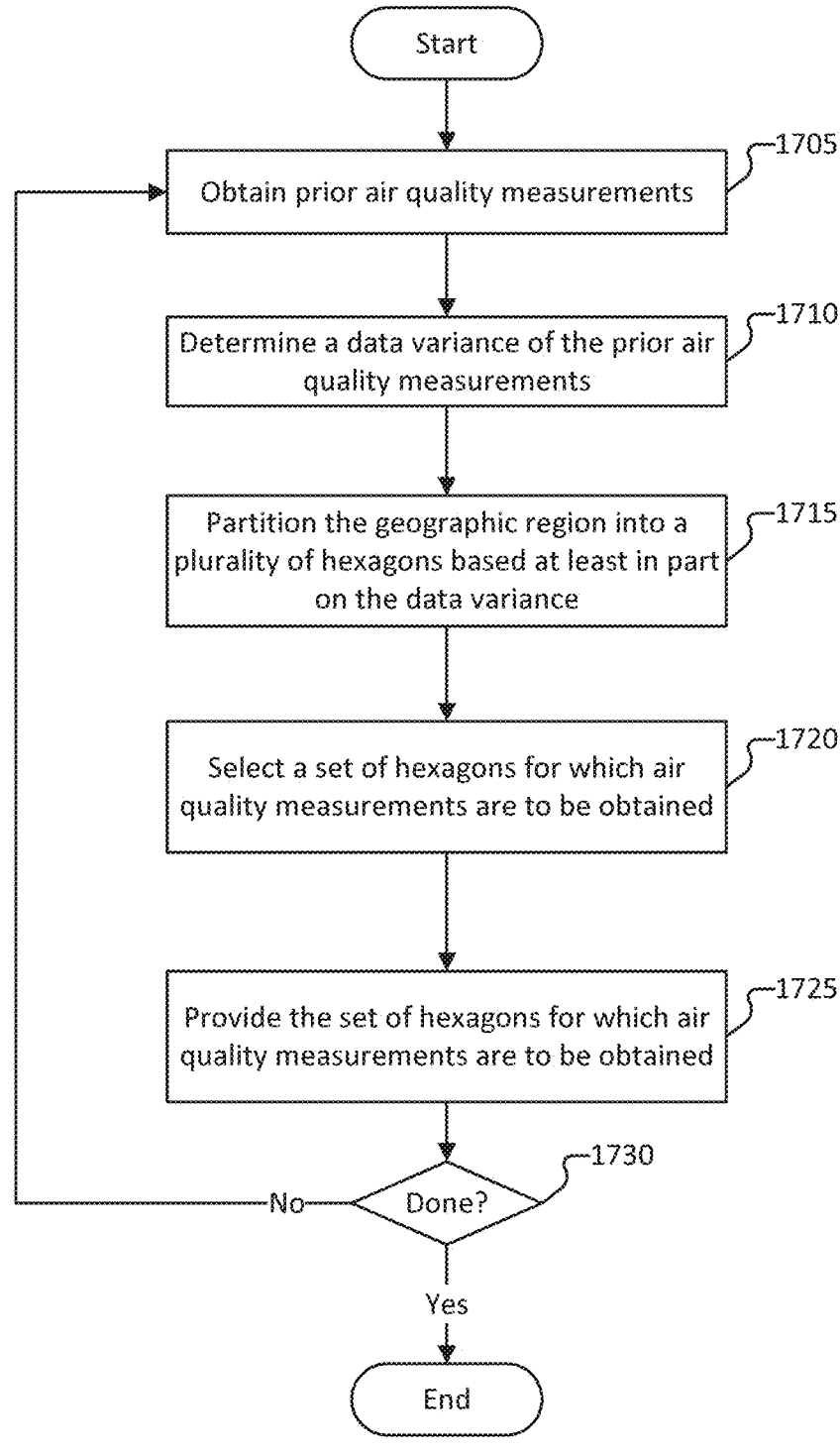
FIG. 17 illustrates a method for partitioning a geographic region into a plurality of target regions for which air quality measurements are to be obtained according to various embodiments.

FIG. 17 illustrates a method for partitioning a geographic region into a plurality of target regions for which air quality measurements are to be obtained according to various embodiments. In some embodiments, process 1700 is implemented at least in part by system 100 of FIG. 1. In some embodiments, process 1700 is invoked by process 1600, such as at 1610.

At 1705, the system obtains prior air quality measurements. At 1710, the system determines a data variance of the prior air quality measurements. At 1715, the system partitions the geographic region into a plurality of hexagons based at least in part on the data variance. At 1720, the system selects a set of hexagons for which air quality measurements are to be obtained. At 1725, the system provides the set of hexagons for which air quality measurements are to be obtained. At 1730, a determination is made as to whether process 1700 is complete. In some embodiments, process 1700 is determined to be complete in response to a determination that no further air quality measurements are to be collected, no further geographic regions are to be evaluated, all air quality measurement systems/platforms have been assigned a plan for collecting air quality measurements during a session (e.g., day), an air quality measurement session is completed, a plan for collecting air quality measurements across a geographic region for a particular session or set of sessions is complete (e.g., a set of sessions for a fleet of vehicles to travel to perform air quality measurement collection), an administrator indicates that process 1700 is to be paused or stopped, etc. In response to a determination that process 1700 is complete, process 1700 ends. In response to a determination that process 1700 is not complete, process 1700 returns to 1705.

Figure 18:
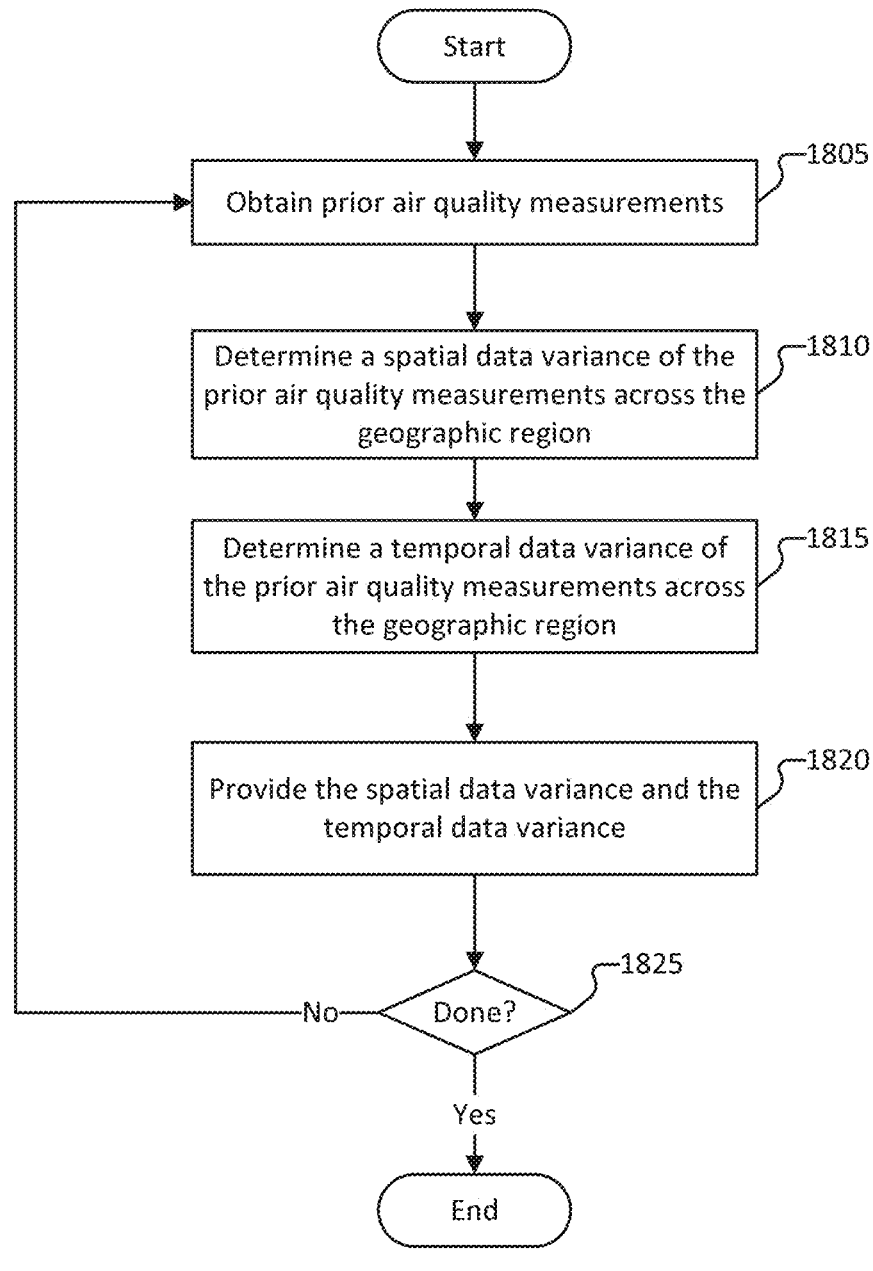
FIG. 18 illustrates a method for analyzing the air quality measurements across various partitions of a geographic region according to various embodiments.

FIG. 18 illustrates a method for analyzing the air quality measurements across various partitions of a geographic region according to various embodiments. In some embodiments, process 1800 is implemented at least in part by system 100 of FIG. 1. In some embodiments, process 1800 is invoked by process 1400, such as at 1410.

In some embodiments, the system statistically analyzes prior air quality measurements (e.g., all historical air quality measurements, or air quality measurements sampled within a predetermined amount of time, etc.). The system may statistically analyze the prior air quality measurements across a geographic region in connection with determining a plan for sampling target regions during a set of sessions (e.g., to determine drive plans for a set of vehicles to travel during a particular day).

At 1805, the system obtains prior air quality measurements. At 1810, the system determines a spatial data variance of the prior air quality measurements across the geographic region. At 1815, the system determines a temporal data variance of the prior air quality measurements across the geographic region. At 1820, the system provides the spatial data variance and the temporal data variance. For example, the system provides the spatial data variance and the temporal data variance to the system, process, or other module that invoked process 1800. At 1825, a determination is made as to whether process 1800 is complete. In some embodiments, process 1800 is determined to be complete in response to a determination that no further air quality measurements are to be collected, no further geographic regions are to be evaluated, all air quality measurement systems/platforms have been assigned a plan for collecting air quality measurements during a session (e.g., day), an air quality measurement session is completed, a plan for collecting air quality measurements across a geographic region for a particular session or set of sessions is complete (e.g., a set of sessions for a fleet of vehicles to travel to perform air quality measurement collection), the target regions for which air quality measurements are to be collected (e.g., during a particular set of sessions, such as by a fleet of vehicles over a particular day) are selected/determined, an administrator indicates that process 1800 is to be paused or stopped, etc. In response to a determination that process 1800 is complete, process 1800 ends. In response to a determination that process 1800 is not complete, process 1800 returns to 1805.

Figure 19:
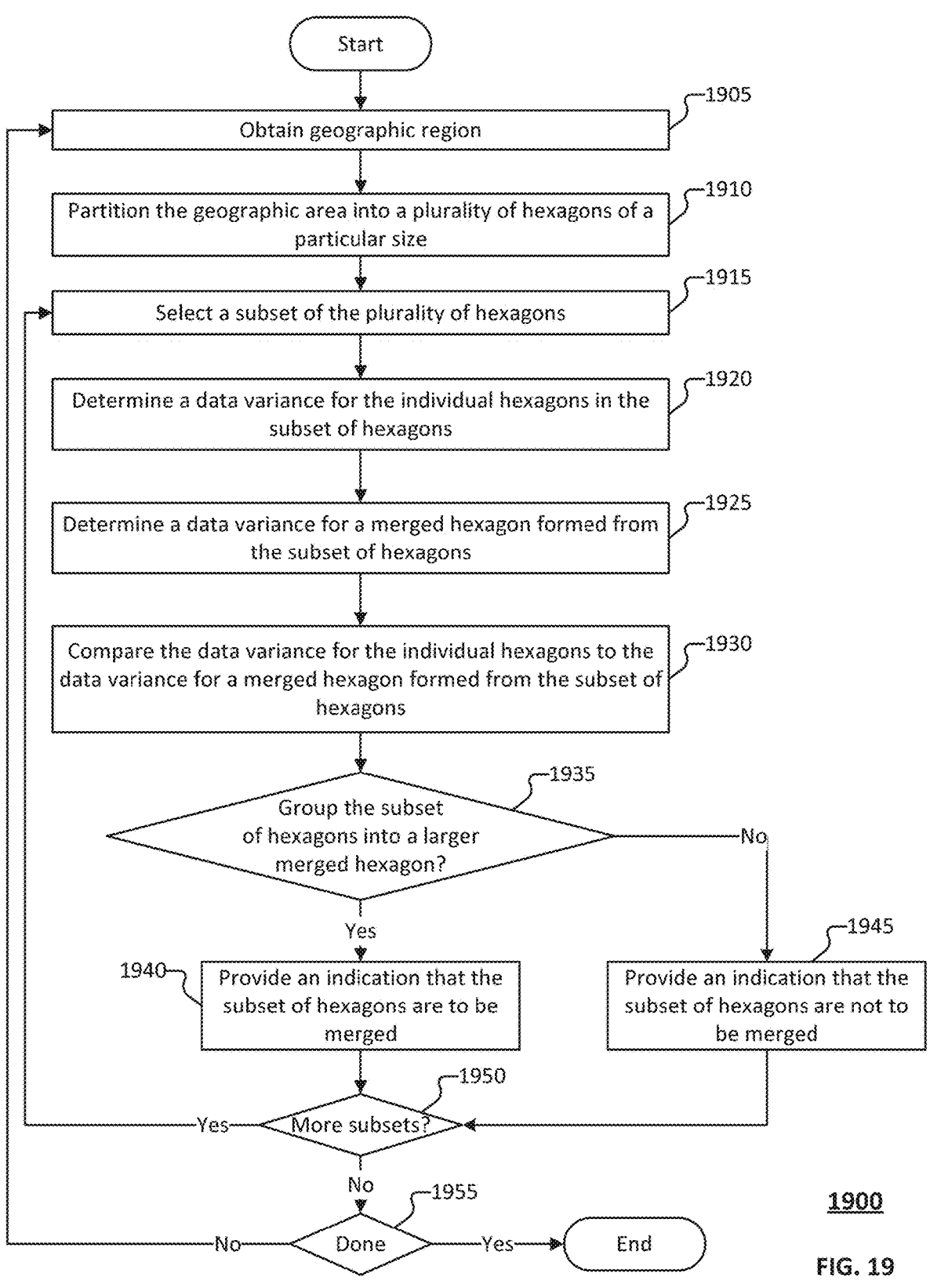
FIG. 19 illustrates a method for grouping partitions of a geographic region according to various embodiments.

FIG. 19 illustrates a method for grouping partitions of a geographic region according to various embodiments. In some embodiments, process 1900 is implemented at least in part by system 100 of FIG. 1. In some embodiments, process 1900 is invoked by process 1600 (e.g., at 1610) or by process 1700 (e.g., at 1715).

At 1905, the system obtains a geographic region.

At 1910, the system partitions the geographic region into a plurality of hexagons of a particular size.

At 1915, the system selects a subset of the plurality of hexagons. For example, the system selects a set of seven neighboring hexagons that, when combined, form a larger hexagon.

At 1920, the system determines a data variance for the individual hexagons in the selected subset of hexagons. For example, the system evaluates the spatial data variance of the prior air quality measurements over the regions defined by the hexagons.

At 1925, the system determines a data variance for a merged hexagon formed from the subset of hexagons. For example, the system simulates merging/grouping the subset of hexagons into a single larger hexagon and evaluates the spatial data variance across the region defined by the larger hexagon.

At 1930, the system compares the data variance for the individual hexagons to the data variance for a merged hexagon formed from the subset of hexagons. In some embodiments, the system evaluates an extent to which the data variances over the subset of hexagons (or any one of the subset of hexagons) and the merged hexagon differ.

At 1935, the system determines whether to group the subset of hexagons into a larger merged hexagon. For example, the system determines whether to group the subset of hexagons if the extent of the difference between the data variances of the subset of hexagons (e.g., each hexagon in the subset of hexagons) and the data variance of the merged hexagon is less than a predefined spatial data variance threshold. If the extent of the difference between the data variances of the subset of hexagons (e.g., each hexagon in the subset of hexagons) and the data variance of the merged hexagon is less than the predefined spatial data variance threshold, then the system determines to group the subset of hexagons (e.g., to use the merged hexagon as a particular region over which air quality measurements may be more coarsely collected). Conversely, if the extent of the difference between the data variances of the subset of hexagons (e.g., each hexagon in the subset of hexagons) and the data variance of the merged hexagon is greater than the predefined spatial data variance threshold, then the system determines not to group the subset of hexagons (e.g., to use the individual hexagons in the subset of hexagons as different regions over which air quality measurements may be more finely collected).

In response to determining that the subset of hexagons is to be grouped in a larger merged hexagon, process 1900 proceeds to 1940 and the system provides an indication that the subset of hexagons are to be merged. For example, the system provides to the other system or process that invoked process 1900 an indication that air quality measurements are to be collected over the region defined by the subset of hexagons more coarsely across the larger merged hexagon (e.g., the area defined by the collection of the subset of hexagons is to be treated as a single region when determining whether to assign the region as a target region for air quality measurement during a session).

In response to determining that the subset of hexagons is not to be grouped in a larger merged hexagon, process 1900 proceeds to 1945 and the system provides an indication that the subset of hexagons are to not be merged. For example, the system provides to the other system or process that invoked process 1900 an indication that air quality measurements are to be collected over the region defined by the subset of hexagons finely across each of the hexagons in the subset of hexagons as different regions (e.g., the area defined by an individual hexagon in the subset of hexagons is to be treated as a single region when determining whether to assign the region as a target region for air quality measurement during a session).

At 1950, the system determines whether any further subsets of hexagons (e.g., group of seven hexagons) are to be evaluated, such as in connection with determining whether the hexagons are to be grouped, or otherwise determining regions over which air quality measurements are to be collected. In response to determining that further subsets of hexagons are to be evaluated, process 1900 returns to 1915 and process 1900 iterates over 1615-1650 until no further hexagons are to be evaluated. Conversely, in response to determining that no further subsets of hexagons are to be evaluated, process 1900 proceeds to 1955.

At 1955, a determination is made as to whether process 1900 is complete. In some embodiments, process 1900 is determined to be complete in response to a determination that no further air quality measurements are to be collected, no further geographic regions are to be evaluated, all air quality measurement systems/platforms have been assigned a plan for collecting air quality measurements during a session (e.g., day), an air quality measurement session is completed, a plan for collecting air quality measurements across a geographic region for a particular session or set of sessions is complete (e.g., a set of sessions for a fleet of vehicles to travel to perform air quality measurement collection), the target regions for which air quality measurements are to be collected (e.g., during a particular set of sessions, such as by a fleet of vehicles over a particular day)

are selected/determined, an administrator indicates that process 1900 is to be paused or stopped, etc. In response to a determination that process 1900 is complete, process 1900 ends. In response to a determination that process 1900 is not complete, process 1900 returns to 1905.

Figure 20:
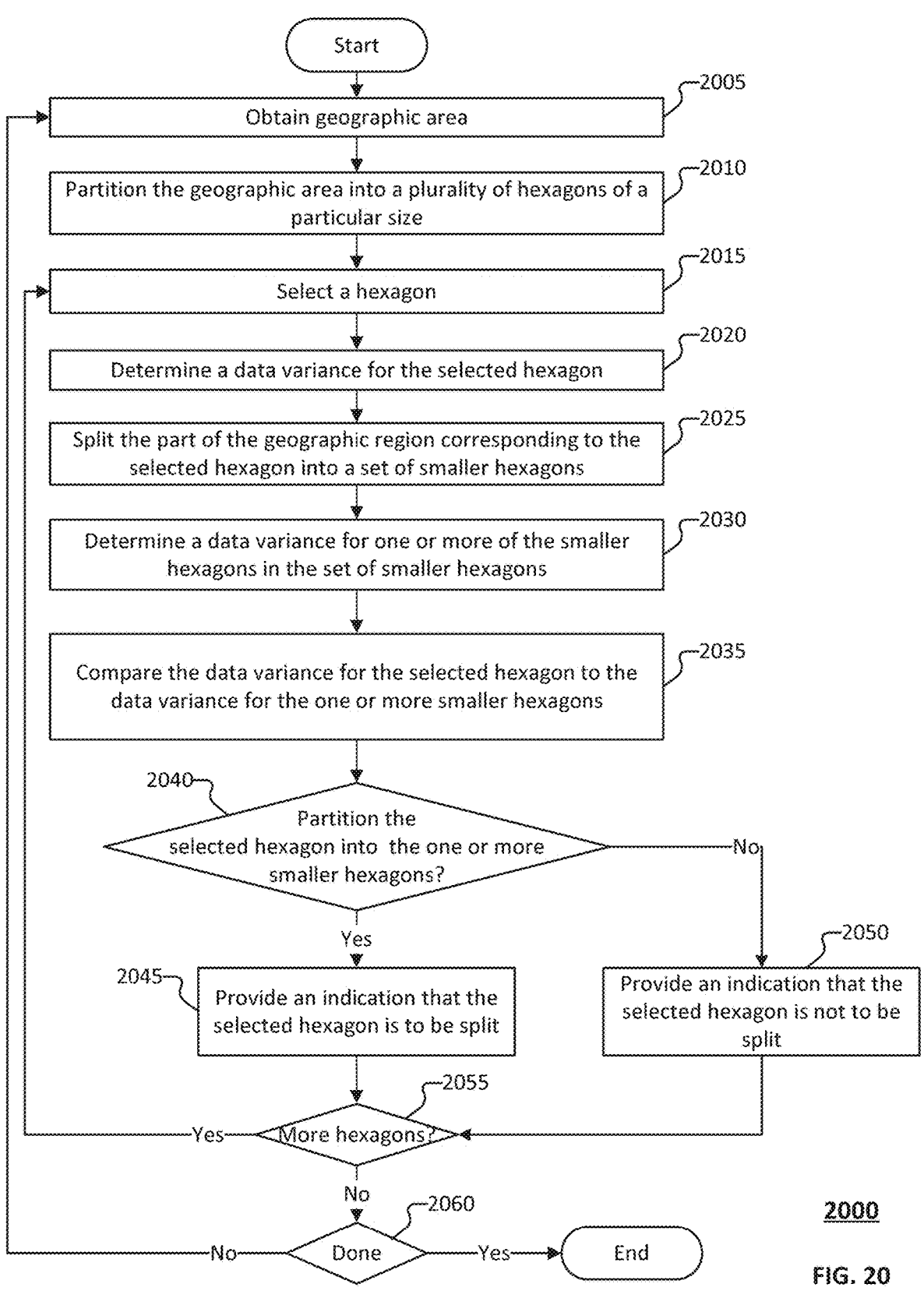
FIG. 20 illustrates a method for splitting partitions of a geographic region according to various embodiments.

FIG. 20 illustrates a method for splitting partitions of a geographic region according to various embodiments. In some embodiments, process 2000 is implemented at least in part by system 100 of FIG. 1. In some embodiments, process 2000 is invoked by process 1600 (e.g., at 1610) or by process 1700 (e.g., at 1715).

At 2005, the system obtains a geographic region.

At 2010, the system partitions the geographic region into a plurality of hexagons of a particular size.

At 2015, the system selects a hexagon. For example, the system selects a hexagon from the plurality of hexagons.

At 2020, the system determines a data variance for the selected hexagon. For example, the system evaluates the spatial data variance of the prior air quality measurements over the region defined by the selected hexagon.

At 2025, the system splits (e.g., further partitions) the selected hexagon into a set of smaller hexagons. For example, the system splits the selected hexagon into seven smaller and equal-sized hexagons.

At 2030, the system determines a data variance for the set of smaller hexagons. For example, the system simulates splitting the hexagon into equally-sized smaller hexagons for evaluation of whether the selected hexagon should be split into the set of smaller hexagons for collection of air quality measurements.

At 2035, the system compares the data variance for the individual hexagons in the set of smaller hexagons to the data variance for the selected hexagon. In some embodiments, the system evaluates an extent to which the data variances over the set of smaller hexagons (or any one of the set of smaller hexagons) and the selected hexagon (e.g., the single larger hexagon) differ.

At 2040, the system determines whether to partition/split the selected hexagon into the set of smaller hexagons. For example, the system determines whether to split the selected hexagon into a set of smaller geographic regions (e.g., seven equally sized hexagons) if the extent of the difference between the data variances of the set of smaller hexagons (e.g., each hexagon in the set of smaller hexagons) and the data variance of the selected hexagon is greater than a predefined spatial data variance threshold. If the extent of the difference between the data variances of the set of smaller hexagons (e.g., each hexagon in the set of smaller hexagons) and the data variance of the selected hexagon is greater than the predefined spatial data variance threshold, then the system determines to split the selected hexagon into the set of smaller hexagons (e.g., to use the set of smaller hexagons as individual regions over which air quality measurements may be more coarsely collected). Conversely, if the extent of the difference between the data variances of the set of smaller hexagons (e.g., each hexagon in the set of smaller hexagons) and the data variance of the selected hexagon is less than or equal to the predefined spatial data variance threshold, then the system determines not to split the selected hexagon into the set of smaller hexagons (e.g., to use the selected hexagon as a single region over which air quality measurements may be more finely collected).

In response to determining that the selected hexagon is to be split into the one or more smaller hexagons, process 2000 proceeds to 2045 and the system provides an indication that the selected hexagon is to be split/partitioned into the set of smaller hexagons. For example, the system provides to the other system or process that invoked process 2000 an indication that air quality measurements are to be collected over the plurality of individual regions defined by the set of smaller regions more finely across the selected hexagon (e.g., the area defined by the selected hexagons is to be treated as a plurality of individual regions when determining whether to assign the region as a target region for air quality measurement during a session).

In response to determining that the subset of hexagons is to be grouped in a larger merged hexagon, process 2000 proceeds to 2050 and the system provides an indication that the subset of hexagons are to not be split. For example, the system provides to the other system or process that invoked process 2000 an indication that air quality measurements are to be collected over the region defined by the selected hexagon as a single region (e.g., the area defined by an selected hexagon is to be treated as a single region, or combined with another set of equally sized hexagons to form a larger hexagon, when determining whether to assign the region as a target region for air quality measurement during a session).

At 2055, the system determines whether any further hexagons are to be evaluated, such as in connection with determining whether the hexagons are to be split, or otherwise determining regions over which air quality measurements are to be collected. In response to determining that further subsets of hexagons are to be evaluated, process 2000 returns to 2015 and process 2000 iterates over 2015-2055 until no further hexagons are to be evaluated. Conversely, in response to determining that no further subsets of hexagons are to be evaluated, process 2000 proceeds to 2060.

At 2060, a determination is made as to whether process 2000 is complete. In some embodiments, process 2000 is determined to be complete in response to a determination that no further air quality measurements are to be collected, no further geographic regions are to be evaluated, all air quality measurement systems/platforms have been assigned a plan for collecting air quality measurements during a session (e.g., day), an air quality measurement session is completed, a plan for collecting air quality measurements across a geographic region for a particular session or set of sessions is complete (e.g., a set of sessions for a fleet of vehicles to travel to perform air quality measurement collection), the target regions for which air quality measurements are to be collected (e.g., during a particular set of sessions, such as by a fleet of vehicles over a particular day) are selected/determined, an administrator indicates that process 2000 is to be paused or stopped, etc. In response to a determination that process 2000 is complete, process 2000 ends. In response to a determination that process 2000 is not complete, process 2000 returns to 2005.

Figure 21:
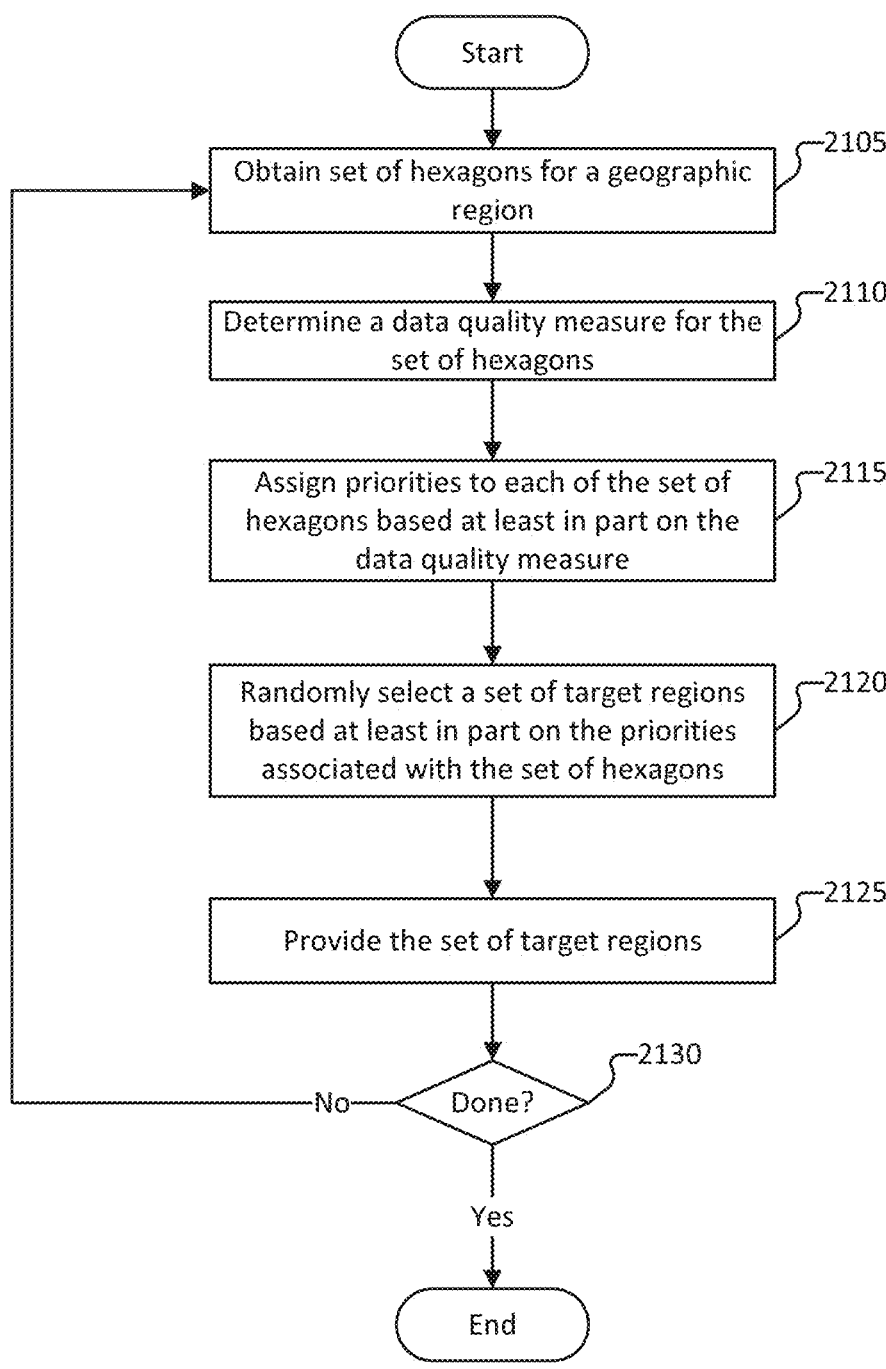
FIG. 21 illustrates a method for determining a set of target regions at which air quality measurements are to be collected according to various embodiments.

FIG. 21 illustrates a method for determining a set of target regions at which air quality measurements are to be collected according to various embodiments. In some embodiments, process 2100 is implemented at least in part by system 100 of FIG. 1. In some embodiments, process 2100 is invoked by process 1600 (e.g., at 1615).

At 2105, the system obtains a set of hexagons for a geographic region. The set of hexagons may comprise hexagons of various different sizes based on the merging or splitting of hexagons within the geographic region according to the spatial data variance (e.g., to group hexagons having low spatial data variances and to split a hexagon having high spatial data variance across the hexagonal area). At 2110, the system determines a data quality measure for the set of hexagons. The data quality measurement may include one or more of temporal data variance, spatial data variance, pass counts, an identification of an anomaly or leak in a certain area (e.g., a likelihood of an anomaly or leak within a particular region), a model error metric, a need function, etc. At 2115, the system assigns priorities to each of the set of hexagons based at least in part on the data quality measure. In some embodiments, the system determines, based on the data quality measure, a set of weights respectively associated with the set of hexagons. The weights may be used in connection with selecting hexagons over which air quality measurement is to be collected during a session. As an example, higher priority hexagons are associated with higher weights. At 2120, the system randomly selects the set of target regions based at least in part on the priorities associated with the set of hexagons. At 2125, the system provides the set of target regions. At 2130, a determination is made as to whether process 2100 is complete. In some embodiments, process 2100 is determined to be complete in response to a determination that no further air quality measurements are to be collected, no further geographic regions are to be evaluated, no further regions/hexagons are to be assigned to an air quality measurement system, all air quality measurement systems/platforms have been assigned a plan for collecting air quality measurements during a session (e.g., day), an air quality measurement session is completed, a plan for collecting air quality measurements across a geographic region for a particular session or set of sessions is complete (e.g., a set of sessions for a fleet of vehicles to travel to perform air quality measurement collection), the target regions for which air quality measurements are to be collected (e.g., during a particular set of sessions, such as by a fleet of vehicles over a particular day) are selected/determined, an administrator indicates that process 2100 is to be paused or stopped, etc. In response to a determination that process 2100 is complete, process 2100 ends. In response to a determination that process 2100 is not complete, process 2100 returns to 2105.

Figure 22:
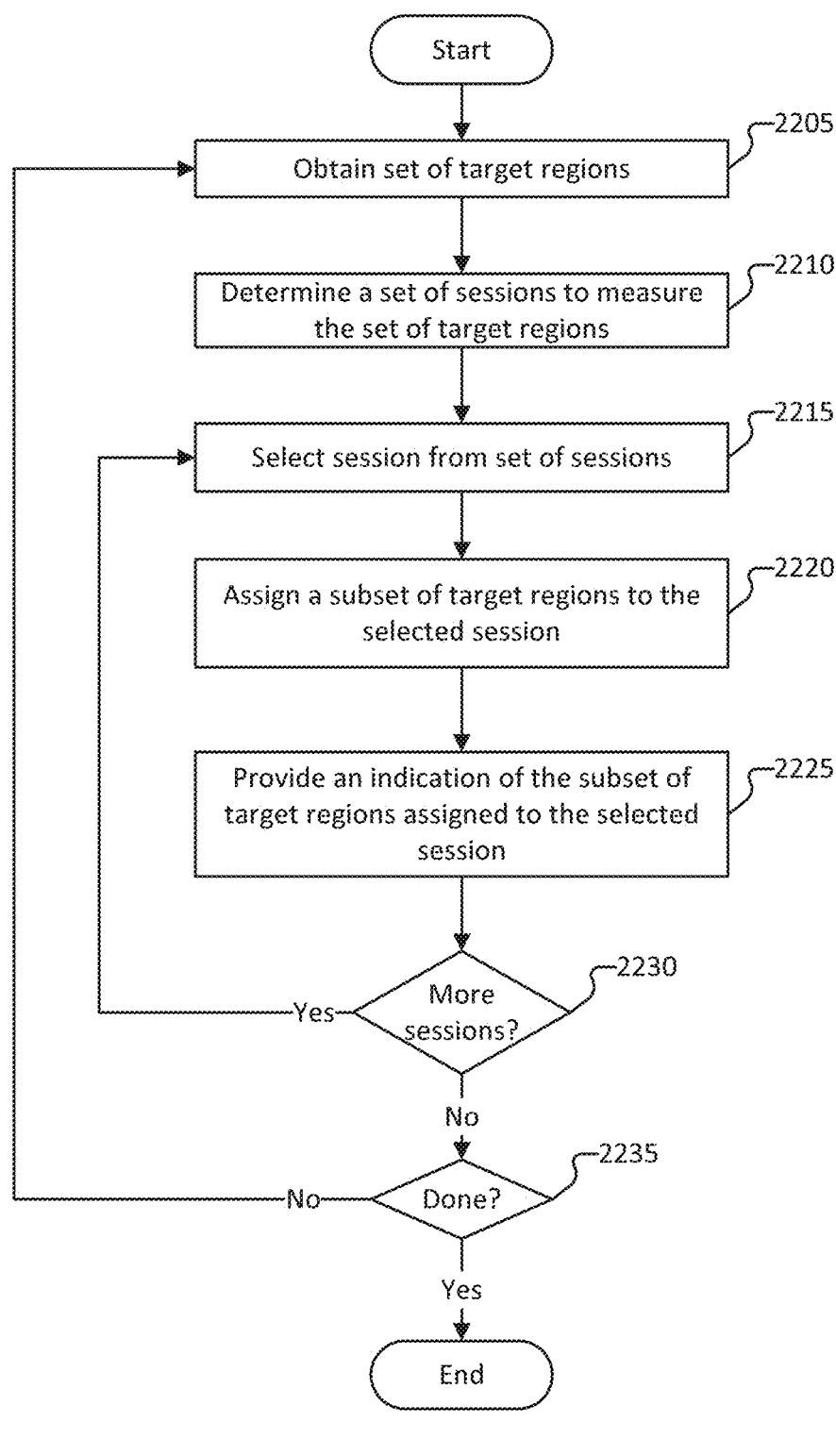
FIG. 22 illustrates a method for assigning target regions to sessions for air quality measurements collection according to various embodiments.

FIG. 22 illustrates a method for assigning target regions to sessions for air quality measurement collection according to various embodiments. In some embodiments, process 2200 is implemented at least in part by system 100 of FIG. 1. In some embodiments, process 2200 is invoked by process 1600 (e.g., at 1615).

At 2205, the system obtains a set of target regions.

At 2210, the system determines a set of sessions to measure the set of target regions. For example, at the beginning of the day the system determines a number of air quality measurement systems (e.g., vehicles with mounted mobile sensors) that are to be deployed to collect air quality measurements according to respective plans.

At 2215, the system selects a session from a set of sessions. For example, the system selects an air quality measurement system for which a plan for air quality measurement is to be collected during its corresponding session (e.g., during that day).

At 2220, the system assigns a subset of target regions to the selected session. The system may assign the subset of target regions based on one or more of (a) a distance between target regions, (b) a priority assigned to a target region, (c) a temporal data variance across the set of target regions, (d) a total distance to be travelled to collect air quality measurements at the subset of target regions, (e) a length of a session, (f) posted road speeds associated with road segments connecting the subset of target regions, (g) average road speeds associated with the segments connecting the subset of target regions, (h) an indication(s) of a collision, a road construction zone, and/or a hazard, etc.

At 2225, the system provides an indication of the subset of target regions assigned to the selected session. In some embodiments, the system provides the indication of the subset of target regions to another system, module, or process that invoked process 2200. The indication of the subset of target regions may be used in connection with determining a plan for an air quality measurement system to be deployed during a session to collect air quality measurements at the subset of target regions.

At 2230, the system determines whether target regions are to be assigned to other sessions. In response to determining that target regions are to be assigned to further sessions, process 2200 returns to 2215 and process 2200 iterates over 2215-2230 until no further sessions are to be assigned target regions. Conversely, in response to determining that no further sessions are to be assigned target regions, process 2200 proceeds to 2235.

At 2235, a determination is made as to whether process 2200 is complete. In some embodiments, process 2200 is determined to be complete in response to a determination that no further air quality measurements are to be collected, no further regions/hexagons are to be assigned to an air quality measurement system, no further sessions or air quality measurement systems/platforms are to be assigned target regions, all air quality measurement systems/platforms have been assigned a plan for collecting air quality measurements during a session (e.g., day), an administrator indicates that process 2200 is to be paused or stopped, etc. In response to a determination that process 2200 is complete, process 2200 ends. In response to a determination that process 2200 is not complete, process 2200 returns to 2205.

Figure 23:
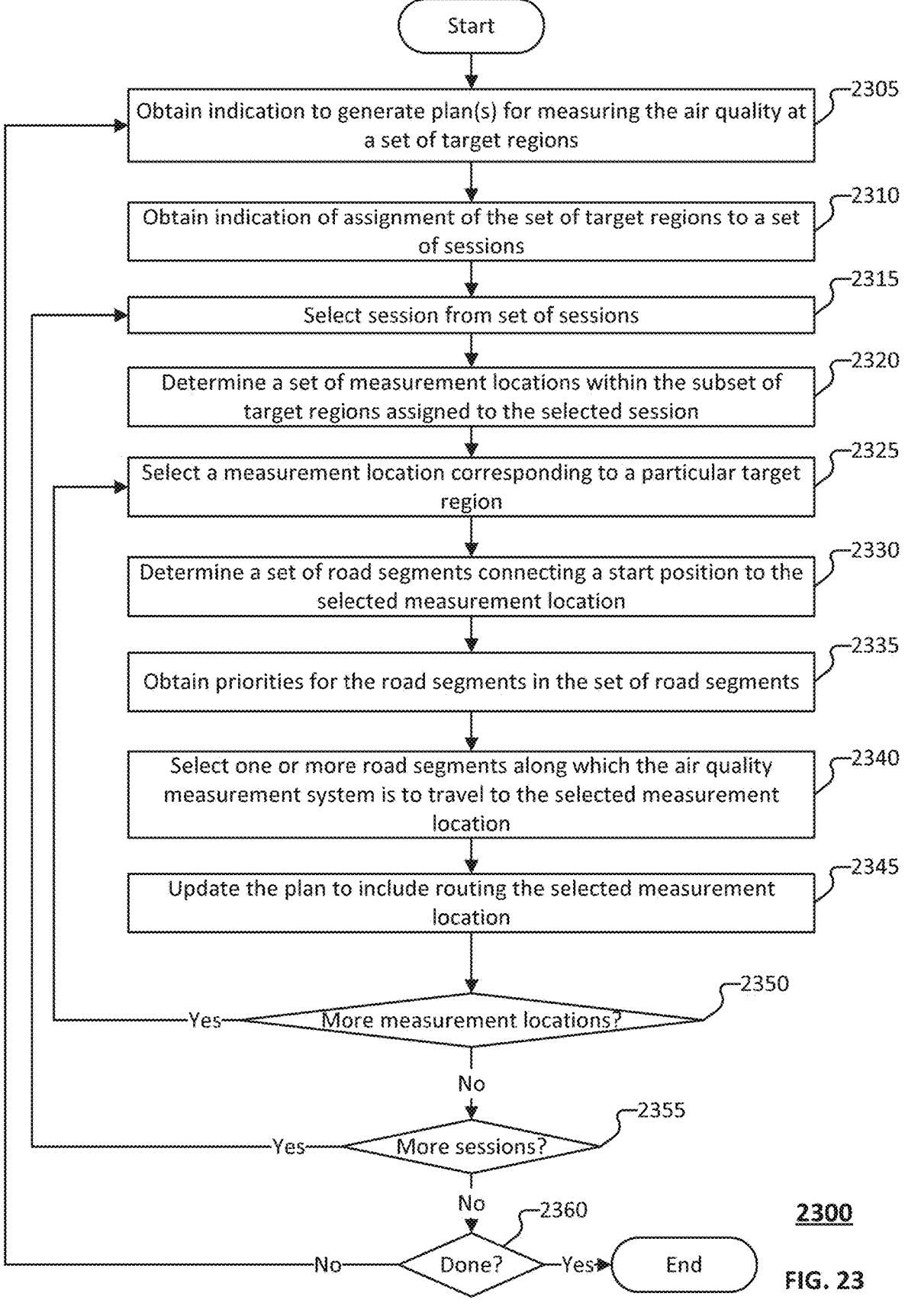
FIG. 23 illustrates a method for route planning a session for collecting air quality measurements at a set of target regions according to various embodiments.

FIG. 23 illustrates a method for route planning a session for collecting air quality measurements at a set of target regions according to various embodiments. In some embodiments, process 2300 is implemented at least in part by system 100 of FIG. 1. In some embodiments, process 2300 is invoked by process 1600 (e.g., at 1615).

At 2305, the system obtains an indication to generate a plan(s) for measuring the air quality at a set of target regions.

At 2310, the system obtains an indication of the assignment of the set of target regions to a set of sessions.

At 2315, the system selects a session from the set of sessions.

At 2320, the system determines a set of measurement locations within the subset of target regions assigned to the selected session. In some embodiments, for each target region, the system randomly selects a location within the target region at which the air quality measurement is to be collected for the target region. The location may be selected based at least in part on one or more of (i) the spatial data variance for air quality measurements across the target region, (ii) a number of pass counts for the location or within a predefined proximity of the location, (iii) a time that has elapsed since a last air quality measurement was collected, etc.

At 2325, the system selects a measurement location (e.g., a target location) corresponding to a particular target region. The system may select the measurement location based at least in part on an order of measurement locations to be visited during a session or random selection. The system may select the measurement locations based at least in part on one or more of (i) a spatial distribution of sampling within the target region, (ii) temporal data variance used to select order of measurement locations or assign priorities, (iii) a number of pass counts to the various locations or within a predefined distance of the location, (iv) a likelihood that an anomaly or leak is expected to be detected, etc.

At 2330, the system determines a set of road segments connecting a start position to the selected measurement location. For example, the start position is the location of the air quality measurement system at the beginning of the session, or a measurement location for a target region to be visited immediately before the selected measurement location.

At 2335, the system obtains priorities for the road segments in the set of road segments.

At 2340, the system selects one or more road segments along which the air quality measurement system is to travel to the selected measurement location.

At 2345, the system updates a plan for the air quality measurement system to perform during the session. The plan is updated to include routing the selected measurement location. For example, the plan includes a turn-by-turn routing of the air quality measurement location to cause the air quality measurement system to travel and collect air quality measurements at the set of measurement locations associated with the session and selected road segments connecting the set of measurement locations.

At 2350, the system determines whether additional measurement locations are to be added to the plan. For example, the system determines whether the length of the session will allow for another measurement location(s) to be added to the session. As another example, the system determines to add another measurement location to the plan if total distance travelled according to the current plan is less than a predefined distance threshold.

In response to determining that additional measurement locations are to be added to the plan, process 2300 returns to 2325 and process 2300 iterates over 2325-2350 until no further measurement locations are to be added. Conversely, in response to determining that no additional measurement locations are to be added to the plan, process 2300 proceeds to 2355.

At 2355, the system determines whether plans are to be generated for other sessions. In response to determining that plans are to be generated for another session(s), process 2300 returns to 2315 and process 2300 iterates over 2315-2355 until no further plans are to be generated for sessions. Conversely, in response to determining that no further plans are to be generated for the sessions, process 2300 proceeds to 2360.

At 2360, a determination is made as to whether process 2300 is complete. In some embodiments, process 2300 is determined to be complete in response to a determination that no further air quality measurements are to be collected, no further regions/hexagons are to be assigned to an air quality measurement system, no further sessions or air quality measurement systems/platforms are to be assigned target regions, all air quality measurement systems/platforms have been assigned a plan for collecting air quality measurements during a session (e.g., day), an administrator indicates that process 2300 is to be paused or stopped, etc. In response to a determination that process 2300 is complete, process 2300 ends. In response to a determination that process 2300 is not complete, process 2300 returns to 2305.

Figure 24:
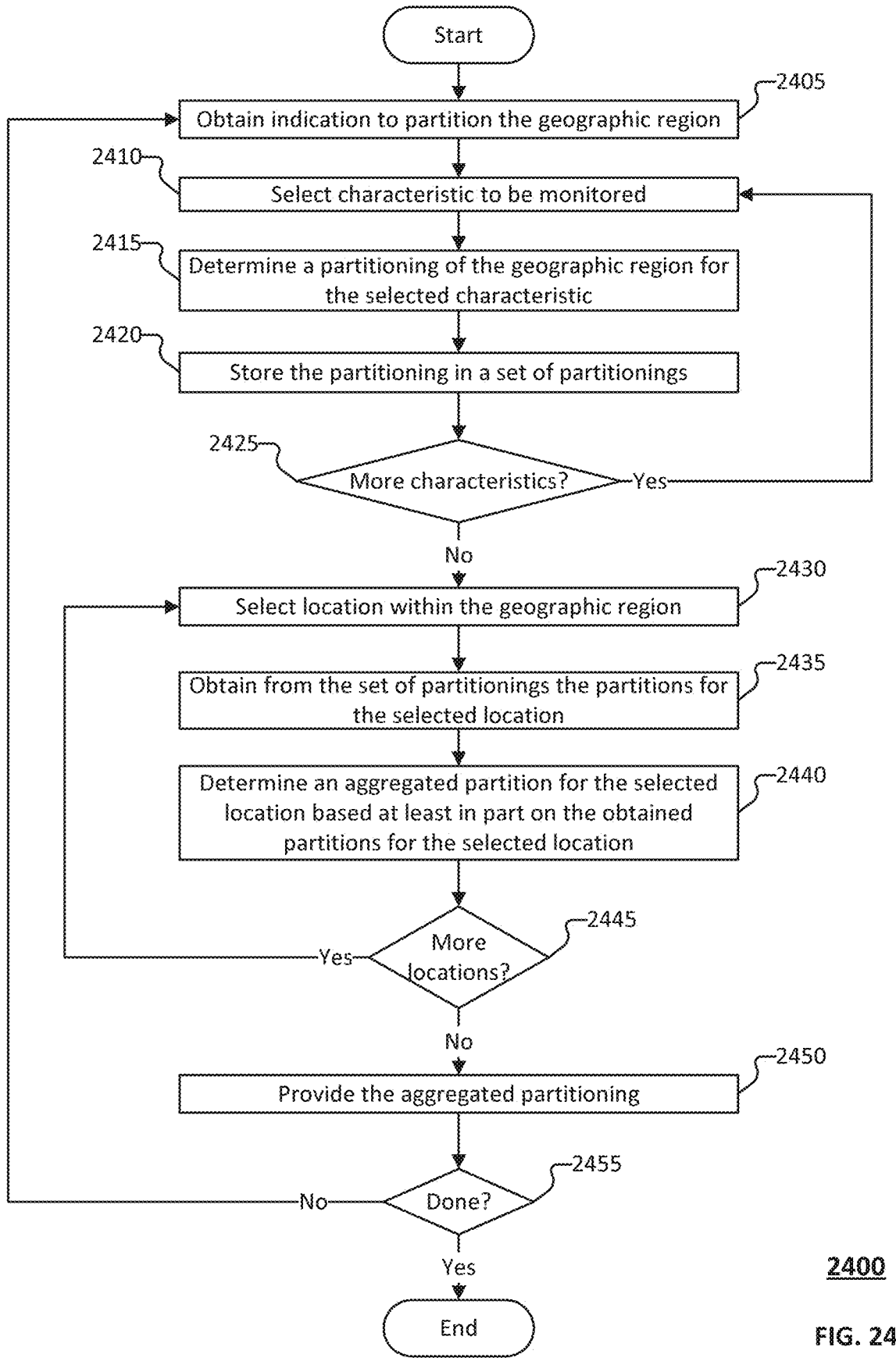
FIG. 24 illustrates a method for assigning target regions to sessions for air quality measurements collection according to various embodiments.

FIG. 24 illustrates a method for assigning target regions to sessions for air quality measurement collection according to various embodiments. In some embodiments, process 2400 is implemented at least in part by system 100 of FIG. 1. In some embodiments, process 2400 is invoked by process 1600 (e.g., at 1615).

At 2405, the system obtains indication that the geographic region is to be partitioned. The system may determine that the geographic region is to be partitioned in response to determining that another set of one or more sessions are to be assigned drive plans. For example, the system determines to partition the geographic region each day one or more mobile sensors are to be deployed in the geographic region.

At 2410, the system selects a characteristic to be monitored. The system may monitor a plurality of pollutants or other characteristics over the geographic region. The plurality of pollutants or other characteristics to be monitored may be determined based at least in part on a contract or order for a monitoring of air quality in the geographic regions. Examples of pollutants that may be monitored over the geographic region include carbon monoxide, lead, nitrogen oxides, ozone, particulate matter, sulfur dioxide, methane, etc. Examples of other characteristics that may be monitored over the geographic region include pollen, precipitation level, level of background sound, traffic, etc. Various other pollutants or characteristics may be monitored over the geographic region.

At 2415, the system determines a partitioning of the geographic region for the selected characteristic. In some embodiments, the system determines a partitioning of the geographic region based at least in part on a data quality measure for the selected characteristic. For example, the system determines a spatial data variance across the geographic region for the selected characteristic.

At 2420, the system stores the partitioning in a set of partitionings.

At 2425, the system determines whether the geographic region is to be partitioned for another characteristics. For example, the system determines whether the geographic region is to be, or being, monitored for more characteristics. As another example, the system determines whether other characteristics are to be used to partition the geographic region for selection of target regions or target locations to be sampled during a set of one or more sessions.

In response to determining the geographic region is to be partitioned for another characteristic(s) at 2425, process 2400 returns to 2410 and process 2400 iterates over 2410 to 2425 until there are no further characteristics for which the geographic region is to be partitioned. Conversely, in response to determining that the geographic region is not to be partitioned for any further characteristics, process 2400 proceeds to 2430.

At 2430, the system selects a location within the geographic region. In some embodiments, the system randomly selects locations within the geographic region for which an aggregated partition (e.g., a partition considering a plurality of characteristics) are to be determined. The system may iterates over a set of J randomly selected locations over the geographic region, where J is a positive integer. In some embodiments, aggregated partitionings are determined for a plurality of predefined locations (e.g., locations that may be equally spaced across the geographic region, etc.).

At 2435, the system obtains, from the set of partitionings, the partitions for the selected hexagon. For the selected location, the system determines the various partitioning across each of the characteristics (e.g., the characteristics selected over the iterations of 2410). As an example, the system determines a granularity of the partitioning at the selected location for each of the characteristics. As another example, for each pollutant being monitored, the system determines a size of the hexagon in which the selected location is comprised for the corresponding partitioning. The system obtains the hexagon size in each of the partitioning layers.

At 2440, the system determines an aggregated partition for the selected location based at least in part on the obtained partitions for the selected location. In some embodiments, determining the aggregated partition (at least for the selected location) includes flattening to a single aggregated partitioning layer the plurality of partitioning layers for the various characteristics. The aggregated partitioning for the selected location may be set as the finest granularity (e.g., the smallest sized hexagon) across the plurality of partitionings for the characteristics.

At 2445, the system determines whether aggregated partitions are to be determined for further locations.

In response to determining that aggregated partitions are to be determined for further locations at 2445, process 2400 returns to 2430 and process 2400 iterates over 2430 to 2445 until no further locations exist for which aggregated partitions are to be determined. Conversely, in response to determining that no further locations exist for which aggregated partitions are to be determined at 2445, process 2400 proceeds to 2450.

At 2450, the system provides the aggregated partitioning. The system provides the aggregated partitioning to another system, module, or process that invoked process 2400. For example, the system provides the aggregated partitioning for to a system or process that is used to perform a targeting (e.g., identify target regions or target locations) for a set of sessions. As another example, the providing the aggregated partitioning includes providing an aggregated partitioning layer for the geographic region.

At 2455, a determination is made as to whether process 2400 is complete. In some embodiments, process 2400 is determined to be complete in response to a determination that no further air quality measurements are to be collected, no further aggregated partitions are to be determined, no further sessions or air quality measurement systems/platforms are to be assigned target regions, all air quality measurement systems/platforms have been assigned a plan for collecting air quality measurements during a session (e.g., day), an administrator indicates that process 2400 is to be paused or stopped, etc. In response to a determination that process 2400 is complete, process 2400 ends. In response to a determination that process 2400 is not complete, process 2400 returns to 2405.

Figure 25:
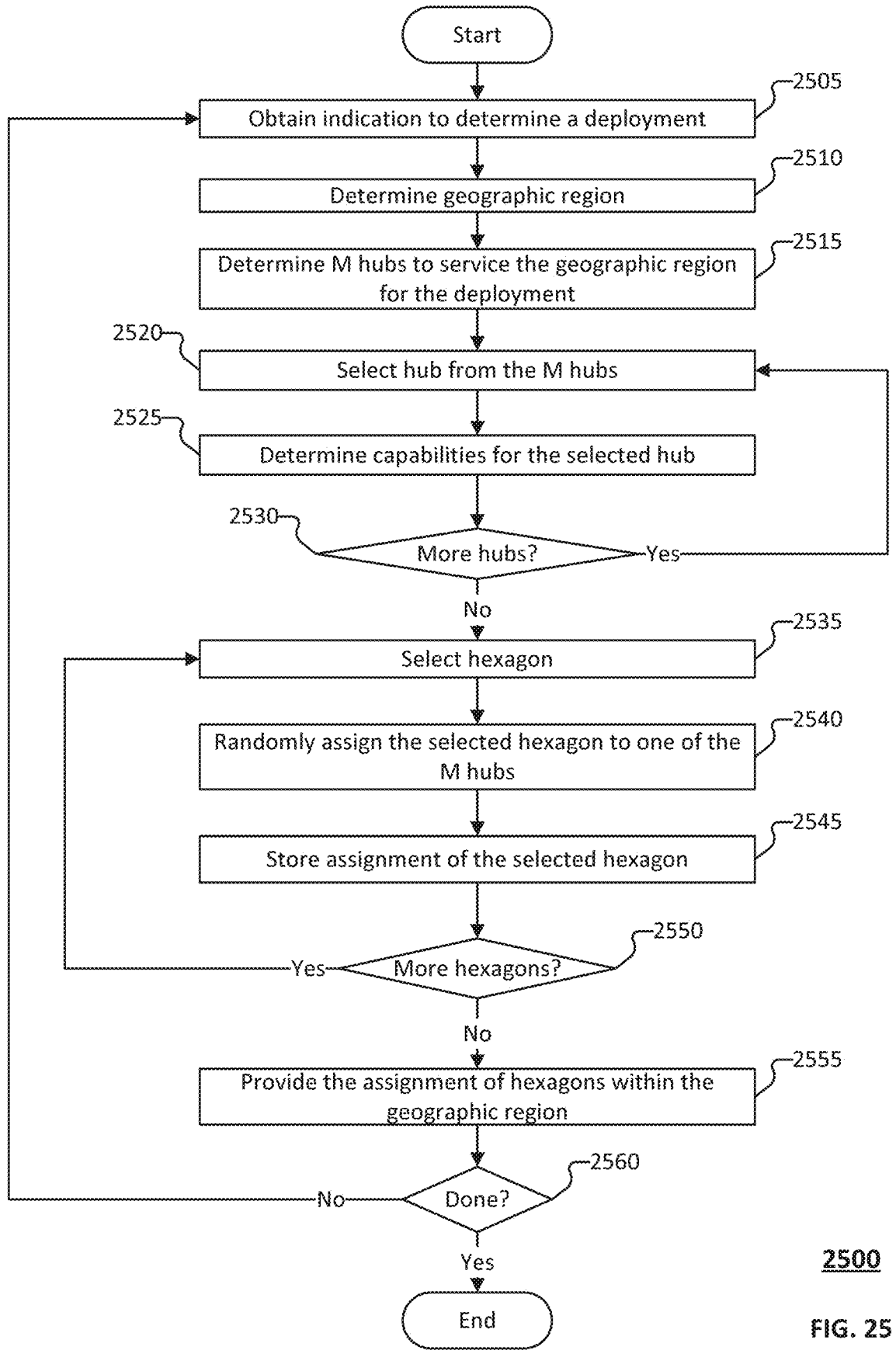
FIG. 25 illustrates a method for assigning target regions to sessions for air quality measurements collection according to various embodiments.

FIG. 25 illustrates a method for assigning target regions to sessions for air quality measurement collection according to various embodiments. In some embodiments, process 2500 is implemented at least in part by system 100 of FIG. 1. In some embodiments, process 2500 is invoked by process 1600 (e.g., at 1615).

At 2505, the system obtains an indication to determine a deployment. The system may determine that a deployment is to be determined in response to determining that a set of sessions are to be planned (e.g., a set of drive plans are to be determined for one or more vehicles for a particular day).

At 2510, the system determines the geographic region.

At 2515, the system determines M hubs to service the geographic region for the deployment, where M is a positive integer. The system may determine the M hubs to service the geographic region based on a predefined assignment of hubs to the geographic region. The system may determine the M hubs to service the geographic region based on capabilities of available hubs, such as hubs available to drive within the geographic region and equipped with appropriate sensors, etc.

At 2520, the system selects a hub from the M hubs.

At 2525, the system determines capabilities for the selected hub.

At 2530, the system determines whether capabilities are to be determined for another hub(s). In response to determining that capabilities are to be determined for another hub(s), process 2500 returns to 2520 and process 2500 iterates over 2520 to 2530 until no further capabilities are to be determined for the hubs.

At 2535, the system selects a hexagon.

At 2540, the system randomly assigns the selected hexagon to one of the M hubs. The random assignment of the selected hexagon may be based on a weightings of the M hubs for the particular hexagon. For each particular hexagon, the corresponding weighting associated with a particular hub may be based on the capabilities of the hub, a distance between the hexagon and the hub, etc.

At 2545, the system stores the assignment of the selected hexagon.

At 2550, the system determines whether another hexagon(s) is to be assigned to one of the M hubs. In response to determining that another hexagon(s) is to be assigned to one of the M hubs, process 2500 returns to 2535 and process 2500 iterates over 2535-2550. Conversely, in response to determining that no further hexagons are to be assigned to one of the M hubs, process 2500 proceeds to 2555.

At 2555, the system provides the assignment of hexagons within the geographic region. For example, the system determines the service areas assigned to each of the M hubs. The service area for a particular hub is defined based on the boundaries for each of the hexagons assigned to the M hubs. The system can then determine targeting of target regions or target locations to be sampled within the service areas. For each hub, the system determines the corresponding target regions or target locations within the corresponding service area to be sampled by mobile sensor platforms deployable from the hub.

At 2560, a determination is made as to whether process 2500 is complete. In some embodiments, process 2500 is determined to be complete in response to a determination that no further air quality measurements are to be collected, no further deployments are to be processed, no further sessions or air quality measurement systems/platforms are to be assigned target regions, all air quality measurement systems/platforms have been assigned a plan for collecting air quality measurements during a session (e.g., day), an administrator indicates that process 2500 is to be paused or stopped, etc. In response to a determination that process 2500 is complete, process 2500 ends. In response to a determination that process 2500 is not complete, process 2500 returns to 2505.

Although process 2500 is described in connection with assignment of hexagons to M hubs, various other tiling shapes may be implemented. For example, each partition within the geographic region is assigned to a corresponding hub.

Various examples of embodiments described herein are described in connection with flow diagrams. Although the examples may include certain steps performed in a particular order, according to various embodiments, various steps may be performed in various orders and/or various steps may be combined into a single step or in parallel.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for sensing air quality with a sensor platform, comprising:

obtaining historical air quality measurements obtained by a plurality of mobile sensors;

determining, based at least in part on the historical air quality measurements, a statistical variance for each of a plurality of spatial partitions;

determining a coarse region based on the statistical variance of the plurality of spatial partitions, wherein the coarse region corresponds to a first partition whose variance is below a first threshold;

determining a fine region based on the statistical variance of the plurality of spatial partitions, wherein the fine region corresponds to a second partition whose variance exceeds a second threshold;

directing a first subset of mobile sensors to the coarse region; and directing a second subset of mobile sensors to the fine region;

wherein a variance of air quality measurements associated with the fine region is greater than a variance of air quality measurements associated with the coarse region.

2. The method of claim 1, wherein the first subset of the set of mobile sensors is mounted to a first subset of vehicles, and the second subset of the set of mobile sensors is mounted to a second subset of vehicles.

3. The method of claim 1, wherein the coarse region is determined based at least in part on:

determining N partitioning layers for each of N pollutants to be measured across a predefined geographic region;

selecting a location within the geographic region; and determining the coarse region at the location based on sizes of partitions that contain the location across the N partitioning layers.

4. The method of claim 1, wherein the plurality of mobile sensors obtains a plurality of air quality measurements at a plurality of locations.

5. The method of claim 4, further comprising:

defining a geographic region including at least a subset of the plurality of locations, and the geographic region comprises one or both of the coarse region and the fine region.

6. The method of claim 1, further comprising:

obtaining a plurality of air quality measurements based on sensor data obtained from the plurality of mobile sensors, wherein the plurality of air quality measurements are respectively associated with a set of locations; and determining one or more neighboring air quality measurements for a set of neighboring locations that are within a predefined proximity of the set of locations.

7. The method of claim 1, further comprising:

obtaining a geographic region comprising locations at which air quality is to be measured; and defining at least a subset of the geographic region into one or more polygons.

8. The method of claim 7, wherein the one or more polygons are hexagons.

9. The method of claim 8, wherein defining the one or more polygons includes determining a size of a hexagon.

10. The method of claim 9, wherein the size of the hexagon is determined based at least in part on a variance of historical information collected for a part of the geographic region comprised in the hexagon.

11. The method of claim 9, wherein at least a subset of the set of mobile sensors is directed to a first location in the hexagon.

12. The method of claim 11, wherein the subset of the set of mobile sensors is directed to a first road segment within the hexagon.

13. The method of claim 8, wherein the hexagons are linearly defined.

14. The method of claim 8, wherein defining the one or more polygons includes:

dividing the geographic region into a plurality of hexagons having a particular size;

determining a group of seven hexagons of the plurality of hexagons;

determining a data quality for each of the seven hexagons within the group of seven hexagons; and determining a data quality of a larger hexagon formed by grouping the seven hexagons.

15. The method of claim 14, wherein defining the one or more polygons includes:

in response to determining that the data quality for the larger hexagon satisfies a predefined criteria, deeming the larger hexagon to be the coarse region to which the set of mobile sensors are to be directed.

16. The method of claim 15, wherein the predefined criteria comprises a data variance of prior air quality measurements taken at locations within the larger hexagon exceeding a predefined variance threshold.

17. The method of claim 14, wherein defining the one or more polygons includes:

in response to determining that the data quality for the larger hexagon has a data variance of prior air quality measurements taken at locations within the larger hexagon is less than a predefined variance threshold, deeming the corresponding seven hexagons of the particular size as a set of fine regions to which the plurality of mobile sensors are to be directed.

18. The method of claim 1, further comprising:

determining a first set of target regions for which air quality is to be measured by at least a subset of the plurality of mobile sensors during a session, the first set of target regions comprising one or both of a subset of coarse regions and a subset of fine regions.

19. The method of claim 18, wherein the first set of target regions for which air quality is to be measured during a session is based at least in part on a spatial diversity of prior air quality measurements taken within the first set of target regions.

20. The method of claim 18, wherein the first set of target regions are randomly selected from a second set of regions.

21. The method of claim 20, wherein the first set of target regions are randomly selected based at least in part on a weighting of each target region.

22. The method of claim 21, wherein the weighting of each target region is respectively assigned based at least in part on a pass count corresponding to a number of prior air quality measurements taken within the particular target region.

23. The method of claim 18, wherein further comprising:

selecting for each target region at least one road segment at which the air quality is to be measured.

24. The method of claim 18, further comprising:

determining turn-by-turn directions to navigate a vehicle to the first set of target regions during the session, wherein the vehicle comprises at least a subset of the set of mobile sensors thereon.

25. The method of claim 1, wherein the coarse region and the fine region are comprised in a service area assigned to one of a plurality of hubs that service a geographic region, and the mobile sensors directed to the coarse region and the fine region are assigned to the hub.

26. A system for sensing air quality with a sensor platform, comprising:

a processor configured to:

obtain historical air quality measurements obtained by a plurality of mobile sensors;

determine, based at least in part on the historical air quality measurements, a statistical variance for each of a plurality of spatial partitions;

determine a coarse region based on the statistical variance of the plurality of spatial partitions, wherein the coarse region corresponds to a first partition whose variance is below a first threshold;

determine a fine region based on the statistical variance of the plurality of spatial partitions, wherein the fine region corresponds to a second partition whose variance exceeds a second threshold;

direct a first subset of mobile sensors to the coarse region; and direct a second subset set of mobile sensors to the fine region;

wherein a variance of air quality measurements associated with the fine region is greater than a variance of air quality measurements associated with the coarse region; and a memory coupled to the processor and configured to provide the processor with instructions.

27. A computer program product for sensing air quality with a sensor platform, the computer program product being embodied in a tangible computer readable storage medium and comprising computer instructions for:

obtaining historical air quality measurements obtained by a plurality of mobile sensors;

determining, based at least in part on the historical air quality measurements, a statistical variance for each of a plurality of spatial partitions;

determining a coarse region based on the statistical variance of the plurality of spatial partitions, wherein the coarse region corresponds to a first partition whose variance is below a first threshold;

determining a fine region based on the statistical variance of the plurality of spatial partitions, wherein the fine region corresponds to a second partition whose variance exceeds a second threshold;

directing a first subset of mobile sensors to the coarse region; and directing a second subset of mobile sensors to the fine region;

wherein a variance of air quality measurements associated with the fine region is greater than a variance of air quality measurements associated with the coarse region.

\* \* \* \* \*